(12) United States Patent
Dietrich et al.

(10) Patent No.: US 12,188,008 B2
(45) Date of Patent: Jan. 7, 2025

(54) RECOMBINANT HOST CELLS AND METHODS FOR THE PRODUCTION OF GLYCERIC ACID AND DOWNSTREAM PRODUCTS

(71) Applicant: Lygos, Inc., Hayward, CA (US)

(72) Inventors: Jeffrey A. Dietrich, Hayward, CA (US); Mario Ouellet, Hayward, CA (US); Johan van Walsem, Hayward, CA (US)

(73) Assignee: Lygos, Inc., Hayward, CA (US)

( * ) Notice: Subject to any disclaimer, the term of this patent is extended or adjusted under 35 U.S.C. 154(b) by 967 days.

(21) Appl. No.: 16/969,866

(22) PCT Filed: Feb. 18, 2019

(86) PCT No.: PCT/US2019/018422
§ 371 (c)(1),
(2) Date: Aug. 13, 2020

(87) PCT Pub. No.: WO2019/161335
PCT Pub. Date: Aug. 22, 2019

(65) Prior Publication Data
US 2021/0061748 A1 Mar. 4, 2021

Related U.S. Application Data

(60) Provisional application No. 62/632,237, filed on Feb. 19, 2018.

(51) Int. Cl.
*C12N 9/88* (2006.01)
*C12N 1/16* (2006.01)
*C12N 1/20* (2006.01)
*C12N 9/02* (2006.01)
*C12N 9/12* (2006.01)
*C12N 9/16* (2006.01)
*C12N 9/90* (2006.01)
*C12P 7/42* (2006.01)
*C12R 1/72* (2006.01)
*C12R 1/84* (2006.01)
*C12R 1/865* (2006.01)

(52) U.S. Cl.
CPC .............. *C12N 1/16* (2013.01); *C12N 1/20* (2013.01); *C12N 9/0036* (2013.01); *C12N 9/1205* (2013.01); *C12N 9/16* (2013.01); *C12N 9/88* (2013.01); *C12N 9/90* (2013.01); *C12P 7/42* (2013.01); *C12N 2523/00* (2013.01); *C12R 2001/72* (2021.05); *C12R 2001/84* (2021.05); *C12R 2001/865* (2021.05); *C12Y 101/01008* (2013.01); *C12Y 106/03001* (2013.01); *C12Y 106/99003* (2013.01); *C12Y 207/01031* (2013.01); *C12Y 207/01165* (2013.01); *C12Y 301/0302* (2013.01); *C12Y 301/03038* (2013.01); *C12Y 402/01011* (2013.01); *C12Y 504/02001* (2013.01)

(58) Field of Classification Search
CPC ... C12N 9/88; C12N 1/16; C12N 1/20; C12Y 301/03012; C12Y 301/0302
See application file for complete search history.

(56) References Cited

U.S. PATENT DOCUMENTS

| | | |
|---|---|---|
| 2003/0233675 A1 | 12/2003 | Cao et al. |
| 2013/0102046 A1 | 4/2013 | Jin et al. |
| 2017/0044551 A1 | 2/2017 | Chokhawala |
| 2017/0349920 A1 | 12/2017 | Sohn et al. |

OTHER PUBLICATIONS

Habe et al., Membrane-bound alcohol dehydrogenase is essential for glyceric acid production in Acetobacter tropicalis, Journal of Oleo Science, vol. 60, No. 9, 2011, pp. 489-494.
International Preliminary Report on Patentability received for PCT Patent Application No. PCT/US2019/018422, mailed on Sep. 3, 2020, 8 pages.
International Search Report and Written Opinion received for PCT Patent Application No. PCT/US2019/018422, mailed on Jul. 9, 2019, 12 pages.

*Primary Examiner* — Tekchand Saidha
(74) *Attorney, Agent, or Firm* — Faegre Drinker Biddle & Reath LLP

(57) ABSTRACT

Methods and materials related to producing glyceric acid and downstream products are disclosed. Specifically, isolated nucleic acids, polypeptides, host cells, methods and materials for producing glycolic acid by direct fermentation from sugars are disclosed.

14 Claims, No Drawings
Specification includes a Sequence Listing.

ically as high as 350°

SEQUENCE LISTING

<160> NUMBER OF SEQ ID NOS: 30

<210> SEQ ID NO 1
<211> LENGTH: 252
<212> TYPE: PRT
<213> ORGANISM: Escherichia coli

<400> SEQUENCE: 1

```
Met Asn Lys Phe Glu Asp Ile Arg Gly Val Ala Phe Asp Leu Asp Gly
1               5                   10                  15

Thr Leu Val Asp Ser Ala Pro Gly Leu Ala Ala Ala Val Asp Met Ala
            20                  25                  30

Leu Tyr Ala Leu Glu Leu Pro Val Ala Gly Glu Glu Arg Val Ile Thr
        35                  40                  45

Trp Ile Gly Asn Gly Ala Asp Val Leu Met Glu Arg Ala Leu Thr Trp
    50                  55                  60

Ala Arg Gln Glu Arg Ala Thr Gln Arg Lys Thr Met Gly Lys Pro Pro
65                  70                  75                  80

Val Asp Asp Asp Ile Pro Ala Glu Glu Gln Val Arg Ile Leu Arg Lys
                85                  90                  95

Leu Phe Asp Arg Tyr Tyr Gly Glu Val Ala Glu Gly Thr Phe Leu
            100                 105                 110

Phe Pro His Val Ala Asp Thr Leu Gly Ala Leu Gln Ala Lys Gly Leu
        115                 120                 125
```

```
Pro Leu Gly Leu Val Thr Asn Lys Pro Thr Pro Phe Val Ala Pro Leu
    130                 135                 140

Leu Glu Ala Leu Asp Ile Ala Lys Tyr Phe Ser Val Val Ile Gly Gly
145                 150                 155                 160

Asp Asp Val Gln Asn Lys Lys Pro His Pro Asp Pro Leu Leu Leu Val
                165                 170                 175

Ala Glu Arg Met Gly Ile Ala Pro Gln Gln Met Leu Phe Val Gly Asp
            180                 185                 190

Ser Arg Asn Asp Ile Gln Ala Ala Lys Ala Ala Gly Cys Pro Ser Val
        195                 200                 205

Gly Leu Thr Tyr Gly Tyr Asn Tyr Gly Glu Ala Ile Asp Leu Ser Gln
    210                 215                 220

Pro Asp Val Ile Tyr Gln Ser Ile Asn Asp Leu Leu Pro Ala Leu Gly
225                 230                 235                 240

Leu Pro His Ser Glu Asn Gln Glu Ser Lys Asn Asp
                245                 250

<210> SEQ ID NO 2
<211> LENGTH: 411
<212> TYPE: PRT
<213> ORGANISM: Mycobacterium avium

<400> SEQUENCE: 2

Met Asn Ser Pro Pro Lys Val Ser Val Leu Ile Thr Val Thr Gly Val
1               5                   10                  15

Asp Gln Pro Gly Val Thr Ala Thr Leu Phe Glu Val Leu Ser Gly His
            20                  25                  30

Gly Val Glu Leu Leu Asn Val Glu Gln Val Val Ile Arg His Arg Leu
        35                  40                  45

Thr Leu Gly Val Leu Val Cys Cys Pro Ala Asp Val Ala Asp Gly Pro
    50                  55                  60

Ala Leu Arg His Asp Val Glu Ala Ala Ile Arg Lys Val Gly Leu Asp
65                  70                  75                  80

Val Ser Ile Glu Arg Ser Asp Asp Val Pro Ile Ile Arg Glu Pro Ser
                85                  90                  95

Thr His Thr Ile Phe Val Leu Gly Arg Pro Ile Thr Ala Ala Ala Phe
            100                 105                 110

Gly Ala Val Ala Arg Glu Val Ala Ala Leu Gly Val Asn Ile Asp Leu
        115                 120                 125

Ile Arg Gly Val Ser Asp Tyr Pro Val Ile Gly Leu Glu Leu Arg Val
    130                 135                 140

Ser Val Pro Pro Gly Ala Asp Gly Ala Leu Arg Thr Ala Leu Asn Arg
145                 150                 155                 160

Val Ser Ser Glu Glu His Val Asp Val Ala Val Glu Asp Tyr Thr Leu
                165                 170                 175

Glu Arg Arg Ala Lys Arg Leu Ile Val Phe Asp Val Asp Ser Thr Leu
            180                 185                 190

Val Gln Gly Glu Val Ile Glu Met Leu Ala Ala Lys Ala Gly Ala Glu
        195                 200                 205

Gly Gln Val Ala Ala Ile Thr Asp Ala Ala Met Arg Gly Glu Leu Asp
    210                 215                 220

Phe Ala Gln Ser Leu Gln Gln Arg Val Ala Thr Leu Ala Gly Leu Pro
225                 230                 235                 240

Ala Thr Val Ile Asp Glu Val Ala Gly Gln Leu Glu Leu Met Pro Gly
                245                 250                 255
```

```
Ala Arg Thr Thr Leu Arg Thr Leu Arg Arg Leu Gly Tyr Ala Cys Gly
            260                 265                 270

Val Val Ser Gly Gly Phe Arg Ile Ile Glu Pro Leu Ala Glu Glu
            275                 280                 285

Leu Met Leu Asp Tyr Val Ala Ala Asn Glu Leu Glu Ile Val Asp Gly
            290                 295                 300

Thr Leu Thr Gly Arg Val Val Gly Pro Ile Ile Asp Arg Ala Gly Lys
305                 310                 315                 320

Ala Thr Ala Leu Arg Glu Phe Ala Gln Arg Ala Gly Val Pro Met Ala
            325                 330                 335

Gln Thr Val Ala Val Gly Asp Gly Ala Asn Asp Ile Asp Met Leu Ala
            340                 345                 350

Ala Ala Gly Leu Gly Ile Ala Phe Asn Ala Lys Pro Ala Leu Arg Glu
            355                 360                 365

Val Ala Asp Ala Ser Leu Ser His Pro Tyr Leu Asp Thr Val Leu Phe
            370                 375                 380

Leu Leu Gly Val Thr Arg Gly Glu Ile Glu Ala Ala Asp Ala Ile Asp
385                 390                 395                 400

Gly Glu Val Arg Arg Val Glu Ile Pro Pro Glu
            405                 410

<210> SEQ ID NO 3
<211> LENGTH: 224
<212> TYPE: PRT
<213> ORGANISM: Haemophilus somnus

<400> SEQUENCE: 3

Met Thr Gln Phe Lys Leu Ile Gly Phe Asp Leu Asp Gly Thr Leu Val
1               5                   10                  15

Asn Ser Leu Pro Asp Leu Ala Leu Ser Ile Asn Ser Ala Leu Lys Asp
            20                  25                  30

Val Asn Leu Pro Gln Ala Ser Glu Asn Leu Val Met Thr Trp Ile Gly
            35                  40                  45

Asn Gly Ala Asp Val Leu Ser Gln Arg Ala Val Asp Trp Ala Cys Lys
        50                  55                  60

Gln Ala Glu Lys Glu Leu Thr Glu Asp Glu Phe Lys Tyr Phe Lys Arg
65                  70                  75                  80

Gln Phe Gly Phe Tyr Tyr Gly Glu Asn Leu Cys Asn Ile Ser Arg Leu
                85                  90                  95

Tyr Pro Asn Val Lys Glu Thr Leu Glu Ala Leu Lys Ala Gln Gly Tyr
            100                 105                 110

Ile Leu Ala Val Val Thr Asn Lys Pro Thr Lys His Val Gln Pro Ile
            115                 120                 125

Leu Thr Ala Phe Gly Ile Asp His Leu Phe Ser Glu Met Leu Gly Gly
            130                 135                 140

Gln Ser Leu Pro Glu Ile Lys Pro His Pro Ala Pro Phe Tyr Tyr Leu
145                 150                 155                 160

Cys Gly Lys Phe Gly Leu Tyr Pro Lys Gln Ile Leu Phe Val Gly Asp
                165                 170                 175

Ser Gln Asn Asp Ile Phe Ala Ala His Ser Ala Gly Cys Ala Val Val
            180                 185                 190

Gly Leu Thr Tyr Gly Tyr Asn Tyr Asn Ile Pro Ile Ala Gln Ser Lys
            195                 200                 205

Pro Asp Trp Ile Phe Asp Asp Phe Ala Asp Ile Leu Lys Ile Thr Gln
```

<210> SEQ ID NO 4
<211> LENGTH: 250
<212> TYPE: PRT
<213> ORGANISM: Saccharomyces cerevisiae

<400> SEQUENCE: 4

Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Gly Ser Ile Arg Val Gly
210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 5
<211> LENGTH: 321
<212> TYPE: PRT
<213> ORGANISM: Homo sapiens

<400> SEQUENCE: 5

Met Ala Ala Ala Glu Ala Gly Gly Asp Asp Ala Arg Cys Val Arg Leu
1               5                   10                  15

Ser Ala Glu Arg Ala Gln Ala Leu Leu Ala Asp Val Asp Thr Leu Leu
            20                  25                  30

Phe Asp Cys Asp Gly Val Leu Trp Arg Gly Glu Thr Ala Val Pro Gly
        35                  40                  45

Ala Pro Glu Ala Leu Arg Ala Leu Arg Ala Arg Gly Lys Arg Leu Gly
50                  55                  60

Phe Ile Thr Asn Asn Ser Ser Lys Thr Arg Ala Ala Tyr Ala Glu Lys

```
                65                  70                  75                  80
Leu Arg Arg Leu Gly Phe Gly Gly Pro Ala Gly Pro Gly Ala Ser Leu
                    85                  90                  95

Glu Val Phe Gly Thr Ala Tyr Cys Thr Ala Leu Tyr Leu Arg Gln Arg
                    100                 105                 110

Leu Ala Gly Ala Pro Ala Pro Lys Ala Tyr Val Leu Gly Ser Pro Ala
                    115                 120                 125

Leu Ala Ala Glu Leu Glu Ala Val Gly Val Ala Ser Val Gly Val Gly
                    130                 135                 140

Pro Glu Pro Leu Gln Gly Glu Gly Pro Gly Asp Trp Leu His Ala Pro
145                 150                 155                 160

Leu Glu Pro Asp Val Arg Ala Val Val Gly Phe Asp Pro His Phe
                    165                 170                 175

Ser Tyr Met Lys Leu Thr Lys Ala Leu Arg Tyr Leu Gln Gln Pro Gly
                    180                 185                 190

Cys Leu Leu Val Gly Thr Asn Met Asp Asn Arg Leu Pro Leu Glu Asn
                    195                 200                 205

Gly Arg Phe Ile Ala Gly Thr Gly Cys Leu Val Arg Ala Val Glu Met
                    210                 215                 220

Ala Ala Gln Arg Gln Ala Asp Ile Ile Gly Lys Pro Ser Arg Phe Ile
225                 230                 235                 240

Phe Asp Cys Val Ser Gln Glu Tyr Gly Ile Asn Pro Glu Arg Thr Val
                    245                 250                 255

Met Val Gly Asp Arg Leu Asp Thr Asp Ile Leu Leu Gly Ala Thr Cys
                    260                 265                 270

Gly Leu Lys Thr Ile Leu Thr Leu Thr Gly Val Ser Thr Leu Gly Asp
                    275                 280                 285

Val Lys Asn Asn Gln Glu Ser Asp Cys Val Ser Lys Lys Met Val
                    290                 295                 300

Pro Asp Phe Tyr Val Asp Ser Ile Ala Asp Leu Leu Pro Ala Leu Gln
305                 310                 315                 320

Gly

<210> SEQ ID NO 6
<211> LENGTH: 550
<212> TYPE: PRT
<213> ORGANISM: Synechococcus elongatus

<400> SEQUENCE: 6

Met Lys Ile Lys Leu Leu Cys Ile Ser Leu Ala Val Leu Phe Cys Ser
1               5                   10                  15

Ser Ala Asn Ala Gln Lys Lys Gln Ala Lys Val Gln Pro Ser Val Phe
                20                  25                  30

Pro Gln Thr Val Ala Arg Pro Lys Leu Val Val Gly Met Val Ile Asp
            35                  40                  45

Gln Met Arg Trp Asp Tyr Leu Tyr Arg Phe Tyr Ala Arg Tyr Gly Asn
        50                  55                  60

Gly Gly Phe Lys Arg Leu Ile Asn Glu Gly Phe Ser Ala Glu Asn Thr
65                  70                  75                  80

Leu Ile Pro Tyr Thr Pro Thr Leu Thr Ala Cys Gly His Ser Ser Ile
                85                  90                  95

Tyr Thr Gly Ser Val Pro Ala Ile Asn Gly Ile Ile Gly Asn Asn Trp
                100                 105                 110

Phe Asp Pro Gln Leu Gly Arg Asp Val Tyr Cys Val Glu Asp Lys Ser
```

```
            115                 120                 125
Val Lys Thr Val Gly Ser Ser Asn Glu Gly Leu Met Ser Pro Lys
        130                 135                 140
Asn Leu Leu Val Thr Thr Val Thr Asp Glu Leu Arg Met Ala Thr Asn
145                 150                 155                 160
Phe Arg Ser Lys Val Ile Ser Val Ser Ile Lys Asp Arg Gly Ala Ile
                165                 170                 175
Leu Pro Gly Gly His Thr Ala Asn Gly Ala Tyr Trp Tyr Asp Asp Met
                180                 185                 190
Thr Gly Ser Phe Ile Ser Ser Thr His Tyr Met Gln Gln Leu Pro Thr
        195                 200                 205
Trp Val Asn Asp Phe Asn Ala Gln Arg Leu Pro Asn Lys Tyr Phe Glu
    210                 215                 220
Gln Asp Trp Asn Thr Leu Tyr Pro Ile Glu Thr Tyr Thr Glu Ser Thr
225                 230                 235                 240
Ala Asp Ala Lys Pro Tyr Glu Arg Thr Phe Lys Gly Ala Lys Thr Ser
                245                 250                 255
Ser Phe Pro His Leu Phe Lys Gln Tyr Ala Asn Lys Asn Tyr Ser Met
                260                 265                 270
Met Ala Ser Met Pro Gln Gly Asn Ser Phe Thr Leu Glu Phe Ala Lys
        275                 280                 285
Ala Ala Ile Pro Ala Glu Lys Leu Gly Gln Thr Gly Asn Thr Asp Phe
    290                 295                 300
Leu Ala Val Ser Leu Ser Ser Thr Asp Tyr Val Gly His Gln Phe Gly
305                 310                 315                 320
Pro Asn Ser Ile Glu Leu Glu Asp Thr Tyr Leu Arg Leu Asp Lys Asp
                325                 330                 335
Leu Glu Asp Phe Phe Asn Tyr Leu Asp Lys Thr Ile Gly Lys Gly Asn
                340                 345                 350
Tyr Leu Leu Phe Leu Thr Ala Asp His Gly Ala Thr His Val Pro Gly
        355                 360                 365
Phe Leu Arg Asn Lys Met Pro Gly Gly Arg Leu Leu Leu Lys Val Gln
    370                 375                 380
Thr Asp Leu Asp Ser Leu Ile Phe Asn Glu Phe Lys Val Arg Cys Asn
385                 390                 395                 400
Phe Thr Ile Ile Asn Asn Gln Val Ile Phe Asp Thr Asp Ala Ile Lys
                405                 410                 415
Glu Ala Lys Ala Asp Tyr Ala Lys Ile Lys Gln Ser Thr Ile Asp Tyr
                420                 425                 430
Leu Val Lys Gln Asp Gly Val Leu Asn Ala Val Asp Ile Lys Asn Met
        435                 440                 445
Gly Ala Val Thr Ile Pro Gln Glu Ile Lys Asn Lys Ile Ile Asn Gly
    450                 455                 460
Tyr Asn Ala Arg Arg Ser Gly Asp Val Tyr Ile Ile Leu Asp Ala Gly
465                 470                 475                 480
Trp Tyr Pro Thr Leu Thr Pro Gly Thr Gly His Ala Ala Trp Asn Pro
                485                 490                 495
Tyr Asp Ser His Ile Pro Ala Leu Phe Met Gly Trp Gly Val Lys Pro
                500                 505                 510
Gly Lys Thr Asn Lys Glu Tyr Tyr Met Ser Asp Ile Ala Pro Thr Val
        515                 520                 525
Ser Ala Leu Leu His Ile Gln Gln Pro Ser Gly Ser Ile Gly Lys Val
    530                 535                 540
```

Ile Thr Asp Leu Leu Lys
545                 550

<210> SEQ ID NO 7
<211> LENGTH: 321
<212> TYPE: PRT
<213> ORGANISM: Artificial Sequence
<220> FEATURE:
<223> OTHER INFORMATION: Synthetic Sequence

<400> SEQUENCE: 7

Met Met Thr Thr Thr Met Met Pro Ile Lys Ile Thr Thr Lys Glu Gln
1               5                   10                  15

Val Gln Glu Phe Leu Asp Lys Tyr Asp Thr Phe Leu Phe Asp Cys Asp
            20                  25                  30

Gly Val Leu Trp Leu Gly Asp His Leu Leu Pro Ser Val Lys Glu Thr
        35                  40                  45

Leu Asp Leu Leu Lys Ser Leu Gly Lys Gln Leu Ile Phe Val Thr Asn
    50                  55                  60

Asn Ser Thr Lys Ser Arg Ala Ala Tyr Thr Lys Lys Phe Ala Lys Phe
65                  70                  75                  80

Gly Ile Thr Gly Val Thr Glu Asp Glu Ile Phe Gly Ser Ser Tyr Ala
                85                  90                  95

Ser Ala Val Tyr Val Arg Asp Phe Leu Lys Leu Pro Pro Gly Lys Asp
            100                 105                 110

Lys Val Trp Val Phe Gly Glu Ser Gly Ile Glu Glu Leu Lys Glu
        115                 120                 125

Met Gly Tyr Glu Thr Leu Gly Gly Thr Asp Pro Arg Leu Asp Glu Pro
    130                 135                 140

Gly Val Lys Phe Asp Ala Asp Thr Ser Pro Phe Leu Val Asn Gly Leu
145                 150                 155                 160

Asp Pro Asp Val Gly Cys Val Val Ala Gly Leu Asp Thr Lys Ile Asn
                165                 170                 175

Tyr His Arg Leu Ala Ile Thr Leu Gln Tyr Leu Gln Lys Asp Asn Pro
            180                 185                 190

Ser Val Pro Phe Val Ala Thr Asn Ile Asp Ser Thr Phe Pro Gln Lys
        195                 200                 205

Gly Lys Leu Leu Pro Gly Ala Gly Ser Ile Ile Glu Ser Val Ala Phe
    210                 215                 220

Ala Ser Gly Arg Gln Pro Asp Ala Ala Cys Gly Lys Pro Asn Gln Asn
225                 230                 235                 240

Met Leu Asn Ser Ile Lys Ala Ala Lys Pro Gly Leu Asn Leu Asp Pro
                245                 250                 255

Ser Arg Cys Cys Met Val Gly Asp Arg Leu Asn Thr Asp Met Lys Phe
            260                 265                 270

Gly Arg Asp Gly Gly Leu Gly Gly Thr Leu Leu Val Leu Thr Gly Ile
        275                 280                 285

Glu Thr Glu Glu Arg Ala Leu Ala Leu Ser Asp Glu His Pro Ala Pro
    290                 295                 300

Lys Tyr Tyr Ala Asp Lys Leu Gly Asp Leu Tyr Glu Leu Thr His Asn
305                 310                 315                 320

Asn

<210> SEQ ID NO 8
<211> LENGTH: 266

```
<212> TYPE: PRT
<213> ORGANISM: Escherichia coli

<400> SEQUENCE: 8

Met Tyr Gln Val Val Ala Ser Asp Leu Asp Gly Thr Leu Leu Ser Pro
1               5                   10                  15

Asp His Thr Leu Ser Pro Tyr Ala Lys Glu Thr Leu Lys Leu Leu Thr
            20                  25                  30

Ala Arg Gly Ile Asn Phe Val Phe Ala Thr Gly Arg His His Val Asp
        35                  40                  45

Val Gly Gln Ile Arg Asp Asn Leu Glu Ile Lys Ser Tyr Met Ile Thr
    50                  55                  60

Ser Asn Gly Ala Arg Val His Asp Leu Asp Gly Asn Leu Ile Phe Ala
65                  70                  75                  80

His Asn Leu Asp Arg Asp Ile Ala Ser Asp Leu Phe Gly Val Val Asn
                85                  90                  95

Asp Asn Pro Asp Ile Ile Thr Asn Val Tyr Arg Asp Asp Glu Trp Phe
            100                 105                 110

Met Asn Arg His Arg Pro Glu Glu Met Arg Phe Phe Lys Glu Ala Val
        115                 120                 125

Phe Gln Tyr Ala Leu Tyr Glu Pro Gly Leu Leu Glu Pro Glu Gly Val
    130                 135                 140

Ser Lys Val Phe Phe Thr Cys Asp Ser His Glu Gln Leu Leu Pro Leu
145                 150                 155                 160

Glu Gln Ala Ile Asn Ala Arg Trp Gly Asp Arg Val Asn Val Ser Phe
                165                 170                 175

Ser Thr Leu Thr Cys Leu Glu Val Met Ala Gly Gly Val Ser Lys Gly
            180                 185                 190

His Ala Leu Glu Ala Val Ala Lys Lys Leu Gly Tyr Ser Leu Lys Asp
        195                 200                 205

Cys Ile Ala Phe Gly Asp Gly Met Asn Asp Ala Glu Met Leu Ser Met
    210                 215                 220

Ala Gly Lys Gly Cys Ile Met Gly Ser Ala His Gln Arg Leu Lys Asp
225                 230                 235                 240

Leu His Pro Glu Leu Glu Val Ile Gly Thr Asn Ala Asp Asp Ala Val
                245                 250                 255

Pro His Tyr Leu Arg Lys Leu Tyr Leu Ser
            260                 265

<210> SEQ ID NO 9
<211> LENGTH: 312
<212> TYPE: PRT
<213> ORGANISM: Saccharomyces cerevisiae

<400> SEQUENCE: 9

Met Thr Ala Gln Gln Gly Val Pro Ile Lys Ile Thr Asn Lys Glu Ile
1               5                   10                  15

Ala Gln Glu Phe Leu Asp Lys Tyr Asp Thr Phe Leu Phe Asp Cys Asp
            20                  25                  30

Gly Val Leu Trp Leu Gly Ser Gln Ala Leu Pro Tyr Thr Leu Glu Ile
        35                  40                  45

Leu Asn Leu Leu Lys Gln Leu Gly Lys Gln Leu Ile Phe Val Thr Asn
    50                  55                  60

Asn Ser Thr Lys Ser Arg Leu Ala Tyr Thr Lys Lys Phe Ala Ser Phe
65                  70                  75                  80
```

```
Gly Ile Asp Val Lys Glu Glu Gln Ile Phe Thr Ser Gly Tyr Ala Ser
                85                  90                  95

Ala Val Tyr Ile Arg Asp Phe Leu Lys Leu Gln Pro Gly Lys Asp Lys
            100                 105                 110

Val Trp Val Phe Gly Glu Ser Gly Ile Gly Glu Glu Leu Lys Leu Met
        115                 120                 125

Gly Tyr Glu Ser Leu Gly Gly Ala Asp Ser Arg Leu Asp Thr Pro Phe
    130                 135                 140

Asp Ala Ala Lys Ser Pro Phe Leu Val Asn Gly Leu Asp Lys Asp Val
145                 150                 155                 160

Ser Cys Val Ile Ala Gly Leu Asp Thr Lys Val Asn Tyr His Arg Leu
                165                 170                 175

Ala Val Thr Leu Gln Tyr Leu Gln Lys Asp Ser Val His Phe Val Gly
            180                 185                 190

Thr Asn Val Asp Ser Thr Phe Pro Gln Lys Gly Tyr Thr Phe Pro Gly
        195                 200                 205

Ala Gly Ser Met Ile Glu Ser Leu Ala Phe Ser Ser Asn Arg Arg Pro
    210                 215                 220

Ser Tyr Cys Gly Lys Pro Asn Gln Asn Met Leu Asn Ser Ile Ile Ser
225                 230                 235                 240

Ala Phe Asn Leu Asp Arg Ser Lys Cys Cys Met Val Gly Asp Arg Leu
                245                 250                 255

Asn Thr Asp Met Lys Phe Gly Val Glu Gly Leu Gly Gly Thr Leu
            260                 265                 270

Leu Val Leu Ser Gly Ile Glu Thr Glu Arg Ala Leu Lys Ile Ser
        275                 280                 285

His Asp Tyr Pro Arg Pro Lys Phe Tyr Ile Asp Lys Leu Gly Asp Ile
    290                 295                 300

Tyr Thr Leu Thr Asn Asn Glu Leu
305                 310

<210> SEQ ID NO 10
<211> LENGTH: 300
<212> TYPE: PRT
<213> ORGANISM: Pichia kudriavzevii

<400> SEQUENCE: 10

Met Thr Ile Lys Ile Ala Thr Arg Gly Ala Ala Glu Lys Ile Leu Asp
1               5                   10                  15

Lys Tyr Asp Thr Tyr Leu Phe Asp Cys Asp Gly Val Ile Trp Ile Gly
            20                  25                  30

Asn Glu Leu Leu Pro Ser Val Lys Glu Thr Leu Glu Leu Leu Gln Ser
        35                  40                  45

Lys Lys Lys Asn Leu Ile Phe Val Ser Asn Asn Ser Thr Lys Ala Arg
    50                  55                  60

Asp Gln Tyr Ile Glu Lys Leu Ala Gly Leu Gly Ile His Gly Val Glu
65                  70                  75                  80

Leu Glu Gln Ile Ile Asn Ser Cys Tyr Ser Thr Ala Ile Tyr Ile Asn
                85                  90                  95

Glu Val Leu Gln Leu Asp Lys Ala Lys Lys Ile Trp Val Leu Gly Gln
            100                 105                 110

Glu Gly Ile Thr Lys Glu Val Glu Lys Phe Gly Tyr Glu Thr Val Thr
        115                 120                 125

Phe Lys Asp Leu Glu Ala Lys Phe Gln Glu Glu Leu Thr Val Asp
    130                 135                 140
```

```
Asn Ile Gln Ser Leu Ile Asp Pro Gln Val Gly Cys Val Ile Val Gly
145                 150                 155                 160

Leu Asp Phe Gln Val Thr Tyr Leu Lys Ile Ala Ile Thr Gln Gln Tyr
            165                 170                 175

Leu Phe Asp Arg Lys Ile Pro Phe Ile Ala Thr Asn Ile Asp Ser Thr
            180                 185                 190

Phe Pro Phe Gly Lys Thr Lys Leu Pro Gly Ala Gly Ser Ile Val Glu
            195                 200                 205

Val Ala Ser Phe Cys Ser Gly Arg Glu Pro Asp Ala Ile Cys Gly Lys
            210                 215                 220

Pro Gln Ser Gly Met Met Asp Ser Ile Leu Ser His His Ser Leu Asn
225                 230                 235                 240

Lys Glu Thr Thr Ile Met Val Gly Asp Arg Leu Asn Thr Asp Met Lys
                245                 250                 255

Phe Gly Ser Val Asn Gly Ile Asp Thr Leu Leu Val Leu Thr Gly Ile
            260                 265                 270

Glu Val Glu Glu Ser Val Ala Asn Gly His Ser Asp Val Thr Tyr Tyr
            275                 280                 285

Ala Asp Lys Leu Gly Asp Leu Tyr Asp Leu Thr Lys
290                 295                 300

<210> SEQ ID NO 11
<211> LENGTH: 384
<212> TYPE: PRT
<213> ORGANISM: Pichia kudriavzevii

<400> SEQUENCE: 11

Met Thr Asn Ser Glu Ile Gln Arg Met Ser Thr Pro Val Glu Val
1               5                   10                  15

Ser Gln Gln Leu Glu Ser Lys Gln Asp Ile Gly Phe Val Phe Asp Ile
            20                  25                  30

Asp Gly Val Leu Leu Lys Gly Lys Lys Arg Ile Val Glu Ala Thr Glu
            35                  40                  45

Ile Ile Thr Tyr Leu Gln Lys Glu Lys Ile Pro Phe Ile Leu Leu Thr
50                  55                  60

Asn Gly Gly Met Thr Glu Lys Lys Arg Ile Asp Phe Ile Asn Met
65                  70                  75                  80

Thr Leu Gln Leu Glu Thr Pro Ile His Pro Asp Gln Leu Ile Gln Ala
            85                  90                  95

His Thr Pro Met Lys Thr Leu Ile Pro His His Lys Arg Val Leu Ile
            100                 105                 110

Cys Gly Gly Pro Lys Asp Asp Val Arg Glu Val Ala Glu Ser Tyr Gly
            115                 120                 125

Phe Glu Asp Val Ile Arg Pro Val Asp Ile Ile Arg Ala Asn Pro Thr
            130                 135                 140

Ile Trp Pro Tyr His Met Phe Asp Glu Gln Ile Glu Gln Trp Gly
145                 150                 155                 160

Arg Asp Pro Asn Asp Thr Lys Leu Asp Val Asp Gly Thr Gly Cys Lys
                165                 170                 175

Glu Asn Leu Pro Ile Asp Ser Ile Leu Cys Phe Asn Asp Ser Arg Ala
            180                 185                 190

Leu Gly Ala Glu Ile Gln Ile Ile Ser Asp Leu Leu Asn Ser Glu Asn
            195                 200                 205

Gly Val Leu Gly Thr Arg Arg Thr Val Lys Ser Ser Lys Pro Ser Ile
```

```
            210                 215                 220
Pro Ile Val Phe Ser Asn Asn Asp Phe Leu Trp Ala Asn Glu Phe Val
225                 230                 235                 240

Gln Pro Arg Phe Ala Met Gly Val Leu Lys Ile Ala Thr Gln Thr Ile
                245                 250                 255

Tyr Ser Lys Ile Asn Gly Gly Glu Glu Leu Glu Gln Leu Thr Leu Gly
                260                 265                 270

Lys Pro Glu Lys Val Cys Tyr Asp Tyr Ala His His Ile Leu Ile Asp
                275                 280                 285

Trp Arg Asp Val Leu Leu Gly Lys Lys Ala Gly Asn Val Cys Leu
290                 295                 300

Pro Gln Leu Asn Asn Glu Pro Leu Asn Ser Pro Phe Lys Lys Val Tyr
305                 310                 315                 320

Met Val Gly Asp Asn Pro Glu Ser Asp Ile Thr Gly Gly Asn Arg Tyr
                325                 330                 335

Asn Trp Gly Thr Ile Leu Val Lys Thr Gly Val Tyr Gln Glu Gly Asp
                340                 345                 350

Phe Glu Arg Asn Pro Glu Ile Ser Lys Pro Ser Leu Gly Val Phe Ala
                355                 360                 365

Asn Val Lys Glu Gly Val Met His Ala Leu Lys Leu Asn Gly Leu Ala
370                 375                 380
```

<210> SEQ ID NO 12
<211> LENGTH: 362
<212> TYPE: PRT
<213> ORGANISM: Pichia kudriavzevii

<400> SEQUENCE: 12

```
Met Leu Ser Leu Gln Phe Lys Arg Leu Ile His Ser Ile Lys Lys Ser
1               5                   10                  15

Pro Val Gly Phe Ala Phe Asp Ile Asp Gly Val Leu Met Gln Ser Lys
                20                  25                  30

Asn Pro Ile Leu Pro Tyr Ala Arg Asp Thr Leu Thr Leu Leu Gln Asp
                35                  40                  45

His Lys Ile Pro Phe Val Leu Leu Thr Asn Gly Gly Gly Gln Thr Glu
        50                  55                  60

Ala Ser Arg Val Ser Phe Leu Asn Lys Ser Leu Ser Leu Lys Asn Pro
65                  70                  75                  80

Leu Arg Thr Ser Gln Ile Val Leu Ser His Thr Pro Met Arg Asn Leu
                85                  90                  95

Thr Gly Lys Tyr Asn Arg Val Leu Val Val Gly Gly Asp Asp Pro Gln
                100                 105                 110

Thr Arg Glu Val Ala Gln Ser Tyr Gly Phe Gln Glu Val Ile Arg Pro
                115                 120                 125

Ile Asp Ile Val Arg Glu Ala Pro Asn Ile Trp Pro Phe Ile Arg Tyr
130                 135                 140

Thr Arg Glu Glu Ile Gln Ala Leu Ser Lys Pro Val Asp Leu Arg Gln
145                 150                 155                 160

Pro Ile Asp Ala Ala Phe Val Phe Asn Asp Pro Arg Asp Met Gly Thr
                165                 170                 175

Asp Thr Gln Ile Val Ile Asp Ala Leu Cys Ser Glu Asn Gly Val Leu
                180                 185                 190

Gly Thr Arg Arg Gly Ile Gly Ser Ser Lys Pro Ser Val Pro Ile Ile
                195                 200                 205
```

```
Phe Ser Asn Met Asp Leu Leu Trp Ser Thr Gly Tyr Pro Ile Pro Arg
        210                 215                 220

Phe Gly Gln Gly Ala Phe Arg Leu Thr Ile Arg Glu Leu Tyr Lys Gln
225                 230                 235                 240

Leu Asn Asn Ala Glu Leu Glu Asp Ile Val Leu Gly Lys Pro Trp Pro
                245                 250                 255

Val Ser Tyr Thr Tyr Ala Glu Asn Val Leu Asn Asp Glu Trp Lys Leu
            260                 265                 270

Leu Asn Gly Asp Arg Ser Gly Ala Asn Glu Ile Pro Glu Leu Gly Val
        275                 280                 285

Lys Pro Lys Glu Gln Leu Val Glu Asn Val Tyr Met Val Gly Asp Asn
290                 295                 300

Pro Gln Ser Asp Ile Ser Gly Gly Asn Asn Tyr Gly Trp Glu Thr Ile
305                 310                 315                 320

Leu Val Glu Thr Gly Val Tyr Lys Glu Gly Asp Phe His Lys Tyr Pro
                325                 330                 335

Thr Leu Ala Lys Pro Thr Phe Gly Ile Phe Pro Asn Val Trp Asp Gly
            340                 345                 350

Val Thr Ser Ala Leu Lys Arg His Gln Val
        355                 360

<210> SEQ ID NO 13
<211> LENGTH: 352
<212> TYPE: PRT
<213> ORGANISM: Saccharomyces cerevisiae

<400> SEQUENCE: 13

Met Ile Gly Lys Arg Phe Phe Gln Thr Thr Ser Lys Lys Ile Ala Phe
1               5                   10                  15

Ala Phe Asp Ile Asp Gly Val Leu Phe Arg Gly Lys Lys Pro Ile Ala
            20                  25                  30

Gly Ala Ser Asp Ala Leu Lys Leu Leu Asn Arg Asn Lys Ile Pro Tyr
        35                  40                  45

Ile Leu Leu Thr Asn Gly Gly Gly Phe Ser Glu Arg Ala Arg Thr Glu
50                  55                  60

Phe Ile Ser Ser Lys Leu Asp Val Asp Val Ser Pro Leu Gln Ile Ile
65                  70                  75                  80

Gln Ser His Thr Pro Tyr Lys Ser Leu Val Asn Lys Tyr Ser Arg Ile
                85                  90                  95

Leu Ala Val Gly Thr Pro Ser Val Arg Gly Val Ala Glu Gly Tyr Gly
            100                 105                 110

Phe Gln Asp Val Val His Gln Thr Asp Ile Val Arg Tyr Asn Arg Asp
        115                 120                 125

Ile Ala Pro Phe Ser Gly Leu Ser Asp Glu Gln Val Met Glu Tyr Ser
130                 135                 140

Arg Asp Ile Pro Asp Leu Thr Thr Lys Lys Phe Asp Ala Val Leu Val
145                 150                 155                 160

Phe Asn Asp Pro His Asp Trp Ala Ala Asp Ile Gln Ile Ile Ser Asp
                165                 170                 175

Ala Ile Asn Ser Glu Asn Gly Met Leu Asn Thr Leu Arg Asn Glu Lys
            180                 185                 190

Ser Gly Lys Pro Ser Ile Pro Ile Tyr Phe Ser Asn Gln Asp Leu Leu
        195                 200                 205

Trp Ala Asn Pro Tyr Lys Leu Asn Arg Phe Gly Gln Gly Ala Phe Arg
210                 215                 220
```

```
Leu Leu Val Arg Arg Leu Tyr Leu Glu Leu Asn Gly Glu Pro Leu Gln
225                 230                 235                 240

Asp Tyr Thr Leu Gly Lys Pro Thr Lys Leu Thr Tyr Asp Phe Ala His
            245                 250                 255

His Val Leu Ile Asp Trp Glu Lys Arg Leu Ser Gly Lys Ile Gly Gln
            260                 265                 270

Ser Val Lys Gln Lys Leu Pro Leu Gly Thr Lys Pro Ser Thr Ser
        275                 280                 285

Pro Phe His Ala Val Phe Met Val Gly Asp Asn Pro Ala Ser Asp Ile
290                 295                 300

Ile Gly Ala Gln Asn Tyr Gly Trp Asn Ser Cys Leu Val Lys Thr Gly
305                 310                 315                 320

Val Tyr Asn Glu Gly Asp Asp Leu Lys Glu Cys Lys Pro Thr Leu Ile
            325                 330                 335

Val Asn Asp Val Phe Asp Ala Val Thr Lys Thr Leu Glu Lys Tyr Ala
            340                 345                 350

<210> SEQ ID NO 14
<211> LENGTH: 249
<212> TYPE: PRT
<213> ORGANISM: Pichia kudriavzevii

<400> SEQUENCE: 14

Met Val His Lys Leu Ile Leu Val Arg His Gly Gln Ser Glu Trp Asn
1               5                   10                  15

Glu Lys Asn Leu Phe Thr Gly Trp Val Asp Val Lys Leu Ser Glu Lys
            20                  25                  30

Gly Arg Gln Glu Ala Val Arg Ala Gly Glu Leu Leu Lys Glu Ala Asp
        35                  40                  45

Ile Lys Pro Asp Val Leu Tyr Thr Ser Leu Leu Thr Arg Ala Ile Gln
    50                  55                  60

Thr Ala Asn Ile Ala Leu Glu Asn Ala Asp Arg Leu His Ile Pro Val
65                  70                  75                  80

Val Arg Ser Trp Arg Leu Asn Glu Arg His Tyr Gly Ala Leu Gln Gly
                85                  90                  95

Lys Asp Lys Ala Gln Thr Leu Glu Thr Tyr Gly Pro Glu Lys Phe Gln
            100                 105                 110

Gln Trp Arg Arg Ser Phe Asp Ile Pro Pro Pro Ile Glu Asp His
        115                 120                 125

Ser Glu Phe Ser Gln Phe Gly Glu Glu Arg Tyr Ser Asn Val Asp Pro
    130                 135                 140

Asn Val Leu Pro Lys Thr Glu Ser Leu Ala Leu Val Ile Asp Arg Leu
145                 150                 155                 160

Leu Pro Phe Trp Gln Asp Val Ile Ala Lys Asp Leu Leu Ala Asn Lys
                165                 170                 175

Thr Val Ile Ile Thr Ala His Gly Asn Ser Leu Arg Gly Leu Val Lys
            180                 185                 190

His Leu Asp Asn Ile Ser Asp Asp Ile Ala Gly Leu Asn Ile Pro
        195                 200                 205

Thr Ala Ile Pro Leu Val Tyr Glu Leu Asp Asp Asn Leu Lys Pro Ile
    210                 215                 220

Lys Pro Ala Tyr Tyr Leu Asp Pro Glu Ala Ala Ala Gly Ala Ala
225                 230                 235                 240

Ala Val Ala Ala Gln Gly Gln Lys Lys
```

```
                        245

<210> SEQ ID NO 15
<211> LENGTH: 469
<212> TYPE: PRT
<213> ORGANISM: Saccharomyces cerevisiae

<400> SEQUENCE: 15

Met Thr Ser Ile Asp Ile Asn Asn Leu Gln Asn Thr Phe Gln Gln Ala
1               5                   10                  15

Met Asn Met Ser Gly Ser Pro Gly Ala Val Cys Thr Ser Pro Thr Gln
            20                  25                  30

Ser Phe Met Asn Thr Val Pro Gln Arg Leu Asn Ala Val Lys His Pro
        35                  40                  45

Lys Ile Leu Lys Pro Phe Ser Thr Gly Asp Met Lys Ile Leu Leu Leu
    50                  55                  60

Glu Asn Val Asn Gln Thr Ala Ile Thr Ile Phe Glu Glu Gln Gly Tyr
65                  70                  75                  80

Gln Val Glu Phe Tyr Lys Ser Ser Leu Pro Glu Glu Leu Ile Glu
                85                  90                  95

Lys Ile Lys Asp Val His Ala Ile Gly Ile Arg Ser Lys Thr Arg Leu
            100                 105                 110

Thr Ser Asn Val Leu Gln His Ala Lys Asn Leu Val Cys Ile Gly Cys
        115                 120                 125

Phe Cys Ile Gly Thr Asn Gln Val Asp Leu Asp Tyr Ala Thr Ser Arg
    130                 135                 140

Gly Ile Ala Val Phe Asn Ser Pro Phe Ser Asn Ser Arg Ser Val Ala
145                 150                 155                 160

Glu Leu Val Ile Ala Glu Ile Ile Ser Leu Ala Arg Gln Leu Gly Asp
                165                 170                 175

Arg Ser Ile Glu Leu His Thr Gly Thr Trp Asn Lys Val Ala Ala Arg
            180                 185                 190

Cys Trp Glu Val Arg Gly Lys Thr Leu Gly Ile Ile Gly Tyr Gly His
        195                 200                 205

Ile Gly Ser Gln Leu Ser Val Leu Ala Glu Ala Met Gly Leu His Val
    210                 215                 220

Leu Tyr Tyr Asp Ile Val Thr Ile Met Ala Leu Gly Thr Ala Arg Gln
225                 230                 235                 240

Val Ser Thr Leu Asp Glu Leu Leu Asn Lys Ser Asp Phe Val Thr Leu
                245                 250                 255

His Val Pro Ala Thr Pro Glu Thr Glu Lys Met Leu Ser Ala Pro Gln
            260                 265                 270

Phe Ala Ala Met Lys Asp Gly Ala Tyr Val Ile Asn Ala Ser Arg Gly
        275                 280                 285

Thr Val Val Asp Ile Pro Ser Leu Ile Gln Ala Val Lys Ala Asn Lys
    290                 295                 300

Ile Ala Gly Ala Ala Leu Asp Val Tyr Pro His Glu Pro Ala Lys Asn
305                 310                 315                 320

Gly Glu Gly Ser Phe Asn Asp Glu Leu Asn Ser Trp Thr Ser Glu Leu
                325                 330                 335

Val Ser Leu Pro Asn Ile Ile Leu Thr Pro His Ile Gly Gly Ser Thr
            340                 345                 350

Glu Glu Ala Gln Ser Ser Ile Gly Ile Glu Val Ala Thr Ala Leu Ser
        355                 360                 365
```

```
Lys Tyr Ile Asn Glu Gly Asn Ser Val Gly Ser Val Asn Phe Pro Glu
    370                 375                 380

Val Ala Leu Lys Ser Leu Ser Tyr Asp Gln Glu Asn Thr Val Arg Val
385                 390                 395                 400

Leu Tyr Ile His Gln Asn Val Pro Gly Val Leu Lys Thr Val Asn Asp
            405                 410                 415

Ile Leu Ser Asn His Asn Ile Glu Lys Gln Phe Ser Asp Ser Asn Gly
        420                 425                 430

Glu Ile Ala Tyr Leu Met Ala Asp Ile Ser Ser Val Asp Gln Ser Asp
                435                 440                 445

Ile Lys Asp Ile Tyr Glu Gln Leu Asn Gln Thr Ser Ala Lys Ile Ser
    450                 455                 460

Ile Arg Leu Leu Tyr
465

<210> SEQ ID NO 16
<211> LENGTH: 381
<212> TYPE: PRT
<213> ORGANISM: Escherichia coli

<400> SEQUENCE: 16

Met Lys Ile Val Ile Ala Pro Asp Ser Phe Lys Glu Ser Leu Ser Ala
1               5                   10                  15

Glu Lys Cys Cys Gln Ala Ile Lys Ala Gly Phe Ser Thr Leu Phe Pro
            20                  25                  30

Asp Ala Asn Tyr Ile Cys Leu Pro Ile Ala Asp Gly Gly Glu Gly Thr
        35                  40                  45

Val Asp Ala Met Val Ala Ala Thr Gly Gly Asn Ile Val Thr Leu Glu
    50                  55                  60

Val Cys Gly Pro Met Gly Glu Lys Val Asn Ala Phe Tyr Gly Leu Thr
65                  70                  75                  80

Gly Asp Gly Lys Thr Ala Val Ile Glu Met Ala Ala Ala Ser Gly Leu
                85                  90                  95

Met Leu Val Ala Pro Glu Lys Arg Asn Pro Leu Leu Ala Ser Ser Phe
            100                 105                 110

Gly Thr Gly Glu Leu Ile Arg His Ala Leu Asp Asn Asp Ile Arg His
        115                 120                 125

Ile Ile Leu Gly Ile Gly Gly Ser Ala Thr Val Asp Gly Gly Met Gly
    130                 135                 140

Met Ala Gln Ala Leu Gly Val Arg Phe Leu Asp Ala Asp Gly Gln Ala
145                 150                 155                 160

Leu Ala Ala Asn Gly Gly Asn Leu Ala Arg Val Ala Ser Ile Glu Met
                165                 170                 175

Asp Glu Cys Asp Pro Arg Leu Ala Asn Cys His Ile Glu Val Ala Cys
            180                 185                 190

Asp Val Asp Asn Pro Leu Val Gly Ala Arg Gly Ala Ala Ala Val Phe
        195                 200                 205

Gly Pro Gln Lys Gly Ala Thr Pro Glu Met Val Glu Glu Leu Glu Gln
    210                 215                 220

Gly Leu Gln Asn Tyr Ala Arg Val Leu Gln Gln Thr Glu Ile Asn
225                 230                 235                 240

Val Cys Gln Met Ala Gly Gly Ala Ala Gly Gly Met Gly Ile Ala
                245                 250                 255

Ala Ala Val Phe Leu Asn Ala Asp Ile Lys Pro Gly Ile Glu Ile Val
            260                 265                 270
```

```
Leu Asn Ala Val Asn Leu Ala Gln Ala Val Gln Gly Ala Ala Leu Val
            275                 280                 285

Ile Thr Gly Glu Gly Arg Ile Asp Ser Gln Thr Ala Gly Gly Lys Ala
        290                 295                 300

Pro Leu Gly Val Ala Ser Val Ala Lys Gln Phe Asn Val Pro Val Ile
305                 310                 315                 320

Gly Ile Ala Gly Val Leu Gly Asp Gly Val Glu Val Val His Gln Tyr
                325                 330                 335

Gly Ile Asp Ala Val Phe Ser Ile Leu Pro Arg Leu Ala Pro Leu Ala
            340                 345                 350

Glu Val Leu Ala Ser Gly Glu Thr Asn Leu Phe Asn Ser Ala Arg Asn
        355                 360                 365

Ile Ala Cys Ala Ile Lys Ile Gly Gln Gly Ile Lys Asn
        370                 375                 380

<210> SEQ ID NO 17
<211> LENGTH: 486
<212> TYPE: PRT
<213> ORGANISM: Artificial Sequence
<220> FEATURE:
<223> OTHER INFORMATION: Synthetic Sequence

<400> SEQUENCE: 17

Met Ser Ser Pro Gln Asp Ile Asn Asn Leu Gln Asn Asp Leu Leu Ala
1               5                   10                  15

Arg Ala Arg Ser Phe Gln Gln Ala Leu Asn Leu Ser Gly Ser Pro Gly
            20                  25                  30

Asn Ala Val Ser Thr Ser Pro Pro Thr Ser Phe Gly Gly Ser Phe Met
        35                  40                  45

Asn Gln Leu Pro Arg Arg Leu Ser Arg Thr Ala Ala Ser Lys Pro Ala
    50                  55                  60

Lys Ala Leu Lys Pro Phe Ser Thr Gly Asp Ile Lys Ile Leu Leu Leu
65                  70                  75                  80

Glu Asn Val Asn Gln Thr Ala Arg Asp Ile Phe Lys Glu Gln Gly Tyr
                85                  90                  95

Gln Val Glu Phe Leu Lys Ser Ser Leu Pro Glu Asp Glu Leu Ile Glu
            100                 105                 110

Lys Ile Arg Asp Val His Ala Ile Gly Ile Arg Ser Lys Thr Lys Leu
        115                 120                 125

Thr Ala Lys Val Leu Lys His Ala Lys Asn Leu Ile Val Ile Gly Cys
    130                 135                 140

Phe Cys Ile Gly Thr Asn Gln Val Asp Leu Glu Tyr Ala Ala Lys His
145                 150                 155                 160

Gly Ile Ala Val Phe Asn Ser Pro Phe Ser Asn Ser Arg Ser Val Ala
                165                 170                 175

Glu Leu Val Ile Ala Glu Ile Ser Leu Ala Arg Gln Leu Gly Asp
            180                 185                 190

Arg Ser Ile Glu Met His Thr Gly Thr Trp Asn Lys Val Ser Ala Lys
        195                 200                 205

Cys Trp Glu Ile Arg Gly Lys Thr Leu Gly Ile Gly Tyr Gly His
210                 215                 220

Ile Gly Ser Gln Leu Ser Val Leu Ala Glu Ala Met Gly Met Asn Val
225                 230                 235                 240

Ile Tyr Tyr Asp Val Val Thr Ile Met Ala Leu Gly Thr Ala Lys Gln
                245                 250                 255
```

Val Pro Thr Leu Asp Glu Leu Leu Asn Lys Ala Asp Phe Val Thr Leu
            260                 265                 270

His Val Pro Glu Thr Pro Glu Thr Lys Asn Met Ile Ser Ala Pro Gln
            275                 280                 285

Phe Ala Ala Met Lys Asp Gly Ala Tyr Leu Ile Asn Ala Ser Arg Gly
290                 295                 300

Thr Val Val Asp Ile Pro Ala Leu Ile Gln Ala Met Lys Ser Gly Lys
305                 310                 315                 320

Ile Ala Gly Ala Ala Leu Asp Val Tyr Pro Asn Glu Pro Ala Lys Asn
                325                 330                 335

Gly Asp Gly Tyr Phe Asn Asp Leu Asn Ser Trp Ala Ser Glu Leu
                340                 345                 350

Arg Ser Leu Lys Asn Val Ile Leu Thr Pro His Ile Gly Gly Ser Thr
                355                 360                 365

Glu Glu Ala Gln Ser Ala Ile Gly Val Glu Val Ala Thr Ala Leu Val
            370                 375                 380

Lys Tyr Ile Asn Glu Gly Asn Ser Leu Gly Ala Val Asn Phe Pro Glu
385                 390                 395                 400

Val Ser Leu Arg Ser Leu Thr Leu Asp Gln Pro Asn His Val Arg Val
                405                 410                 415

Leu Tyr Ile His Gln Asn Val Pro Gly Val Leu Arg Thr Val Asn Glu
                420                 425                 430

Ile Leu Ser Asn His Asn Ile Glu Lys Gln Phe Ser Asp Ser Arg Gly
                435                 440                 445

Asp Ile Ala Tyr Leu Met Ala Asp Ile Ser Asp Val Asp Gln Ser Asp
            450                 455                 460

Ile Lys Asp Leu Tyr Glu Gln Leu Glu Gln Thr Ser Ser Lys Ile Ser
465                 470                 475                 480

Thr Arg Leu Leu Tyr Leu
                485

<210> SEQ ID NO 18
<211> LENGTH: 381
<212> TYPE: PRT
<213> ORGANISM: Escherichia coli

<400> SEQUENCE: 18

Met Lys Ile Val Ile Ala Pro Asp Ser Tyr Lys Glu Ser Leu Ser Ala
1               5                   10                  15

Ser Glu Val Ala Gln Ala Ile Glu Lys Gly Phe Arg Glu Ile Phe Pro
            20                  25                  30

Asp Ala Gln Tyr Val Ser Val Pro Val Ala Asp Gly Gly Glu Gly Thr
        35                  40                  45

Val Glu Ala Met Ile Ala Ala Thr Gln Gly Ala Glu Arg His Ala Trp
    50                  55                  60

Val Thr Gly Pro Leu Gly Glu Lys Val Asn Ala Ser Trp Gly Ile Ser
65                  70                  75                  80

Gly Asp Gly Lys Thr Ala Phe Ile Glu Met Ala Ala Ala Ser Gly Leu
                85                  90                  95

Glu Leu Val Pro Ala Glu Lys Arg Asp Pro Leu Val Thr Thr Ser Arg
            100                 105                 110

Gly Thr Gly Glu Leu Ile Leu Gln Ala Leu Glu Ser Gly Ala Thr Asn
        115                 120                 125

Ile Ile Ile Gly Ile Gly Gly Ser Ala Thr Asn Asp Gly Gly Ala Gly

```
                    130                 135                 140
Met Val Gln Ala Leu Gly Ala Lys Leu Cys Asp Ala Asn Gly Asn Glu
145                 150                 155                 160

Ile Gly Phe Gly Gly Gly Ser Leu Asn Thr Leu Asn Asp Ile Asp Ile
                165                 170                 175

Ser Gly Leu Asp Pro Arg Leu Lys Asp Cys Val Ile Arg Val Ala Cys
                180                 185                 190

Asp Val Thr Asn Pro Leu Val Gly Asp Asn Gly Ala Ser Arg Ile Phe
                195                 200                 205

Gly Pro Gln Lys Gly Ala Ser Glu Ala Met Ile Val Glu Leu Asp Asn
                210                 215                 220

Asn Leu Ser His Tyr Ala Glu Val Ile Lys Lys Ala Leu His Val Asp
225                 230                 235                 240

Val Lys Asp Val Pro Gly Ala Gly Ala Ala Gly Gly Met Gly Ala Ala
                245                 250                 255

Leu Met Ala Phe Leu Gly Ala Glu Leu Lys Ser Gly Ile Glu Ile Val
                260                 265                 270

Thr Thr Ala Leu Asn Leu Glu Glu His Ile His Asp Cys Thr Leu Val
                275                 280                 285

Ile Thr Gly Glu Gly Arg Ile Asp Ser Gln Ser Ile His Gly Lys Val
                290                 295                 300

Pro Ile Gly Val Ala Asn Val Ala Lys Lys Tyr His Lys Pro Val Ile
305                 310                 315                 320

Gly Ile Ala Gly Ser Leu Thr Asp Asp Val Gly Val Val His Gln His
                325                 330                 335

Gly Ile Asp Ala Val Phe Ser Val Leu Thr Ser Ile Gly Thr Leu Asp
                340                 345                 350

Glu Ala Phe Arg Gly Ala Tyr Asp Asn Ile Cys Arg Ala Ser Arg Asn
                355                 360                 365

Ile Ala Ala Thr Leu Ala Ile Gly Met Arg Asn Ala Gly
        370                 375                 380

<210> SEQ ID NO 19
<211> LENGTH: 388
<212> TYPE: PRT
<213> ORGANISM: Pichia kudriavzevii

<400> SEQUENCE: 19

Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
                20                  25                  30

His Pro Phe Lys Val Thr Val Val Gly Ser Gly Asn Trp Gly Cys Thr
                35                  40                  45

Ile Ala Lys Val Ile Ala Glu Asn Thr Val Glu Arg Pro Arg Gln Phe
        50                  55                  60

Gln Arg Asp Val Asn Met Trp Val Tyr Glu Glu Leu Ile Glu Gly Glu
65                  70                  75                  80

Lys Leu Thr Glu Ile Ile Asn Thr Lys His Glu Asn Val Lys Tyr Leu
                85                  90                  95

Pro Gly Ile Lys Leu Pro Val Asn Val Ala Val Pro Asp Ile Val
                100                 105                 110

Glu Ala Cys Ala Gly Ser Asp Leu Ile Val Phe Asn Ile Pro His Gln
                115                 120                 125
```

Phe Leu Pro Arg Ile Leu Ser Gln Leu Lys Gly Lys Val Asn Pro Lys
    130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285

Ala Ala Thr Phe Thr His Glu Ser Ala Gly Val Ala Asp Leu Ile Thr
290                 295                 300

Thr Cys Ala Gly Gly Arg Asn Val Arg Val Gly Arg Tyr Met Ala Gln
305                 310                 315                 320

His Ser Val Ser Ala Thr Glu Ala Glu Glu Lys Leu Leu Asn Gly Gln
                325                 330                 335

Ser Cys Gln Gly Ile His Thr Thr Arg Glu Val Tyr Glu Phe Leu Ser
            340                 345                 350

Asn Met Gly Arg Thr Asp Glu Phe Pro Leu Phe Thr Thr Thr Tyr Arg
        355                 360                 365

Ile Ile Tyr Glu Asn Phe Pro Ile Glu Lys Leu Pro Glu Cys Leu Glu
370                 375                 380

Pro Val Glu Asp
385

<210> SEQ ID NO 20
<211> LENGTH: 563
<212> TYPE: PRT
<213> ORGANISM: Pichia kudriavzevii

<400> SEQUENCE: 20

Met Ile Pro Arg Leu Asn Pro Leu Leu Asn Ile Ser His Leu Arg Gly
1               5                   10                  15

Gly Pro Lys Phe Ile Gly Lys Ala Ile Lys Pro Ser Gln Phe Glu Phe
            20                  25                  30

Arg Lys Asn Asn Phe Arg Phe Asn Ser Thr Ser Thr Lys Thr Gly Ser
        35                  40                  45

Ala Arg Thr Ile Lys Ser Gly Phe Leu Ser Trp Ser Phe Arg Ala Ala
50                  55                  60

Thr Phe Thr Gly Ile Ala Gly Trp Leu Tyr Leu Thr Tyr Leu Val Tyr
65                  70                  75                  80

Lys Glu Thr Asn Pro Gly Ser Gln Ser Pro Gln Thr Glu Phe Ser Glu
                85                  90                  95

Ile Gly Asn Lys Lys Lys Asn Ile Val Ile Leu Gly Ser Gly Trp Gly
            100                 105                 110

```
Ala Val Ser Val Leu Lys Thr Leu Asp Thr Thr Lys Tyr Asn Val Thr
        115                 120                 125

Ile Val Ser Pro Arg Asn Tyr Phe Leu Phe Thr Pro Leu Leu Pro Ser
130                 135                 140

Val Pro Ser Gly Thr Ile Asp Ile Lys Ser Ile Cys Asp Ser Ile Arg
145                 150                 155                 160

Thr Ile Ala Arg Gln Thr Pro Gly Glu Val Thr Tyr Leu Glu Ala Ala
                165                 170                 175

Ala Thr Asp Ile Asp Pro Val Lys Lys Thr Ile Lys Leu Glu His Lys
                180                 185                 190

Ser Gln Arg Phe Leu Ile Gly Asp Ala Phe Thr Ser Glu Gly Asp Val
        195                 200                 205

Ile Glu Asn Glu Leu Ser Tyr Asp Tyr Leu Val Tyr Ala Val Gly Ala
        210                 215                 220

Thr Val Asn Thr Phe Gly Ile Pro Gly Ile Pro Glu Tyr Ala Ser Tyr
225                 230                 235                 240

Leu Lys Glu Ala Asn Asp Ala Thr Ala Val Arg Gln Lys Leu Phe Asn
                245                 250                 255

Gln Ile Glu Ala Ser Arg Leu Leu Pro Lys Asp Ser Gly Asp Arg Lys
                260                 265                 270

Arg Leu Leu Ser Phe Val Val Cys Gly Gly Pro Thr Gly Val Glu
        275                 280                 285

Leu Ala Ala Glu Ile Lys Asp Tyr Ile Asp Gln Asp Leu Cys Lys Phe
        290                 295                 300

Ile Pro Gly Ile Glu Lys Glu Met Gln Val Thr Leu Ile Glu Ala Gln
305                 310                 315                 320

His Asn Val Leu Ser Met Phe His Pro Lys Leu Ile Glu Tyr Thr Lys
                325                 330                 335

Glu Val Phe Lys Gln Gln Asn Leu His Leu Gln Val Asp Thr Met Val
                340                 345                 350

Lys Lys Val Asp Asp Lys Asn Val Tyr Ala Thr Tyr Arg His Pro Asp
        355                 360                 365

Gly Lys Thr Glu Asp Met Val Ile Pro Tyr Gly Thr Leu Val Trp Ala
        370                 375                 380

Gly Gly Asn Ala Gln Arg Lys Leu Thr Arg Asp Leu Ser Ser Lys Ile
385                 390                 395                 400

Ile Glu Gln Lys Thr Ala Arg Arg Gly Leu Leu Val Asp Glu Tyr Leu
                405                 410                 415

Lys Leu Asp Gly Asp Asp Ser Ile Tyr Ala Ile Gly Asp Cys Thr Phe
                420                 425                 430

Thr Pro Asn Pro Pro Thr Ala Gln Val Ala His Gln Gln Gly Glu Tyr
        435                 440                 445

Leu Gly Glu His Phe Asn Lys Leu Ala Lys Ile Asp Glu Leu Asn Tyr
        450                 455                 460

Leu Ile Thr Asn Ser Thr Asp Asp Ser Thr Lys Tyr Ser Lys Arg Leu
465                 470                 475                 480

Glu Arg Ala Glu Lys Ala Ile Lys Pro Phe Glu Tyr Asp His Gln Gly
                485                 490                 495

Ala Leu Ala Tyr Val Gly Ser Glu Arg Ala Val Ala Asp Leu His Trp
                500                 505                 510

Gly Ser Trp Ser Thr Val Ala Leu Gly Gly Thr Met Thr Phe Phe Phe
        515                 520                 525
```

-continued

Trp Arg Thr Ala Tyr Val Ser Met Leu Leu Ser Ile Arg Asn Lys Ile
    530                 535                 540

Leu Val Val Thr Asp Trp Val Lys Val Ala Ile Phe Gly Arg Asp Cys
545                 550                 555                 560

Ser Gln Glu

<210> SEQ ID NO 21
<211> LENGTH: 446
<212> TYPE: PRT
<213> ORGANISM: Lactococcus lactis

<400> SEQUENCE: 21

Met Lys Ile Val Val Ile Gly Thr Asn His Ala Gly Ile Ala Thr Ala
1               5                   10                  15

Asn Thr Leu Ile Asp Arg Tyr Pro Gly His Glu Ile Val Met Ile Asp
                20                  25                  30

Arg Asn Ser Asn Met Ser Tyr Leu Gly Cys Gly Thr Ala Ile Trp Val
            35                  40                  45

Gly Arg Gln Ile Glu Lys Pro Asp Glu Leu Phe Tyr Ala Lys Ala Glu
    50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Asp Leu Lys Gly Ile His
    115                 120                 125

Phe Leu Lys Leu Phe Gln Glu Gly Gln Ala Ile Asp Glu Glu Phe Ala
130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
    195                 200                 205

Phe Gly Glu Leu Ala Gln Glu Phe Lys Ala Asn Glu Lys Gly His Val
210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asp Lys His Gln Gln Ser
            260                 265                 270

Ser Asp Pro Asp Val Ser Ala Val Gly Asp Val Ala Thr Ile Tyr Ser
    275                 280                 285

Asn Ala Leu Gln Asp Phe Thr Tyr Ile Ala Leu Ala Ser Asn Ala Val
290                 295                 300

Arg Ser Gly Ile Val Ala Gly His Asn Ile Gly Gly Lys Ser Ile Glu
305                 310                 315                 320

Ser Val Gly Val Gln Gly Ser Asn Gly Ile Ser Ile Phe Gly Tyr Asn
                325                 330                 335

```
Met Thr Ser Thr Gly Leu Ser Val Lys Ala Ala Lys Lys Ile Gly Leu
                340                 345                 350

Glu Val Ser Phe Ser Asp Phe Glu Asp Lys Gln Lys Ala Trp Phe Leu
            355                 360                 365

His Glu Asn Asn Asp Ser Val Lys Ile Arg Ile Val Tyr Glu Thr Lys
        370                 375                 380

Asn Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415

Ile Asp Glu Leu Ala Leu Leu Asp Leu Phe Phe Leu Pro His Phe Asn
            420                 425                 430

Ser Pro Tyr Asn Tyr Met Thr Val Ala Ala Leu Asn Ala Lys
        435                 440                 445

<210> SEQ ID NO 22
<211> LENGTH: 1511
<212> TYPE: PRT
<213> ORGANISM: Saccharomyces cerevisiae

<400> SEQUENCE: 22

Met Ser Ser Thr Asp Glu His Ile Glu Lys Asp Ile Ser Ser Arg Ser
1               5                   10                  15

Asn His Asp Asp Asp Tyr Ala Asn Ser Val Gln Ser Tyr Ala Ala Ser
            20                  25                  30

Glu Gly Gln Val Asp Asn Glu Asp Leu Ala Ala Thr Ser Gln Leu Ser
        35                  40                  45

Arg His Leu Ser Asn Ile Leu Ser Asn Glu Glu Gly Ile Glu Arg Leu
    50                  55                  60

Glu Ser Met Ala Arg Val Ile Ser His Lys Thr Lys Lys Glu Met Asp
65                  70                  75                  80

Ser Phe Glu Ile Asn Asp Leu Asp Phe Asp Leu Arg Ser Leu Leu His
                85                  90                  95

Tyr Leu Arg Ser Arg Gln Leu Glu Gln Gly Ile Glu Pro Gly Asp Ser
            100                 105                 110

Gly Ile Ala Phe Lys Asn Leu Thr Ala Val Gly Val Asp Ala Ser Ala
        115                 120                 125

Ala Tyr Gly Pro Ser Val Glu Glu Met Phe Arg Asn Ile Ala Ser Ile
    130                 135                 140

Pro Ala His Leu Ile Ser Lys Phe Thr Lys Lys Ser Asp Val Pro Leu
145                 150                 155                 160

Arg Asn Ile Ile Gln Asn Cys Thr Gly Val Val Glu Ser Gly Glu Met
                165                 170                 175

Leu Phe Val Val Gly Arg Pro Gly Ala Gly Cys Ser Thr Phe Leu Lys
            180                 185                 190

Cys Leu Ser Gly Glu Thr Ser Glu Leu Val Asp Val Gln Gly Glu Phe
        195                 200                 205

Ser Tyr Asp Gly Leu Asp Gln Ser Glu Met Met Ser Lys Tyr Lys Gly
    210                 215                 220

Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Val
                245                 250                 255

Arg Ile Asp Lys Met Thr Arg Lys Gln Tyr Val Asp Asn Ile Arg Asp
            260                 265                 270
```

```
Met Trp Cys Thr Val Phe Gly Leu Arg His Thr Tyr Ala Thr Lys Val
        275                 280                 285

Gly Asn Asp Phe Val Arg Gly Val Ser Gly Gly Glu Arg Lys Arg Val
    290                 295                 300

Ser Leu Val Glu Ala Gln Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
                325                 330                 335

Ala Ile Arg Thr Ala Thr Asn Met Val Asn Asn Ser Ala Ile Val Ala
                340                 345                 350

Ile Tyr Gln Ala Gly Glu Asn Ile Tyr Glu Leu Phe Asp Lys Thr Thr
            355                 360                 365

Val Leu Tyr Asn Gly Arg Gln Ile Tyr Phe Gly Pro Ala Asp Lys Ala
    370                 375                 380

Val Gly Tyr Phe Gln Arg Met Gly Trp Val Lys Pro Asn Arg Met Thr
385                 390                 395                 400

Ser Ala Glu Phe Leu Thr Ser Val Thr Val Asp Phe Glu Asn Arg Thr
                405                 410                 415

Leu Asp Ile Lys Pro Gly Tyr Glu Asp Lys Val Pro Lys Ser Ser Ser
            420                 425                 430

Glu Phe Glu Glu Tyr Trp Leu Asn Ser Glu Asp Tyr Gln Glu Leu Leu
    435                 440                 445

Arg Thr Tyr Asp Asp Tyr Gln Ser Arg His Pro Val Asn Glu Thr Arg
    450                 455                 460

Asp Arg Leu Asp Val Ala Lys Lys Gln Arg Leu Gln Gln Gly Gln Arg
465                 470                 475                 480

Glu Asn Ser Gln Tyr Val Val Asn Tyr Trp Thr Gln Val Tyr Tyr Cys
                485                 490                 495

Met Ile Arg Gly Phe Gln Arg Val Lys Gly Asp Ser Thr Tyr Thr Lys
                500                 505                 510

Val Tyr Leu Ser Ser Phe Leu Ile Lys Ala Leu Ile Ile Gly Ser Met
            515                 520                 525

Phe His Lys Ile Asp Asp Lys Ser Gln Ser Thr Thr Ala Gly Ala Tyr
    530                 535                 540

Ser Arg Gly Gly Met Leu Phe Tyr Val Leu Leu Phe Ala Ser Val Thr
545                 550                 555                 560

Ser Leu Ala Glu Ile Gly Asn Ser Phe Ser Ser Arg Pro Val Ile Val
                565                 570                 575

Lys His Lys Ser Tyr Ser Met Tyr His Leu Ser Ala Glu Ser Leu Gln
                580                 585                 590

Glu Ile Ile Thr Glu Phe Pro Thr Lys Phe Val Ala Ile Val Ile Leu
            595                 600                 605

Cys Leu Ile Thr Tyr Trp Ile Pro Phe Met Lys Tyr Glu Ala Gly Ala
    610                 615                 620

Phe Phe Gln Tyr Ile Leu Tyr Leu Leu Thr Val Gln Gln Cys Thr Ser
625                 630                 635                 640

Phe Ile Phe Lys Phe Val Ala Thr Met Ser Lys Ser Gly Val Asp Ala
                645                 650                 655

His Ala Val Gly Gly Leu Trp Val Leu Met Leu Cys Val Tyr Ala Gly
                660                 665                 670

Phe Val Leu Pro Ile Gly Glu Met His His Trp Ile Arg Trp Leu His
    675                 680                 685
```

```
Phe Ile Asn Pro Leu Thr Tyr Ala Phe Glu Ser Leu Val Ser Thr Glu
    690             695                 700

Phe His His Arg Glu Met Leu Cys Ser Ala Leu Val Pro Ser Gly Pro
705             710                 715                 720

Gly Tyr Glu Gly Ile Ser Ile Ala Asn Gln Val Cys Asp Ala Ala Gly
            725                 730                 735

Ala Val Lys Gly Asn Leu Tyr Val Ser Gly Asp Ser Tyr Ile Leu His
                740                 745                 750

Gln Tyr His Phe Ala Tyr Lys His Ala Trp Arg Asn Trp Gly Val Asn
            755                 760                 765

Ile Val Trp Thr Phe Gly Tyr Ile Val Phe Asn Val Ile Leu Ser Glu
    770                 775                 780

Tyr Leu Lys Pro Val Glu Gly Gly Asp Leu Leu Tyr Lys Arg
785             790                 795                 800

Gly His Met Pro Glu Leu Gly Thr Glu Asn Ala Asp Ala Arg Thr Ala
                805                 810                 815

Ser Arg Glu Glu Met Met Glu Ala Leu Asn Gly Pro Asn Val Asp Leu
                820                 825                 830

Glu Lys Val Ile Ala Glu Lys Asp Val Phe Thr Trp Asn His Leu Asp
            835                 840                 845

Tyr Thr Ile Pro Tyr Asp Gly Ala Thr Arg Lys Leu Leu Ser Asp Val
    850                 855                 860

Phe Gly Tyr Val Lys Pro Gly Lys Met Thr Ala Leu Met Gly Glu Ser
865             870                 875                 880

Gly Ala Gly Lys Thr Thr Leu Leu Asn Val Leu Ala Gln Arg Ile Asn
                885                 890                 895

Met Gly Val Ile Thr Gly Asp Met Leu Val Asn Ala Lys Pro Leu Pro
            900                 905                 910

Ala Ser Phe Asn Arg Ser Cys Gly Tyr Val Ala Gln Ala Asp Asn His
            915                 920                 925

Met Ala Glu Leu Ser Val Arg Glu Ser Leu Arg Phe Ala Ala Glu Leu
    930                 935                 940

Arg Gln Gln Ser Ser Val Pro Leu Glu Glu Lys Tyr Glu Tyr Val Glu
945                 950                 955                 960

Lys Ile Ile Thr Leu Leu Gly Met Gln Asn Tyr Ala Glu Ala Leu Val
            965                 970                 975

Gly Lys Thr Gly Arg Gly Leu Asn Val Glu Gln Arg Lys Lys Leu Ser
            980                 985                 990

Ile Gly Val Glu Leu Val Ala Lys Pro Ser Leu Leu Leu Phe Leu Asp
    995                 1000                1005

Glu Pro Thr Ser Gly Leu Asp Ser Gln Ser Ala Trp Ser Ile Val
1010            1015                1020

Gln Phe Met Arg Ala Leu Ala Asp Ser Gly Gln Ser Ile Leu Cys
1025            1030                1035

Thr Ile His Gln Pro Ser Ala Thr Leu Phe Glu Gln Phe Asp Arg
1040            1045                1050

Leu Leu Leu Leu Lys Lys Gly Gly Lys Met Val Tyr Phe Gly Asp
1055            1060                1065

Ile Gly Pro Asn Ser Glu Thr Leu Leu Lys Tyr Phe Glu Arg Gln
1070            1075                1080

Ser Gly Met Lys Cys Gly Val Ser Glu Asn Pro Ala Glu Tyr Ile
1085            1090                1095

Leu Asn Cys Ile Gly Ala Gly Ala Thr Ala Ser Val Asn Ser Asp
```

1100				1105				1110

Trp His Asp Leu Trp Leu Ala Ser Pro Glu Cys Ala Ala Ala Arg
    1115				1120				1125

Ala Glu Val Glu Glu Leu His Arg Thr Leu Pro Gly Arg Ala Val
    1130				1135				1140

Asn Asp Asp Pro Glu Leu Ala Thr Arg Phe Ala Ala Ser Tyr Met
    1145				1150				1155

Thr Gln Ile Lys Cys Val Leu Arg Arg Thr Ala Leu Gln Phe Trp
    1160				1165				1170

Arg Ser Pro Val Tyr Ile Arg Ala Lys Phe Phe Glu Cys Val Ala
    1175				1180				1185

Cys Ala Leu Phe Val Gly Leu Ser Tyr Val Gly Val Asn His Ser
    1190				1195				1200

Val Gly Gly Ala Ile Glu Ala Phe Ser Ser Ile Phe Met Leu Leu
    1205				1210				1215

Leu Ile Ala Leu Ala Met Ile Asn Gln Leu His Val Phe Ala Tyr
    1220				1225				1230

Asp Ser Arg Glu Leu Tyr Glu Val Arg Glu Ala Ala Ser Asn Thr
    1235				1240				1245

Phe His Trp Ser Val Leu Leu Cys His Ala Ala Val Glu Asn
    1250				1255				1260

Phe Trp Ser Thr Leu Cys Gln Phe Met Cys Phe Ile Cys Tyr Tyr
    1265				1270				1275

Trp Pro Ala Gln Phe Ser Gly Arg Ala Ser His Ala Gly Phe Phe
    1280				1285				1290

Phe Phe Phe Tyr Val Leu Ile Phe Pro Leu Tyr Phe Val Thr Tyr
    1295				1300				1305

Gly Leu Trp Ile Leu Tyr Met Ser Pro Asp Val Pro Ser Ala Ser
    1310				1315				1320

Met Ile Asn Ser Asn Leu Phe Ala Ala Met Leu Leu Phe Cys Gly
    1325				1330				1335

Ile Leu Gln Pro Arg Glu Lys Met Pro Ala Phe Trp Arg Arg Leu
    1340				1345				1350

Met Tyr Asn Val Ser Pro Phe Thr Tyr Val Val Gln Ala Leu Val
    1355				1360				1365

Thr Pro Leu Val His Asn Lys Lys Val Val Cys Asn Pro His Glu
    1370				1375				1380

Tyr Asn Ile Met Asp Pro Pro Ser Gly Lys Thr Cys Gly Glu Phe
    1385				1390				1395

Leu Ser Thr Tyr Met Asp Asn Asn Thr Gly Tyr Leu Val Asn Pro
    1400				1405				1410

Thr Ala Thr Glu Asn Cys Gln Tyr Cys Pro Tyr Thr Val Gln Asp
    1415				1420				1425

Gln Val Val Ala Lys Tyr Asn Val Lys Trp Asp His Arg Trp Arg
    1430				1435				1440

Asn Phe Gly Phe Met Trp Ala Tyr Ile Cys Phe Asn Ile Ala Ala
    1445				1450				1455

Met Leu Ile Cys Tyr Tyr Val Val Arg Val Lys Val Trp Ser Leu
    1460				1465				1470

Lys Ser Val Leu Asn Phe Lys Lys Trp Phe Asn Gly Pro Arg Lys
    1475				1480				1485

Glu Arg His Glu Lys Asp Thr Asn Ile Phe Gln Thr Val Pro Gly
    1490				1495				1500

```
Asp Glu  Asn Lys Ile Thr Lys  Lys
    1505              1510

<210> SEQ ID NO 23
<211> LENGTH: 944
<212> TYPE: PRT
<213> ORGANISM: Saccharomyces cerevisiae

<400> SEQUENCE: 23

Met Asp Thr Gln Ile Ala Ile Thr Gly Val Ala Val Gly Lys Glu Ile
1               5                   10                  15

Asn Asn Asp Asn Ser Lys Thr Asp Gln Lys Val Ser Leu Pro Lys Ala
            20                  25                  30

Asp Val Pro Cys Ile Asp Lys Ala Thr Gln Thr Ile Ile Glu Gly Cys
        35                  40                  45

Ser Lys Asp Asp Pro Arg Leu Ser Tyr Pro Thr Lys Leu Glu Thr Thr
    50                  55                  60

Glu Lys Gly Lys Thr Lys Arg Asn Ser Phe Ala Cys Val Cys His
65                  70                  75                  80

Ser Leu Lys Gln Lys Cys Glu Pro Ser Asp Val Asn Asp Ile Tyr Arg
                85                  90                  95

Lys Pro Cys Arg Arg Cys Leu Lys His Lys Lys Leu Cys Lys Phe Asp
            100                 105                 110

Leu Ser Lys Arg Thr Arg Lys Arg Lys Pro Arg Ser Arg Ser Pro Thr
        115                 120                 125

Pro Phe Glu Ser Pro Met Val Asn Val Ser Thr Lys Ser Lys Gly Pro
    130                 135                 140

Thr Asp Ser Glu Glu Ser Ser Leu Lys Asp Gly Thr Ser Tyr Leu Ala
145                 150                 155                 160

Ser Phe Pro Ser Asp Pro Asn Ala Lys Gln Phe Pro Asn Ser Arg Thr
                165                 170                 175

Val Leu Pro Gly Leu Gln Gln Ser Leu Ser Asp Leu Trp Ser Thr Leu
            180                 185                 190

Ser Gln Pro Pro Ser Tyr Gly Ala Arg Glu Ala Glu Thr Thr Ser Thr
        195                 200                 205

Gly Glu Ile Thr Thr Asn Asn His Thr Lys Ser Asn Gly Ser Val Pro
    210                 215                 220

Thr Asn Pro Ala Val Leu Ala Ser Asn Asp Glu His Thr Asn Ile Ser
225                 230                 235                 240

Asp Ala Pro Val Ile Tyr Ser Thr Tyr Asn Ser Pro Val Pro Ile Ser
                245                 250                 255

Ser Ala Pro Thr Ser Ile Asn Ser Glu Ala Leu Phe Lys His Arg Pro
            260                 265                 270

Lys Ile Val Gly Asp Glu Glu Thr Gln Asn Val Lys Val Lys Arg Gln
        275                 280                 285

Lys Lys Ser Tyr Ser Arg His Met Thr Arg Ser Phe Arg Lys Gln Leu
    290                 295                 300

Gln Ser Leu Ile Ile Ser Gln Lys Gly Lys Ile Arg Asp Ile Ser Met
305                 310                 315                 320

Lys Leu Asp Thr Trp Ser Lys Gln Trp Asn Asp Leu Val Glu Lys Ser
                325                 330                 335

Met Phe Leu Pro Thr Ile Ala Asp Pro Val Ser Val Gly Ile Ile Ser
            340                 345                 350

His Glu Glu Ala Thr Leu Arg Leu His Leu Tyr Lys Thr Glu Ile Ser
```

```
              355              360              365
Tyr Leu Ser Lys Leu Pro Phe Ile Lys Val Glu Glu Asn Val Ser Val
370                     375                 380
Asp Glu Leu Arg Lys Lys Pro Ile Leu Phe Ser Val Ile Met Ser
385                 390                 395                 400
Cys Val Ser Ile Val Leu Thr Pro Lys Gln Thr Thr Arg Gly Thr Ile
                    405                 410                 415
Met Lys Leu Asp Ser Phe Val Leu Asn Leu Ile Thr Asn Gln Ile Phe
                420                 425                 430
Lys Ala Asn Asn Lys Ser Ile Glu Ile Ile Glu Ser Leu Ser Thr Leu
            435                 440                 445
Cys Leu Trp Tyr Asn Phe Phe Glu Trp Ser Ser Lys Thr Arg Tyr His
450                 455                 460
Ile Phe Asn Tyr Ile Cys Cys Cys Leu Thr Arg Asp Leu Gly Pro Thr
465                 470                 475                 480
Tyr Val Asn Arg Ser Phe Gly Met Phe Ser Asp Glu Asp Pro Lys Arg
                485                 490                 495
Phe Lys Ser Pro Leu Glu Leu Tyr Ser Asn Gly Ala Ser Leu Thr Leu
                500                 505                 510
Leu Val Tyr Ile Ser Ala Leu Asn Ile Ser Ile Phe Leu Arg Gln Ser
            515                 520                 525
Ile Gln Ala Arg Trp Ser His Val Thr Glu Lys Ala Cys Glu Asp Leu
530                 535                 540
Val Lys Glu Thr Lys Lys Ser Arg His Tyr Asp Asn Asp Lys Leu Leu
545                 550                 555                 560
Leu Asp Ser Ala Asp Asp Pro Ile Leu Val Gln Phe Ala Lys Met Asn
                565                 570                 575
His Val Leu Glu Asn Ile His Thr His Leu His Glu Arg Asp Leu Asn
                580                 585                 590
Asp Asp Glu Phe Asp Asp Pro Ile Phe Thr Lys Lys Tyr Leu Asn Lys
            595                 600                 605
Leu Met Glu Lys Tyr His Lys Gln Leu Gln Glu Ile Phe Thr Lys Leu
610                 615                 620
Asp Arg Asn Arg Pro Arg Val Ile Ala Phe Tyr Tyr Ser Val Glu Ala
625                 630                 635                 640
Tyr Leu Tyr Gln Tyr Lys Leu Ala Val Phe Ile Gly Glu Met Ser His
                645                 650                 655
Thr Ile Asn Glu Lys Val Glu Leu Pro Arg Glu Ile Met Asp Asp Phe
                660                 665                 670
Val Lys Cys Tyr His Cys Cys Lys Ser Ala Leu Glu Glu Phe Ser Lys
            675                 680                 685
Leu Glu Pro Ile Leu Ile Thr Ser Leu Pro Leu Phe His Thr Ser Arg
690                 695                 700
Ile Ile Tyr Thr Val Gly Met Leu Leu Leu Lys Leu Arg Tyr Ser Val
705                 710                 715                 720
Val Ala Ile Pro Ser Phe His Asp Leu Met Pro Leu Thr Asp Asp Ala
                725                 730                 735
Ile Ala Leu Val Ile Gly Val Asn Asn Leu Leu Glu Lys Thr Ser Glu
                740                 745                 750
Leu Tyr Pro Phe Asn Asn Ser Leu Tyr Lys Phe Arg Tyr Val Ile Ala
            755                 760                 765
Leu Phe Cys Gln Thr Tyr Ala Asn Lys Val Ile Asp Val Ala Asp Arg
770                 775                 780
```

Tyr Asn Ala Glu Arg Glu Lys Leu Lys Glu Lys Gln Val Ile Asp Glu
785                 790                 795                 800

Val Ser Asn Gly His Asp Gly Thr Lys Pro Ile Asn Ala Tyr Val Thr
            805                 810                 815

Glu Ser Gln Lys Met Pro Thr Glu Glu Asp Pro Ile Ile Asp Asn Asn
        820                 825                 830

Thr Asn Gln Asn Ile Thr Ala Val Pro Asp Glu Met Leu Pro Val Tyr
            835                 840                 845

Ser Arg Val Arg Asp Asp Thr Ala Ala Met Asn Leu Asn Ile Asn Ser
850                 855                 860

Thr Ser Tyr Met Asn Glu Ser Pro His Glu His Arg Glu Ser Met Thr
865                 870                 875                 880

Gly Thr Thr Leu Leu Pro Pro Pro Phe Ile Ser Asn Asp Val Thr Asn
                885                 890                 895

Ser Ala Asp Ser Thr Asn Ile Lys Pro Ser Pro Ser Ser Ser Val Asp
            900                 905                 910

Asn Leu Asn Asp Tyr Leu Thr Asp Ile Asn Ser Leu Ala Trp Gly Val
            915                 920                 925

Asn Ser Leu Asn Asp Glu Phe Trp Thr Asp Leu Phe Met Asn Asp Ile
930                 935                 940

<210> SEQ ID NO 24
<211> LENGTH: 1517
<212> TYPE: PRT
<213> ORGANISM: Kluyveromyces marxianus

<400> SEQUENCE: 24

Met Ser Asn Ser Ser Ser Glu Gly Lys Thr Asn Glu Asp Gly Arg
1               5                   10                  15

Asn Ser Val His Ser Ser Asp Ser Phe Ala Gln Ser Val Ala Ser Phe
            20                  25                  30

His Leu Asp Asp Asn Glu Ser Gln Asn Val Thr Ala Gln Leu Ser Gln
        35                  40                  45

Gln Ile Thr Asn Val Leu Ser Asn Ser Asn Gly Ala Glu Arg Ile Glu
    50                  55                  60

Ser Leu Ala Arg Val Ile Ser Thr Lys Thr Lys Gln Met Glu Ser
65                  70                  75                  80

Phe Glu Val Asn Gln Leu Asp Phe Asp Leu Lys Ala Leu Leu Asn Tyr
                85                  90                  95

Leu Arg Ser Ser Gln Leu Glu Gln Gly Ile Glu Pro Gly Asp Ser Gly
            100                 105                 110

Ile Ala Phe His Asp Leu Thr Ala Val Gly Ile Asp Ala Ser Ala Ala
        115                 120                 125

Phe Gly Pro Ser Val Glu Glu Met Val Arg Ser Trp Ile His Phe Pro
    130                 135                 140

Val Arg Leu Trp Lys Lys Ile Cys Arg Gln Lys Ser Glu Thr Pro Leu
145                 150                 155                 160

Arg Asn Ile Ile Gln His Cys Thr Gly Val Val Glu Ser Gly Glu Met
                165                 170                 175

Leu Phe Val Val Gly Arg Pro Gly Ala Gly Cys Ser Thr Leu Leu Lys
            180                 185                 190

Cys Leu Ser Gly Glu Thr Gly Glu Leu Val Glu Val Thr Gly Asp Ile
        195                 200                 205

Ser Tyr Asp Gly Leu Ser Gln Glu Glu Met Met Gln Lys Phe Lys Gly

-continued

```
            210                 215                 220
Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Ser
                    245                 250                 255

Arg Ile Asp His Leu Thr Arg Ala Gln Tyr Val Asp Asn Met Arg Asp
                260                 265                 270

Leu Trp Cys Thr Val Phe Gly Leu Thr His Thr Tyr Ala Thr Asn Val
            275                 280                 285

Gly Asn Asp Val Val Arg Gly Val Ser Gly Glu Arg Lys Arg Val
        290                 295                 300

Ser Leu Val Glu Ala Leu Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
                325                 330                 335

Ala Ile Arg Thr Ala Thr Asn Met Met Asn Asn Ser Ala Ile Val Ala
                340                 345                 350

Ile Tyr Gln Ala Gly Glu Asn Ile Tyr Gln Leu Phe Asp Lys Thr Thr
            355                 360                 365

Val Leu Tyr Asn Gly Lys Gln Val Tyr Phe Gly Pro Ala Asp Glu Ala
        370                 375                 380

Val Gly Tyr Phe Glu Arg Met Gly Tyr Ile Lys Pro Asn Arg Met Thr
385                 390                 395                 400

Ser Ala Glu Phe Leu Thr Ser Ala Thr Val Asp Phe Glu Asn Arg Thr
                405                 410                 415

Leu Glu Val Arg Glu Gly Tyr Glu Glu Lys Ile Pro Lys Ser Ser Thr
                420                 425                 430

Glu Met Glu Ala Tyr Trp His Asn Ser Pro Glu Tyr Ala Lys Ala Thr
            435                 440                 445

Glu Leu Phe Asn Glu Tyr Cys Gln Ser His Pro Glu Glu Glu Thr Arg
450                 455                 460

Gln Arg Leu Glu Thr Ala Lys Lys Gln Arg Leu Gln Lys Gly Gln Arg
465                 470                 475                 480

Glu Lys Ser Gln Phe Val Val Thr Phe Trp Ala Gln Val Trp Tyr Cys
                485                 490                 495

Met Ile Arg Gly Phe Gln Arg Val Lys Gly Asp Ser Thr Tyr Thr Lys
            500                 505                 510

Val Tyr Leu Ser Ser Phe Leu Thr Lys Gly Leu Ile Val Gly Ser Met
            515                 520                 525

Phe His Lys Ile Asp Pro Lys Ser Gln Ser Thr Thr Glu Gly Ala Tyr
            530                 535                 540

Ser Arg Gly Gly Leu Leu Phe Tyr Val Leu Leu Phe Ala Ala Leu Thr
545                 550                 555                 560

Ser Leu Ala Glu Ile Ser Asn Ser Phe Gln Asn Arg Ala Ile Ile Val
                565                 570                 575

Lys Gln Lys Thr Tyr Ser Met Tyr His Thr Ser Ala Glu Ser Leu Gln
            580                 585                 590

Glu Ile Phe Thr Glu Ile Pro Thr Lys Phe Val Ala Ile Leu Thr Leu
            595                 600                 605

Ser Leu Val Ser Tyr Trp Ile Pro Val Leu Lys Tyr Asp Ala Gly Ser
        610                 615                 620

Phe Phe Gln Tyr Leu Leu Tyr Leu Phe Thr Thr Gln Gln Cys Thr Ser
625                 630                 635                 640
```

Phe Ile Phe Lys Leu Val Ala Thr Leu Thr Lys Asp Gly Gly Thr Ala
                645                 650                 655

His Ala Ile Gly Gly Leu Trp Val Leu Met Leu Thr Val Tyr Ala Gly
                660                 665                 670

Phe Val Leu Pro Ile Gly Asn Met His His Trp Ile Arg Trp Phe His
                675                 680                 685

Tyr Leu Asn Pro Leu Thr Tyr Ala Tyr Glu Ser Leu Met Ser Thr Glu
                690                 695                 700

Phe His Gly Arg Lys Met Leu Cys Ser Arg Leu Leu Pro Ser Gly Pro
705                 710                 715                 720

Gly Tyr Glu Asn Val Ser Ile Ala His Lys Ile Cys Asp Ala Ala Gly
                725                 730                 735

Ala Val Ala Gly Gln Leu Tyr Val Ser Gly Asp Ala Tyr Val Leu Lys
                740                 745                 750

Lys Tyr His Phe Arg Tyr Lys His Ala Trp Arg Asp Trp Gly Ile Asn
                755                 760                 765

Ile Val Trp Thr Phe Gly Tyr Ile Val Met Asn Val Val Met Ser Glu
                770                 775                 780

Tyr Leu Lys Pro Leu Glu Gly Gly Asp Leu Leu Tyr Lys Arg
785                 790                 795                 800

Gly His Met Pro Glu Leu Gly Ser Glu Ser Val Asp Ser Lys Val Ala
                805                 810                 815

Ser Arg Glu Glu Met Met Glu Ser Leu Asn Gly Pro Gly Val Asp Leu
                820                 825                 830

Glu Lys Val Ile Ala Ser Lys Asp Val Phe Thr Trp Asn His Leu Asn
                835                 840                 845

Tyr Thr Ile Pro Tyr Asp Gly Ala Thr Arg Gln Leu Leu Ser Asp Val
                850                 855                 860

Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
                885                 890                 895

Val Gly Val Ile Thr Gly Asp Met Leu Val Asn Ala Lys Pro Leu Pro
                900                 905                 910

Pro Ser Phe Asn Arg Ser Cys Gly Tyr Val Ala Gln Ala Asp Asn His
                915                 920                 925

Met Gly Glu Leu Ser Val Arg Glu Ser Leu Arg Phe Ala Ala Glu Leu
                930                 935                 940

Arg Gln Pro Lys Ser Val Pro Leu Gln Glu Lys Tyr Asp Tyr Val Glu
945                 950                 955                 960

Lys Ile Ile Ser Leu Leu Gly Met Glu Lys Tyr Ala Glu Ala Ile Ile
                965                 970                 975

Gly Lys Thr Gly Arg Gly Leu Asn Val Glu Gln Arg Lys Lys Leu Ser
                980                 985                 990

Ile Gly Val Glu Leu Val Ala Lys Pro Ser Leu Leu Leu Phe Leu Asp
                995                 1000                1005

Glu Pro Thr Ser Gly Leu Asp Ser Gln Ser Ala Trp Ser Ile Val
        1010                1015                1020

Gln Phe Met Arg Ala Leu Ala Asp Ser Gly Gln Ser Ile Leu Cys
        1025                1030                1035

Thr Ile His Gln Pro Ser Ala Thr Leu Phe Glu Gln Phe Asp Arg
        1040                1045                1050

| | | | | | | | | | | | |
|---|---|---|---|---|---|---|---|---|---|---|---|
|Leu|Leu|Leu|Leu|Lys|Lys|Gly|Lys|Met|Val|Tyr|Phe Gly Asp|
|1055| | | | |1060| | | |1065| | |

Ile Gly Glu Asn Ser Ser Thr Leu Leu Asn Tyr Phe Glu Arg Gln
1070                1075              1080

Ser Gly Val Lys Cys Gly Lys Ser Glu Asn Pro Ala Glu Tyr Met
1085                1090              1095

Leu Asn Cys Ile Gly Ala Gly Ala Thr Ala Ser Ala Asp Ala Asp
1100                1105              1110

Trp His Asp Leu Trp Leu Gln Ser Pro Glu Cys Ala Ala Ala Arg
1115                1120              1125

Glu Glu Val Glu Glu Leu His Arg Thr Leu Ala Ser Arg Pro Val
1130                1135              1140

Thr Asp Asp Lys Glu Leu Ala Gly Arg Tyr Ala Ala Ser Tyr Leu
1145                1150              1155

Thr Gln Met Lys Cys Val Phe Arg Arg Thr Asn Ile Gln Phe Trp
1160                1165              1170

Arg Ser Pro Val Tyr Ile Arg Ala Lys Phe Leu Glu Cys Val Leu
1175                1180              1185

Cys Ala Leu Phe Val Gly Leu Ser Tyr Val Gly Val Asp His Ser
1190                1195              1200

Ile Ala Gly Ala Ser Gln Ser Phe Ser Ser Ile Phe Met Met Leu
1205                1210              1215

Leu Ile Ala Leu Ala Met Val Asn Gln Leu His Val Phe Ala Leu
1220                1225              1230

Asp Ser Arg Glu Leu Tyr Glu Val Arg Glu Ala Ala Ser Asn Thr
1235                1240              1245

Phe His Trp Ser Val Leu Leu Leu Asn His Thr Phe Val Glu Ile
1250                1255              1260

Ile Trp Ser Thr Leu Cys Glu Phe Ile Cys Trp Ile Cys Tyr Tyr
1265                1270              1275

Trp Pro Ala Gln Tyr Ser Gly Arg Ala Ser His Ala Gly Tyr Phe
1280                1285              1290

Phe Leu Ile Tyr Val Ile Met Phe Pro Ala Tyr Phe Val Ser Tyr
1295                1300              1305

Gly Cys Trp Val Phe Tyr Met Ser Pro Asp Val Pro Ser Ala Ser
1310                1315              1320

Met Ile Asn Ser Asn Leu Phe Ala Gly Met Leu Leu Phe Cys Gly
1325                1330              1335

Ile Leu Gln Pro Lys Asp Lys Met Pro Gly Phe Trp Lys Arg Phe
1340                1345              1350

Met Tyr Asn Val Ser Pro Phe Thr Tyr Val Val Gln Ser Leu Val
1355                1360              1365

Thr Pro Leu Val Gln Gly Lys Lys Val Arg Cys Thr Lys Asn Glu
1370                1375              1380

Phe Ala Val Val Asn Pro Pro Glu Gly Gln Thr Cys Ser Gln Tyr
1385                1390              1395

Phe Ala Arg Phe Ile Lys Asp Asn Thr Gly Tyr Leu Lys Asn Pro
1400                1405              1410

Asn Asp Thr Glu Ser Cys His Tyr Cys Pro Tyr Ser Tyr Gln Gln
1415                1420              1425

Glu Val Val Glu Gln Tyr Asn Val Arg Trp Val Tyr Arg Trp Arg
1430                1435              1440

Asn Phe Gly Phe Leu Trp Ala Tyr Ile Gly Phe Asn Phe Phe Ala

```
              1445                1450                1455

Met Leu Ala Cys Tyr Trp Val Leu Arg Val Lys Asn Tyr Ser Ile
            1460                1465                1470

Thr Ser Ile Phe Gly Val Phe Lys Ile Gly Asn Trp Lys Lys Ala
            1475                1480                1485

Ile His His Asp Ser Arg His Glu Lys Asp His Thr Ile Phe Gln
            1490                1495                1500

Glu Lys Pro Gly Asp Ala Ala Asn Val Gln Lys Thr Lys Ala
            1505                1510                1515

<210> SEQ ID NO 25
<211> LENGTH: 261
<212> TYPE: PRT
<213> ORGANISM: Artificial Sequence
<220> FEATURE:
<223> OTHER INFORMATION: Synthetic Sequence

<400> SEQUENCE: 25

Met Ser Ser Leu Lys Pro Lys Ile Lys Ala Ile Ser Met Met Pro Lys
1               5                   10                  15

Leu Val Leu Val Arg His Gly Gln Ser Glu Trp Asn Glu Lys Asn Leu
            20                  25                  30

Phe Thr Gly Trp Val Asp Val Lys Leu Ser Ala Val Gly Glu Lys Glu
        35                  40                  45

Ala Ala Arg Ala Gly Glu Leu Leu Lys Glu Ala Asn Ile Lys Pro Asp
    50                  55                  60

Val Leu Tyr Thr Ser Lys Leu Ser Arg Ala Ile Gln Thr Ala Asn Ile
65                  70                  75                  80

Ala Leu Glu Lys Ala Asp Arg Leu Trp Ile Pro Val Lys Arg Ser Trp
                85                  90                  95

Arg Leu Asn Glu Arg His Tyr Gly Ala Leu Gln Gly Lys Asp Lys Ala
            100                 105                 110

Glu Thr Leu Glu Gln Tyr Gly Glu Glu Lys Phe Gln Thr Trp Arg Arg
        115                 120                 125

Ser Phe Asp Val Pro Pro Pro Ile Glu Asp Asp Ser Glu Phe Ser
130                 135                 140

Gln Lys Gly Asp Glu Arg Tyr Ala Asp Val Asp Pro Ala Val Leu Pro
145                 150                 155                 160

Lys Thr Glu Ser Leu Ala Leu Val Ile Asp Arg Leu Leu Pro Tyr Trp
                165                 170                 175

Gln Asp Val Ile Ala Lys Asp Leu Leu Ala Gly Lys Thr Val Leu Ile
            180                 185                 190

Ala Ala His Gly Asn Ser Leu Arg Ala Leu Val Lys His Leu Asp Asn
        195                 200                 205

Ile Ser Asp Ala Asp Ile Ala Gly Leu Asn Ile Pro Thr Gly Ile Pro
    210                 215                 220

Leu Val Tyr Glu Leu Asp Glu Asn Leu Lys Pro Thr Lys Pro Ala Tyr
225                 230                 235                 240

Tyr Leu Asp Pro Glu Ala Ala Ala Gly Ala Ala Ala Val Ala Ala
                245                 250                 255

Gln Gly Lys Lys Lys
            260

<210> SEQ ID NO 26
<211> LENGTH: 441
<212> TYPE: PRT
```

<213> ORGANISM: Artificial Sequence
<220> FEATURE:
<223> OTHER INFORMATION: Synthetic Sequence

<400> SEQUENCE: 26

```
Met Ala Ile Ser Lys Ile His Ala Arg Ser Val Tyr Asp Ser Arg Gly
1               5                   10                  15

Asn Pro Thr Val Glu Val Asp Leu Thr Thr Glu Lys Gly Leu Phe Arg
            20                  25                  30

Ala Ile Val Pro Ser Gly Ala Ser Thr Gly Ile His Glu Ala Leu Glu
        35                  40                  45

Leu Arg Asp Gly Asp Lys Ser Lys Trp Leu Gly Lys Gly Val Leu Lys
    50                  55                  60

Ala Val Ala Asn Val Asn Asp Val Ile Ala Pro Ala Leu Ile Lys Ala
65                  70                  75                  80

Asn Ile Asp Val Lys Asp Gln Ser Lys Val Asp Glu Phe Leu Ile Lys
                85                  90                  95

Leu Asp Gly Thr Pro Asn Lys Ser Lys Leu Gly Ala Asn Ala Ile Leu
            100                 105                 110

Gly Val Ser Leu Ala Ala Ala Lys Ala Ala Ala Glu Lys Gly Val
        115                 120                 125

Pro Leu Tyr Ala His Ile Ala Asp Leu Ala Gly Thr Lys Thr Lys Pro
    130                 135                 140

Tyr Val Leu Pro Val Pro Phe Gln Asn Val Leu Asn Gly Gly Ser His
145                 150                 155                 160

Ala Gly Gly Ala Leu Ala Phe Gln Glu Phe Met Ile Val Pro Thr Gly
                165                 170                 175

Ala Pro Ser Phe Ser Glu Ala Leu Arg Ile Gly Ser Glu Val Tyr His
            180                 185                 190

Asn Leu Lys Ser Leu Ala Lys Lys Lys Tyr Gly Gln Ser Ala Gly Asn
        195                 200                 205

Val Gly Asp Glu Gly Gly Val Ala Pro Asp Ile Gln Thr Ala Glu Glu
    210                 215                 220

Ala Leu Asp Leu Ile Val Asp Ala Ile Glu Ala Ala Gly Tyr Thr Gly
225                 230                 235                 240

Lys Val Lys Ile Ala Leu Asp Val Ala Ser Ser Glu Phe Tyr Lys Asp
                245                 250                 255

Asp Ala Gly Lys Tyr Asp Leu Asp Phe Lys Asn Pro Glu Ser Asp Pro
            260                 265                 270

Ser Lys Trp Leu Thr Gly Glu Gln Leu Ala Asp Leu Tyr His Ser Leu
        275                 280                 285

Ala Lys Lys Tyr Pro Ile Val Ser Ile Glu Asp Pro Phe Ala Glu Asp
    290                 295                 300

Asp Trp Glu Ala Trp Ser His Phe Tyr Lys Thr Ala Gly Ser Asp Ile
305                 310                 315                 320

Gln Ile Val Gly Asp Asp Leu Thr Val Thr Asn Pro Ile Arg Ile Lys
                325                 330                 335

Thr Ala Ile Glu Lys Lys Ala Ala Asn Ala Leu Leu Leu Lys Val Asn
            340                 345                 350

Gln Ile Gly Thr Leu Thr Glu Ser Ile Gln Ala Ala Lys Asp Ser Tyr
        355                 360                 365

Ala Ala Gly Trp Gly Val Met Val Ser His Arg Ser Gly Glu Thr Glu
    370                 375                 380

Asp Thr Phe Ile Ala Asp Leu Val Val Gly Leu Arg Thr Gly Gln Ile
```

```
385                 390                 395                 400
Lys Thr Gly Ala Pro Ala Arg Ser Glu Arg Leu Ala Lys Leu Asn Gln
                405                 410                 415

Ile Leu Arg Ile Glu Glu Leu Gly Asp Lys Ala Ile Tyr Ala Gly
            420                 425                 430

Glu Asn Phe His Thr Ala Val Asn Leu
            435                 440

<210> SEQ ID NO 27
<211> LENGTH: 438
<212> TYPE: PRT
<213> ORGANISM: Schizosaccharomyces pombe

<400> SEQUENCE: 27

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65              70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Thr Arg Ala Pro Leu Lys Phe
305                 310                 315                 320
```

```
Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435

<210> SEQ ID NO 28
<211> LENGTH: 437
<212> TYPE: PRT
<213> ORGANISM: Saccharomyces cerevisiae

<400> SEQUENCE: 28

Met Ala Val Ser Lys Val Tyr Ala Arg Ser Val Tyr Asp Ser Arg Gly
1               5                   10                  15

Asn Pro Thr Val Glu Val Glu Leu Thr Thr Glu Lys Gly Val Phe Arg
            20                  25                  30

Ser Ile Val Pro Ser Gly Ala Ser Thr Gly Val His Glu Ala Leu Glu
        35                  40                  45

Met Arg Asp Gly Asp Lys Ser Lys Trp Met Gly Lys Gly Val Leu His
    50                  55                  60

Ala Val Lys Asn Val Asn Asp Val Ile Ala Pro Ala Phe Val Lys Ala
65                  70                  75                  80

Asn Ile Asp Val Lys Asp Gln Lys Ala Val Asp Asp Phe Leu Ile Ser
                85                  90                  95

Leu Asp Gly Thr Ala Asn Lys Ser Lys Leu Gly Ala Asn Ala Ile Leu
            100                 105                 110

Gly Val Ser Leu Ala Ala Ser Arg Ala Ala Ala Ala Glu Lys Asn Val
        115                 120                 125

Pro Leu Tyr Lys His Leu Ala Asp Leu Ser Lys Ser Lys Thr Ser Pro
    130                 135                 140

Tyr Val Leu Pro Val Pro Phe Leu Asn Val Leu Asn Gly Gly Ser His
145                 150                 155                 160

Ala Gly Gly Ala Leu Ala Leu Gln Glu Phe Met Ile Ala Pro Thr Gly
                165                 170                 175

Ala Lys Thr Phe Ala Glu Ala Leu Arg Ile Gly Ser Glu Val Tyr His
            180                 185                 190

Asn Leu Lys Ser Leu Thr Lys Lys Arg Tyr Gly Ala Ser Ala Gly Asn
        195                 200                 205

Val Gly Asp Glu Gly Gly Val Ala Pro Asn Ile Gln Thr Ala Glu Glu
    210                 215                 220

Ala Leu Asp Leu Ile Val Asp Ala Ile Lys Ala Ala Gly His Asp Gly
225                 230                 235                 240

Lys Ile Lys Ile Gly Leu Asp Cys Ala Ser Ser Glu Phe Phe Lys Asp
                245                 250                 255
```

-continued

```
Gly Lys Tyr Asp Leu Asp Phe Lys Asn Pro Asn Ser Asp Lys Ser Lys
            260                 265                 270

Trp Leu Thr Gly Pro Gln Leu Ala Asp Leu Tyr His Ser Leu Met Lys
        275                 280                 285

Arg Tyr Pro Ile Val Ser Ile Glu Asp Pro Phe Ala Glu Asp Trp
    290                 295                 300

Glu Ala Trp Ser His Phe Phe Lys Thr Ala Gly Ile Gln Ile Val Ala
305                 310                 315                 320

Asp Asp Leu Thr Val Thr Asn Pro Lys Arg Ile Ala Thr Ala Ile Glu
            325                 330                 335

Lys Lys Ala Ala Asp Ala Leu Leu Lys Val Asn Gln Ile Gly Thr
        340                 345                 350

Leu Ser Glu Ser Ile Lys Ala Ala Gln Asp Ser Phe Ala Ala Gly Trp
        355                 360                 365

Gly Val Met Val Ser His Arg Ser Gly Glu Thr Glu Asp Thr Phe Ile
    370                 375                 380

Ala Asp Leu Val Val Gly Leu Arg Thr Gly Gln Ile Lys Thr Gly Ala
385                 390                 395                 400

Pro Ala Arg Ser Glu Arg Leu Ala Lys Leu Asn Gln Leu Leu Arg Ile
            405                 410                 415

Glu Glu Glu Leu Gly Asp Asn Ala Val Phe Ala Gly Asn Phe His
        420                 425                 430

His Gly Asp Lys Leu
        435

<210> SEQ ID NO 29
<211> LENGTH: 437
<212> TYPE: PRT
<213> ORGANISM: Saccharomyces cerevisiae

<400> SEQUENCE: 29

Met Ala Val Ser Lys Val Tyr Ala Arg Ser Val Tyr Asp Ser Arg Gly
1               5                   10                  15

Asn Pro Thr Val Glu Val Glu Leu Thr Thr Glu Lys Gly Val Phe Arg
            20                  25                  30

Ser Ile Val Pro Ser Gly Ala Ser Thr Gly Val His Glu Ala Leu Glu
        35                  40                  45

Met Arg Asp Glu Asp Lys Ser Lys Trp Met Gly Lys Gly Val Met Asn
    50                  55                  60

Ala Val Asn Asn Val Asn Asn Val Ile Ala Ala Phe Val Lys Ala
65                  70                  75                  80

Asn Leu Asp Val Lys Asp Gln Lys Ala Val Asp Asp Phe Leu Leu Ser
            85                  90                  95

Leu Asp Gly Thr Ala Asn Lys Ser Lys Leu Gly Ala Asn Ala Ile Leu
        100                 105                 110

Gly Val Ser Met Ala Ala Ala Arg Ala Ala Ala Ala Glu Lys Asn Val
    115                 120                 125

Pro Leu Tyr Gln His Leu Ala Asp Leu Ser Lys Ser Lys Thr Ser Pro
    130                 135                 140

Tyr Val Leu Pro Val Pro Phe Leu Asn Val Leu Asn Gly Gly Ser His
145                 150                 155                 160

Ala Gly Gly Ala Leu Ala Leu Gln Glu Phe Met Ile Ala Pro Thr Gly
            165                 170                 175

Ala Lys Thr Phe Ala Glu Ala Met Arg Ile Gly Ser Glu Val Tyr His
```

```
                180             185             190
Asn Leu Lys Ser Leu Thr Lys Lys Arg Tyr Gly Ala Ser Ala Gly Asn
            195                 200                 205
Val Gly Asp Glu Gly Gly Val Ala Pro Asn Ile Gln Thr Ala Glu Glu
        210                 215                 220
Ala Leu Asp Leu Ile Val Asp Ala Ile Lys Ala Gly His Asp Gly
225                 230                 235                 240
Lys Val Lys Ile Gly Leu Asp Cys Ala Ser Ser Glu Phe Phe Lys Asp
                245                 250                 255
Gly Lys Tyr Asp Leu Asp Phe Lys Asn Pro Glu Ser Asp Lys Ser Lys
            260                 265                 270
Trp Leu Thr Gly Val Glu Leu Ala Asp Met Tyr His Ser Leu Met Lys
        275                 280                 285
Arg Tyr Pro Ile Val Ser Ile Glu Asp Pro Phe Ala Glu Asp Asp Trp
290                 295                 300
Glu Ala Trp Ser His Phe Phe Lys Thr Ala Gly Ile Gln Ile Val Ala
305                 310                 315                 320
Asp Asp Leu Thr Val Thr Asn Pro Ala Arg Ile Ala Thr Ala Ile Glu
                325                 330                 335
Lys Lys Ala Ala Asp Ala Leu Leu Leu Lys Val Asn Gln Ile Gly Thr
            340                 345                 350
Leu Ser Glu Ser Ile Lys Ala Ala Gln Asp Ser Phe Ala Ala Asn Trp
        355                 360                 365
Gly Val Met Val Ser His Arg Ser Gly Glu Thr Glu Asp Thr Phe Ile
370                 375                 380
Ala Asp Leu Val Val Gly Leu Arg Thr Gly Gln Ile Lys Thr Gly Ala
385                 390                 395                 400
Pro Ala Arg Ser Glu Arg Leu Ala Lys Leu Asn Gln Leu Leu Arg Ile
                405                 410                 415
Glu Glu Glu Leu Gly Asp Lys Ala Val Tyr Ala Gly Asn Phe His
            420                 425                 430
His Gly Asp Lys Leu
        435

<210> SEQ ID NO 30
<211> LENGTH: 479
<212> TYPE: PRT
<213> ORGANISM: Escherichia coli

<400> SEQUENCE: 30

Met Ser Val Pro Val Gln His Pro Met Tyr Ile Asp Gly Gln Phe Val
1               5                   10                  15
Thr Trp Arg Gly Asp Ala Trp Ile Asp Val Val Asn Pro Ala Thr Glu
            20                  25                  30
Ala Val Ile Ser Arg Ile Pro Asp Gly Gln Ala Glu Asp Ala Arg Lys
        35                  40                  45
Ala Ile Asp Ala Ala Glu Arg Ala Gln Pro Glu Trp Glu Ala Leu Pro
    50                  55                  60
Ala Ile Glu Arg Ala Ser Trp Leu Arg Lys Ile Ser Ala Gly Ile Arg
65                  70                  75                  80
Glu Arg Ala Ser Glu Ile Ser Ala Leu Ile Val Glu Glu Gly Gly Lys
                85                  90                  95
Ile Gln Gln Leu Ala Glu Val Glu Val Ala Phe Thr Ala Asp Tyr Ile
            100                 105                 110
```

-continued

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
            195                 200                 205

Gly Glu Thr Val Gly Gln Glu Leu Ala Gly Asn Pro Lys Val Ala Met
        210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
                260                 265                 270

Ile Val Asp Ser Arg Val Ile Asn Ser Gly Gln Val Cys Asn Cys Ala
            275                 280                 285

Glu Arg Val Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
            355                 360                 365

Leu Leu Leu Asp Val Arg Gln Glu Met Ser Ile Met His Glu Glu Thr
    370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
            435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475

RECOMBINANT HOST CELLS AND METHODS FOR THE PRODUCTION OF GLYCERIC ACID AND DOWNSTREAM PRODUCTS

CROSS-REFERENCE TO RELATED APPLICATIONS

This application claims the benefit of priority under 35 U.S.C. 119(e) and Article 2 of the Paris Convention for the Protection of Industrial Property (1883) to U.S. provisional application Ser. No. 62/632,237, filed 19 Feb. 2018, the entire contents of which are incorporated herein by this reference.

REFERENCE TO SEQUENCE LISTING

This application contains a Sequence Listing submitted via EFS-web in computer readable form, and is hereby incorporated by reference in its entirety. The ASCII copy, created on Feb. 14, 2019, is named LYGOS_0014_01_WO_ST25 and is 120 KB in size.

BACKGROUND

The long-term economic and environmental concerns associated with the petrochemical industry have provided the impetus for increased research, development, and commercialization of processes for conversion of carbon feedstocks into chemicals that can replace those petroleum feedstocks. One approach is the development of biorefining processes to convert renewable feedstocks into products that can replace petroleum-derived chemicals. Two common goals in improving a biorefining process include achieving a lower cost of production and reducing detrimental effects on the environment. The present disclosure provides a safer and cheaper alternative to incumbent production methods that comprise hazardous petrochemicals and extreme process conditions.

Glyceric acid is an important precursor molecule that can be converted to high-value, biodegradable polymers which are in high demand in the food packaging, medical device and personal care industries. As glyceric acid has three functional groups (i.e., primary alcohol, secondary alcohol, and carboxylic acid) it is a valuable chemical building block for a range of applications, including polymers, superabsorbent polymers, and solvents.

Currently, the synthesis of glyceric acid and its derivatives requires a petroleum feedstock, extreme run temperatures and/or pressures, and hazardous materials that pose health and safety risks. Glyceric acid may be prepared by catalytic oxidation of glycerol with run temperatures as high as 350° C., and precious metal catalysts that comprise palladium and platinum. Likewise, glycolic acid may be prepared by hydrative carbonylation of formaldehyde with carbon monoxide and sulfuric acid, wherein run conditions range from 210° C. to 240° C. and ~900 atm, or saponification of chloroacetic acid with alkali metal hydroxide, wherein run temperatures range from 100° C. to 160° C. Both formaldehyde and chloroacetic acid are recognized as toxic air contaminants by the U.S. Environmental Protection Agency and the California Air Toxics Program and commercial production of acrylic acid via oxidation of propylene requires run temperatures in the range of 250° C. to 450° C. Thus, there is a need for new low-cost, energy efficient, high yielding manufacturing methods for the synthesis of glyceric acid and its derivatives.

SUMMARY

The present disclosure provides recombinant host cells and methods of their production and use to produce glyceric acid and downstream products and derivatives. These recombinant host cells utilize microbial fermentation from renewable feedstocks (for example, glucose) to produce glyceric acid. This glyceric acid production utilizes an efficient carbon conversion route; in cases where glucose is used as the raw material, the stoichiometric theoretical yield is 2-mols of glyceric acid for every mol of glucose, equating to one of the highest yielding products from glucose at 100% carbon conversion.

The microbial fermentation process disclosed herein for the production of glyceric acid is run at both ambient atmospheric pressure and temperature, reducing the cost and environmental impact of manufacturing relative to the incumbent petrochemical processes. No organism in nature, including yeast, is known to produce glyceric acid from glucose in more than trace amounts. The materials and methods described herein comprise a renewable and cheaper starting material and an environmentally-benign biosynthetic process. The present disclosure provides a safer and cheaper alternative to incumbent methods that comprise hazardous petrochemicals and extreme process conditions. The materials and methods described herein enable higher fermentation yields and productivities in the production of glyceric acid and its downstream products.

Thus, in various embodiments, the present disclosure provides recombinant host cells capable of producing glyceric acid comprising one or more heterologous nucleic acids that encode the glyceric acid biosynthetic pathway, wherein the pathway enzymes comprise a 3-phosphoglycerate phosphatase and/or a 2-phosphoglycerate phosphatase.

In other embodiments, this disclosure provides recombinant host cells that further comprise one or more heterologous nucleic acids encoding one or more ancillary proteins that function in redox cofactor recycling, redox cofactor biogenesis, or organic acid transport. In some embodiments, the one or more ancillary proteins comprise mitochondrial external NADH dehydrogenase, water-forming NADH oxidase, glyceric acid transporter, or combination thereof. In other embodiments, this disclosure provides recombinant host cells that further comprise a genetic disruption of one or more genes wherein the one or more genes encodes phosphoglycerate mutase, phosphoglycerate dehydrogenase, enolase, glycerate 3-kinase, glycerate 2-kinase, or glycerol-3-phosphate dehydrogenase, or combination thereof. In other embodiments, this disclosure provides recombinant host cells that further comprise one or more heterologous nucleic acids that encode a glycolic acid biosynthetic pathway, wherein the pathway enzymes comprise a hydroxypyruvate reductase, a hydroxypyruvate decarboxylase, and a glycoaldehyde dehydrogenase.

In other embodiments, this disclosure provides the invention provides a method for the production of glyceric acid that comprises culturing the recombinant host cells of the invention for a sufficient period of time to produce glyceric acid. In other embodiments, this disclosure provides a method for the production of glycolic acid that comprises culturing the recombinant host cells of the invention for a sufficient period of time to produce glycolic acid. In other embodiments, this disclosure provides a process to produce glycerate esters comprising the steps of recovering glyceric acid or glycerate salt from fermentation broth, forming the glycerate ester by esterification with supercritical $CO_2$, and purifying said glycerate ester. In an eighth aspect, the invention provides a deoxydehydration process to produce acrylate esters comprising the steps of converting a glycerate ester to an acrylate ester, and purifying said acrylate ester. In various embodiments, the deoxydehydration alcohol is methanol, ethanol, isopropyl alcohol, butanol, 3-pentanol, or isobutanol.

DETAILED DESCRIPTION

The present disclosure provides recombinant host cells, materials and methods for the biological production, purification and synthesis of glyceric acid and downstream products.

While the present disclosure describes aspects and specific embodiments, those skilled in the art will recognize that various changes may be made and equivalents may be substituted without departing from this disclosure. The present disclosure is not limited to particular nucleic acids, expression vectors, enzymes, biosynthetic pathways, host microorganisms, or processes, as such may vary. The terminology used herein is for the purposes of describing particular aspects and embodiments only, and is not to be construed as limiting. In addition, many modifications may be made to adapt a particular situation, material, composition of matter, process, process steps or process flows, in accordance with this disclosure. All such modifications are within the scope of the claims appended hereto.

Section 1: Definitions

In this specification and in the claims that follow, reference will be made to a number of terms that shall be defined to have the following meanings.

The term "accession number" and similar terms such as "protein accession number", "UniProt ID", "gene ID" and "gene accession number" refer to designations given to specific proteins or genes. These identifiers described a gene or protein sequence in publicly accessible databases such as the National Center for Biotechnology Information (NCBI).

The term "heterologous" as used herein refers to a material that is non-native to a cell. For example, a nucleic acid is heterologous to a cell, and so is a "heterologous nucleic acid" with respect to that cell, if at least one of the following is true: 1) the nucleic acid is not naturally found in that cell (that is, it is an "exogenous" nucleic acid); 2) the nucleic acid is naturally found in a given host cell (that is, "endogenous to"), but the nucleic acid or the RNA or protein resulting from transcription and translation of this nucleic acid is produced or present in the host cell in an unnatural (for example, greater or lesser than naturally present) amount; 3) the nucleic acid comprises a nucleotide sequence that encodes a protein endogenous to a host cell but differs in sequence from the endogenous nucleotide sequence that encodes that same protein (having the same or substantially the same amino acid sequence), typically resulting in the protein being produced in a greater amount in the cell, or in the case of an enzyme, producing a mutant version possessing altered (for example, higher or lower or different) activity; and/or 4) the nucleic acid comprises two or more nucleotide sequences that are not found in the same relationship to each other in the cell. As another example, a protein is heterologous to a host cell if it is produced by translation of RNA or the corresponding RNA is produced by transcription of a heterologous nucleic acid. Further, a protein is also heterologous to a host cell if it is a mutated version of an endogenous protein, and the mutation was introduced by genetic engineering.

The term "homologous", as well as variations thereof, such as "homology", refers to the similarity of a nucleic acid or amino acid sequence, typically in the context of a coding sequence for a gene or the amino acid sequence of a protein. Homology searches can be employed using a known amino acid or coding sequence (the "reference sequence") for a useful protein to identify homologous coding sequences or proteins that have similar sequences and thus are likely to perform the same useful function as the protein defined by the reference sequence. A protein having homology to a reference protein is determined, for example and without limitation, by a BLAST (https://blast.ncbi.nlm.nih.gov) search. A protein with high percent homology is highly likely to carry out the identical biochemical reaction as the reference protein. In some cases, two enzymes having greater than 40% identity will carry out identical biochemical reactions, and the higher the identity, i.e., 40, 50%, 60%, 70%, 80%, 90% or greater than 95% identity, the more likely the two proteins have the same or similar function. A protein with at least 60% homology, and in some cases, at least 40% homology, to its reference protein is defined as substantially homologous. Any protein substantially homologous to a reference sequence can be used in a host cell according to the present disclosure.

Generally, homologous proteins share substantial sequence identity. Sets of homologous proteins generally possess one or more specific amino acids that are conserved across all members of the consensus sequence protein class. The percent sequence identity of a protein relative to a consensus sequence is determined by aligning the protein sequence against the consensus sequence. Practitioners in the art will recognized that various sequence alignment algorithms are suitable for aligning a protein with a consensus sequence. See, for example, Needleman, S B, et al., "A general method applicable to the search for similarities in the amino acid sequence of two proteins." Journal of Molecular Biology 48 (3): 443-53 (1970). Following alignment of the protein sequence relative to the consensus sequence, the percentage of positions where the protein possesses an amino acid described by the same position in the consensus sequence determines the percent sequence identity. When a degenerate amino acid is present (i.e., B, Z, X, J or "+") in a consensus sequence, any of the amino acids described by the degenerate amino acid may be present in the protein at the aligned position for the protein to be identical to the consensus sequence at the aligned position. When it is not possible to distinguish between two closely related amino acids, the following one-letter symbol is used—"B" refers to aspartic acid or asparagine; "Z" refers to glutamine or glutamic acid; "J" refers to leucine or isoleucine; and "X" or "+" refers to any amino acid.

A dash (−) in a consensus sequence indicates that there is no amino acid at the specified position. A plus (+) in a consensus sequence indicates any amino acid may be present at the specified position. Thus, a plus in a consensus sequence herein indicates a position at which the amino acid is generally non-conserved; a homologous enzyme sequence, when aligned with the consensus sequence, can have any amino acid at the indicated "+" position.

The terms "bio-based" or "non-petrochemically derived" or "renewable" as used herein refer to an organic compound that is synthesized from biologically produced organic components by fermenting a microorganism. These compounds are distinguished from wholly petroleum-derived compounds or those entirely of fossil origin. A compound of renewable or non-petrochemical origin include carbon atoms that have a non-petrochemical origin. Such non-petrochemical (or bio based or renewable) compounds have a $^{14}C$ amount substantially higher than zero, such as about 1 parts per trillion or more, because they are derived from photosynthesis based starting material, such as for example, glucose or another feedstock used in producing such a compound, such as glyceric acid. In certain embodiments, such non-petrochemical based compositions provided herein, contain, for example, and without limitation:glyceric acid and other compounds of formula (I) which are non-petrochemical based.

In addition to identification of useful enzymes by percent sequence identity with a given consensus sequence, enzymes useful in the compositions and methods provided herein can also be identified by the occurrence of highly conserved amino acid residues in the query protein sequence relative to a consensus sequence. For each consensus sequence provided herein, a number of highly conserved amino acid residues are described. Enzymes useful in the compositions and methods provided herein include those that comprise a substantial number, and sometimes all, of the highly conserved amino acids at positions aligning with the indicated residues in the consensus sequence. Those skilled in the art will recognize that, as with percent identity, the presence or absence of these highly conserved amino acids in a query protein sequence can be determined following alignment of the query protein sequence relative to a given consensus sequence and comparing the amino acid found in the query protein sequence that aligns with each highly conserved amino acid specified in the consensus sequence.

Proteins that share a specific function are not always defined or limited by percent sequence identity. In some cases, a protein with low percent sequence identity with a reference protein is able to carry out the identical biochemical reaction as the reference protein. Such proteins may share three-dimensional structure which enables shared specific functionality, but not necessarily sequence similarity. Such proteins may share an insufficient amount of sequence similarity to indicate that they are homologous via evolution from a common ancestor and would not be identified by a BLAST search or other sequence-based searches. Thus, in some embodiments of the present disclosure, homologous proteins comprise proteins that lack substantial sequence similarity but share substantial functional similarity and/or substantial structural similarity.

As used herein, the term "express", when used in connection with a nucleic acid encoding an enzyme or an enzyme itself in a cell, means that the enzyme, which may be an endogenous or exogenous (heterologous) enzyme, is produced in the cell. The term "overexpress", in these contexts, means that the enzyme is produced at a higher level, i.e., enzyme levels are increased, as compared to the wild-type, in the case of an endogenous enzyme. Overexpression of an enzyme can be achieved by increasing the strength or changing the type of the promoter used to drive expression of a coding sequence, increasing the strength of the ribosome binding site or Kozak sequence, increasing the stability of the mRNA transcript, altering the codon usage, increasing the stability of the enzyme, and the like.

The terms "expression vector" or "vector" refer to a nucleic acid and/or a composition comprising a nucleic acid that can be introduced into a host cell, for example, by transduction, transformation, or infection, such that the cell then produces (i.e., expresses) nucleic acids and/or proteins other than those native to the cell, or in a manner not native to the cell, that are contained in or encoded by the nucleic acid so introduced. Thus, an "expression vector" contains nucleic acids (ordinarily DNA) to be expressed by the host cell. Optionally, the expression vector can be contained in materials to aid in achieving entry of the nucleic acids into the host cell, such as the materials associated with a virus, liposome, protein coating, or the like. Expression vectors suitable for use in various aspects and embodiments of the present disclosure include those into which a nucleic acid sequence can be, or has been, inserted, along with any operational elements. Thus, an expression vector can be transferred into a host cell and, typically, replicated therein (although, on can also employ, in some embodiments, non-replicable vectors that provide for "transient" expression). In some embodiments, an expression vector that integrates into chromosomal, mitochondrial, or plastid DNA is employed. In other embodiments, an expression vector that replicates extrachromasomally is employed. Typical expression vectors include plasmids, and expression vectors typically contain the operational elements for transcription of a nucleic acid in the vector. Such plasmids, as well as other expression vectors, are described herein or are well known to those of ordinary skill in the art.

The terms "ferment", "fermentative", and "fermentation" are used herein to describe culturing microbes under conditions to produce useful chemicals, including but not limited to conditions under which microbial growth, be it aerobic or anaerobic, occurs.

The terms "recombinant host cell", "recombinant host microorganism", and "strain" are used interchangeably herein to refer to a living cell that can be (or has been) transformed via insertion of an expression vector. A recombinant host cell or microorganism as described herein may be a prokaryotic cell (for example, a microorganism of the kingdom Eubactera) or a eukaryotic cell. A prokaryotic cell lacks a membrane-bound nucleus, while a eukaryotic cell has a membrane-bound nucleus.

The terms "isolated" or "pure" refer to material that is substantially, for example, greater than 50%, 75%, 90%, 95%, 98% or 99%, free of components that normally accompany it in its native state, for example, the state in which it is naturally found or the state in which it exists when it is first produced. Additionally, any reference to a "purified" material is intended to refer to an isolated or pure material.

As used herein, the term "nucleic acid" and variations thereof shall be generic to polydeoxyribonucleotides (containing 2-deoxy-D-ribose), polyribonucleotides (containing D-ribose), segments of polydeoxyribonucleotides, and segments of polyribonucleotides. "Nucleic acid" can also refer to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. As used herein, the symbols for nucleotides and polynucleotides are those recommended by the IUPAC-IUB Commission of Biochemical Nomenclature (Biochem. 9:4022, 1970). A "nucleic acid" may also be referred to herein with respect to its sequence, the order in which different nucleotides occur in the nucleic acid, as the sequence of nucleotides in a nucleic acid typically defines its biological activity, for example, as in the sequence of a coding region, the nucleic acid in a gene composed of a promoter and coding region, which encodes the product of a gene, which may be an RNA, for example, a rRNA, tRNA, or mRNA, or a protein (where a gene encodes a protein, both the mRNA and the protein are "gene products" of that gene).

In the present disclosure, the term "genetic disruption" refers to several ways of altering genomic, chromosomal or plasmid-based gene expression. Non-limiting examples of genetic disruptions comprise CRISPR, RNAi, nucleic acid deletions, nucleic acid insertions, nucleic acid substitutions, nucleic acid mutations, knockouts, premature stop codons and transcriptional promoter modifications. In the present disclosure, "genetic disruption" is used interchangeably with "genetic modification", "genetic mutation" and "genetic alteration." Genetic disruptions give rise to altered gene expression and or altered protein activity. Altered gene expression encompasses decreased, eliminated and increased gene expression levels. In some examples, gene expression results in protein expression, in which case the term "gene expression" is synonymous with "protein expression".

As used herein, "recombinant" refers to the alteration of genetic material by human intervention. Typically, recombinant refers to the manipulation of DNA or RNA in a cell or virus or expression vector by molecular biology (recombinant DNA technology) methods, including cloning and recombination. Recombinant can also refer to manipulation of DNA or RNA in a cell or virus by random or directed mutagenesis. A "recombinant" cell or nucleic acid can typically be described with reference to how it differs from a naturally occurring counterpart (the "wild-type"). In addition, any reference to a cell or nucleic acid that has been "engineered" or "modified" and variations of those terms, is intended to refer to a recombinant cell or nucleic acid.

The terms "transduce", "transform", "transfect", and variations thereof as used herein refers to the introduction of one or more nucleic acids into a cell. For practical purposes, the nucleic acid is stably maintained or replicated by the cell for a sufficient period of time to enable the function(s) or product(s) it encodes to be expressed for the cell to be referred to as "transduced", "transformed", or "transfected". Stable maintenance or replication of a nucleic acid may take place either by incorporation of the sequence of nucleic acids into the cellular chromosomal DNA, for example, the genome, as occurs by chromosomal integration, or by replication extrachromosomally, as occurs with a freely-replicating plasmid. A virus can be stably maintained or replicated when it is "infective": when it transduces a host microorganism, replicates, and (without the benefit of any complementary virus or vector) spreads progeny expression vectors, for example, viruses, of the same type as the original transducing expression vector to other microorganisms, wherein the progeny expression vectors possess the same ability to reproduce.

As used herein, "glyceric acid" is intended to mean the molecule having the chemical formula $C_3H_6O_4$ and a molecular mass of 106.077 g/mol (CAS No. 473-81-4). The terms "glyceric acid" and "2,3-dihydroxypropanoic acid" are used interchangeably in the present disclosure, and are synonyms.

In conditions with pH values higher than the pKa of glyceric acid (for example, pH>3.52), glyceric acid is deprotonated to the glycerate anion $C_3H_5O_4^-$. Herein, "glycerate" is also used interchangeably with "glycerate anion", and "2,3-dihydroxypropanoate", and are synonyms.

Further, the glycerate anion is capable of forming an ionic bond with a cation to produce an glycerate salt. The term "glycerate" is intended to mean a variety of glycerate salt forms, and is used interchangeably with "glycerate salt". Non-limiting examples of glycerates comprise sodium glycerate (CAS No. 50976-28-8), potassium glycerate (CAS No. 43110-90-3), and calcium glycerate (CAS No. 6057-35-8).

Glycerate salts can crystallize in various states of hydration and glycerate salts of the present disclosure are no exception. For example, calcium glycerate can form monohydrate crystals, wherein a single molecule of water crystallizes with a single molecule of calcium glycerate. Similarly, dihydrate crystals comprise two molecules of water for every molecule of calcium glycerate.

In conditions with pH values lower than the pKa of glyceric acid (for example, pH<3.52), the glycerate anion is protonated to form glyceric acid. Herein, "glycerate" is also used interchangeably with "glyceric acid" and are synonyms.

As used herein, "glycerate ester" is intended to mean an ester derived from glyceric acid, and it is synonymous with "alkyl glycerate". Non-limiting examples of glycerate esters comprise methyl glycerate (molecular formula $C_4H_8O_4$ and average mass 120.104 Da), and ethyl glycerate (molecular formula $(HO)_2C_2H_3COOC_2H_5$).

The glyceric acid, glycerate salts, and glycerate esters of the present disclosure are synthesized from biologically produced organic components by a fermenting microorganism. For example, glyceric acid, glycerate salts, and glycerate esters are synthesized from the fermentation of sugars by recombinant host cells of the present disclosure. The prefix "bio-" or the adjective "bio-based" may be used to distinguish these biologically-produced glyceric acid, glycerate salts, and glycerate esters from those that are derived from petroleum feedstocks. As used herein, "glyceric acid" is defined as "bio-based glyceric acid", "glycerate salt" is defined as "bio-based glycerate salt", and "glycerate ester" is defined as "bio-based glycerate ester".

As used herein, "glycolic acid" is intended to mean the molecule having the chemical formula $C_2H_4O_3$ and a molecular mass of 76.05 g/mol (CAS No. 79-14-1). The terms "glycolic acid", "hydroxyacetic acid", and "2-hydroxyacetic acid" are used interchangeably in the present disclosure, and are synonyms.

In conditions with pH values higher than the pKa of glycolic acid (for example, about pH>3.83 when using a sodium base, such as sodium hydroxide), glycolic acid is deprotonated to the glycolate/glycollate anion $C_2H_3O_3^-$. Herein, "glycolate" is also used interchangeably with "glycollate", "glycolate anion," "glycollate anion", "hydroxyacetate", and "2-hydroxyacetate", and are synonyms.

Further, the glycolate anion is capable of forming an ionic bond with a cation to produce an glycolate salt. The term "glycolate" is intended to mean a variety of glycolate salt forms, and is used interchangeably with "glycolate salt". Non-limiting examples of glycolates comprise sodium glycolate (CAS No. 2836-32-0), calcium glycolate (CAS No. 996-23-6), potassium glycolate (CAS No. 25904-89-6), ethyl glycolate (CAS No. 623-50-7), and methyl glycolate (CAS No. 96-35-5).

In conditions with pH values lower than the pKa of glycolate acid (for example, pH<3.83), the glycolate anion is protonated to form glycolic acid. Herein, "glycolate" is also used interchangeably with "glycolic acid" and are synonyms.

As used herein, "glycolate ester" is intended to mean an ester derived from glycolic acid, and is synonymous with "alkyl glycolate". Non-limiting examples of glycolate esters comprise ethyl glycolate (CAS No. 623-50-7), methyl glycolate (CAS No. 96-35-5) and benzyl glycolate (CAS No. 30379-58-9).

The glycolic acid, glycolate salts and glycolate esters of the present disclosure are synthesized from biologically produced organic components by a fermenting microorganism. For example, glycolic acid, glycolate salts, glycolate esters, or their precursor(s) are synthesized from the fermentation of sugars by recombinant host cells of the present disclosure. The prefix "bio-" or the adjective "bio-based" may be used to distinguish these biologically-produced glycolic acid and glycolates from those that are derived from petroleum feedstocks. As used herein, "glycolic acid" is defined as "bio-based glycolic acid", "glycolate salt" is defined as "bio-based glycolate salt", and "glycolate ester" is defined as "bio-based glycolate ester".

As used herein, "acrylic acid" is intended to mean the molecule having the chemical formula $C_3H_4O_2$ and a molecular mass of 72.06 g/mol (CAS No. 79-10-7). The terms "acrylic acid", "ethylene carboxylic acid", "propenoic acid", and "acroleic acid" are used interchangeably in the present disclosure, and are synonyms.

In conditions with pH values higher than the pKa of acrylic acid (for example, about pH>4.25 when using a sodium base, such as sodium hydroxide), acrylic acid is deprotonated to the acrylate anion $C_3H_3O_2$. Herein, "acrylate" is also used interchangeably with "propenoate", and are synonyms.

Further, the acrylate anion is capable of forming an ionic bond with a cation to produce an acrylate salt. The term "acrylate" is intended to mean a variety of acrylate salt forms, and is used interchangeably with "acrylate salt". Non-limiting examples of acrylates comprise sodium acrylate (CAS No. 7446-81-3), calcium acrylate (CAS No. 6292-01-9), calcium diacrylate (CAS No. 6292-01-9), potassium acrylate (CAS No. 10192-85-5), ammonium acrylate (CAS No. 9003-03-6), sodium methacrylate (CAS No. 5536-61-8), and zinc acrylate (CAS No. 14643-87-9).

In conditions with pH values lower than the pKa of acrylic acid (for example, pH<4.25), the acrylate anion is protonated to form acrylic acid. Herein, "acrylate" is also used interchangeably with "acrylic acid" and are synonyms.

As used herein, "acrylate ester" is intended to mean an ester derived from acrylic acid, and is synonymous with "alkyl acrylate". Non-limiting examples of acrylate esters comprise methyl acrylate (CAS No. 96-33-3), ethyl acrylate (CAS No. 140-88-5), butyl acrylate (CAS No. 141-32-2) and 2-ethylhexyl acrylate (2EHA; CAS No. 103-11-7).

The term "byproduct" or "by-product" means an undesired product related to the production of a target molecule. In the present disclosure, "byproduct" is intended to mean any amino acid, amino acid precursor, chemical, chemical precursor, organic acid, organic acid precursor, ester, ester precursor, biofuel, biofuel precursor, metabolite, or small molecule, that may accumulate during biosynthesis or chemical synthesis of glyceric acid, glycolic acid, acrylic acid, glycerate, glycolate, acrylate, glycerate ester, glycolate ester, acrylate ester, or other downstream product of the present disclosure. In some cases, "byproduct" accumulation may decrease the yields, titers or productivities of the target product (i.e., glyceric acid, glycolic acid, acrylic acid, glycerate, glycolate, acrylate, glycerate ester, glycolate ester, acrylate ester, or other downstream product) in a fermentation or in synthesis.

The redox cofactor nicotinamide adenine dinucleotide, NAD, comes in two forms—phosphorylated and un-phosphorylated. The term NAD(P) refers to both phosphorylated (NADP) and un-phosphorylated (NAD) forms, and encompasses oxidized versions ($NAD^+$ and $NADP^+$) and reduced versions (NADH and NADPH) of both forms. The term "$NAD(P)^+$" refers to the oxidized versions of phosphorylated and un-phosphorylated NAD, i.e., $NAD^+$ and $NADP^+$. Similarly, the term "NAD(P)H" refers to the reduced versions of phosphorylated and un-phosphorylated NAD, i.e., NADH and NADPH. When NAD(P)H is used to describe the redox cofactor in an enzyme catalyzed reaction, it indicates that NADH and/or NADPH is used. Similarly, when $NAD(P)^+$ is the notation used, it indicates that $NAD^+$ and/or $NADP^+$ is used. While many proteins may bind either a phosphorylated or un-phosphorylated cofactor, there are redox cofactor promiscuous proteins, natural or engineered, that are indiscriminate; in these cases, the protein may use either NADH and/or NADPH. In some embodiments, enzymes that preferentially utilize either NAD(P) or NAD may carry out the same catalytic reaction when bound to either form.

Various values for temperatures, titers, yields, oxygen uptake rate (OUR), and pH are recited in the description and in the claims. It should be understood that these values are not exact. However, the values can be approximated to the rightmost/last/least significant figure, except where otherwise indicated. For example, a temperature range of from about 30° C. to about 42° C. covers the range 25° C. to 44° C. It should be understood that numerical ranges recited can also include the recited minimum value and the recited maximum value when the values are approximated to the rightmost/last/least significant figure. For example, a temperature range of from about 25° C. to about 50° C. covers the range of 25° C. to 50° C.

Section 2: Recombinant Host Cells for Production of Glyceric Acid and Downstream Products 2.1 Host Cells The present disclosure provides recombinant host cells engineered to produce glyceric acid, wherein the recombinant host cells comprise one or more heterologous nucleic acids encoding one or more glyceric acid pathway enzymes. In certain embodiments, the recombinant host cells further comprise one or more heterologous nucleic acids encoding one or more ancillary gene products (i.e., gene products other than the glyceric acid pathway enzymes) that improve yields, titers and/or productivities of glyceric acid. In particular embodiments, the recombinant host cells further comprise disruptions or deletions of endogenous nucleic acids that improve yields, titers and/or productivities of glyceric acid. In some embodiments, the recombinant host cells are capable of producing glyceric acid under aerobic conditions. In some embodiments, the recombinant host cells are capable of producing glyceric acid under substantially anaerobic conditions. In some embodiments, the recombinant host cells produce glyceric acid at increased titers, yields and productivities as compared to a parental host cell that does not comprise said heterologous nucleic acids.

In a first aspect, this disclosure provides recombinant host cells capable of producing glyceric acid comprising one or more heterologous nucleic acids that encode the glyceric acid biosynthetic pathway, wherein the pathway enzymes comprise a 3-phosphoglycerate phosphatase and/or a 2-phosphoglycerate phosphatase. In some embodiments, the recombinant host cells comprise heterologous nucleic acids encoding a 3-phosphoglycerate phosphatase with at least 60% amino acid identity with SEQ ID NO: 7 or SEQ ID NO: 9.

In a second aspect, this disclosure provides recombinant host cells that further comprise one or more heterologous nucleic acids encoding one or more ancillary proteins that function in redox cofactor recycling, redox cofactor biogenesis, or organic acid transport. In some embodiments, the one or more ancillary proteins comprise mitochondrial external NADH dehydrogenase, water-forming NADH oxidase, glyceric acid transporter, or combination thereof. In some embodiments, the ancillary protein has at least 60% amino acid identity with SEQ ID NO: 20, SEQ ID NO: 21, SEQ ID NO: 22, SEQ ID NO: 23, SEQ ID NO: 24, or SEQ ID NO: 2.

In a third aspect, this disclosure provides recombinant host cells that further comprise a genetic disruption of one or more genes wherein the one or more genes encodes phosphoglycerate mutase, phosphoglycerate dehydrogenase, enolase, glycerate 3-kinase, glycerate 2-kinase, or glycerol-3-phosphate dehydrogenase, or combination thereof. In some embodiments, the one or more genes has at least 60% amino acid identity with SEQ ID NO: 14, SEQ ID NO: 15, SEQ ID NO: 16, SEQ ID NO: 17, SEQ ID NO: 19, or SEQ ID NO: 25. In some of these embodiments, the recombinant host cells produce less than 5 g/l serine. In some of these embodiments, the recombinant host cells produce less than 5 g/l glycerol. In some of these embodiments, the recombinant host cells produce less than 5 g/l ethanol. In some of these embodiments, the recombinant host cells produce less than 5 g/l acetate.

In a fourth aspect, this disclosure provides recombinant host cells that further comprise one or more heterologous nucleic acids that encode a glycolic acid biosynthetic pathway, wherein the pathway enzymes comprise a hydroxypyruvate reductase, a hydroxypyruvate decarboxylase, and a glycoaldehyde dehydrogenase.

In a fifth aspect, this disclosure provides a method for the production of glyceric acid that comprises culturing the recombinant host cells of this disclosure for a sufficient period of time to produce glyceric acid. In some embodiments, the method further comprises an oxygen transfer rate greater than 10 mmol/l/hr. In some embodiments, the method further comprises an operational temperature of between about 25° C. and about 45° C. In some embodiments, the method further comprises a final fermentation broth pH of between about 2.5 and about pH 6. In some embodiments, the method produces a solution containing at least 50 g/l glyceric acid. In some embodiments, the method further comprises providing at least 100 g/l glucose to the recombinant host cell and producing an glyceric acid yield of at least 25%.

In a sixth aspect, this disclosure provides a method for the production of glycolic acid that comprises culturing the recombinant host cells of this disclosure for a sufficient period of time to produce glycolic acid. In some embodiments, the method further comprises an oxygen transfer rate greater than 10 mmol/l/hr. In some embodiments, the method further comprises an operational temperature of between about 25° C. and about 45° C. In some embodiments, the method further comprises a final fermentation broth pH of between about 2.5 and about pH 6. In some embodiments, the method produces a solution containing at least 50 g/l glycolic acid. In some embodiments, the method further comprises providing at least 100 g/l glucose to the recombinant host cell and producing a glycolic acid yield of at least 25%.

In a seventh aspect, this disclosure provides a method to produce glycerate esters comprising the steps of recovering glyceric acid or glycerate salt from fermentation broth, forming the glycerate ester by esterification with supercritical $CO_2$, and purifying said glycerate ester. In various embodiments, the esterification alcohol is methanol, ethanol, isopropyl alcohol, butanol, 3-pentanol, or isobutanol. In various embodiments, the esterification catalyst is $H_2SO_4$. In various embodiments, the glycerate ester is methyl glycerate, ethyl glycerate, butyl glycerate, and 2-ethylhexyl glycerate.

In an eighth aspect, this disclosure provides a deoxydehydration method to produce acrylate esters comprising the steps of converting a glycerate ester to an acrylate ester, and purifying said acrylate ester. In various embodiments, the deoxydehydration alcohol is methanol, ethanol, isopropyl alcohol, butanol, 3-pentanol, or isobutanol. In various embodiments, the deoxydehydration catalyst is selected from the non-limiting group comprising $(NH_4)_6Mo_7O_{24} \cdot 4H_2O$, $MoO_2Cl_2$, $MoO_2(CH_3)_2$, $MoO_2Cl_2$, $MoO_2Br_2$, $(Bu_4N)_2Mo_6O_{19}$, $HReO_4$, $Re_2(CO)_{10}$, $BrRe(CO)_5$, $(Cp*Ru(CO)_2)_2$, or $CH_3ReO_3$. In various embodiments, the deoxyhydration reducing agent is selected from the non-limiting group comprising $PPh_3$, $H_2$, $Na_2SO_3$, benzene, toluene, 5-nonanol, 3-octanol, 2-octanol, 1-butanol, 3-pentanol, 2-methyl-1-butanol, 2-ethylhaxanol, or isopropanol. In various embodiments, the acrylate ester is methyl acrylate, ethyl acrylate, butyl acrylate, and 2-ethylhexyl acrylate.

In a ninth aspect, provided herein is a poly(glycerate carbonate) compound comprising repeat units of formula (I) or a salt thereof:

—[O CH(C(=O)OR¹)CH₂OC(=O)]—

(I) wherein each $R^1$ is independently hydrogen, optionally substituted C1-C5 alkyl, and optionally substituted aryl.

In another aspect, provided herein is a composition comprising a compound prepared comprising the method provided herein.

In another embodiment, the composition provided herein contains non-petrochemical based components, or substantially contains non-petrochemical based components, such as about 25% or more, about 50% or more, about 75% or more, or about 90% or more non-petrochemical based components.

In another aspect, provided herein is an article of manufacture comprising a compound prepared comprising the method provided herein. In another aspect, provided herein is an article of manufacture comprising a compound provided herein. In one embodiment, the article of manufacture is a film. In one embodiment, the article of manufacture is a fiber. In one embodiment, the article of manufacture is a hydrogel. In another aspect, the article is degradable through hydrolytic and biological processes allow stimuli-responsive behavior.

In some embodiments, the recombinant host cells comprise one or more heterologous nucleic acids encoding one or more downstream pathway enzymes that use glycerate as a precursor, substrate, metabolic intermediate, or building block in the production of a downstream product. Non-limiting examples of a downstream product comprise glyceric acid, glycolic acid, acrylic acid, glycerate, glycolate, acrylate, glycerate ester, glycolate ester, acrylate ester, and any molecule that uses glycerate as a precursor, substrate, metabolic intermediate or building block in its synthesis. In some embodiments, the downstream product is an organic acid. In some embodiments, the recombinant host cells produce a downstream product at increased titers, yields and productivities as compared to a parental host cell that does not comprise said heterologous nucleic acids.

In some embodiments, the recombinant host cells further comprise one or more heterologous nucleic acids encoding one or more ancillary gene products (i.e., gene products other than the downstream product pathway enzymes) that improve yields, titers and/or productivities of a downstream product. In particular embodiments, the recombinant host cells further comprise disruptions or deletions of endogenous nucleic acids that improve yields, titers and/or productivities of a downstream product. In some embodiments, the recombinant host cells are capable of producing a downstream product under aerobic conditions. In some embodiments, the recombinant host cells are capable of producing a downstream product under substantially anaerobic conditions.

Any suitable host cell may be used in practice of the methods of the present disclosure, and examples of host cells useful in the compositions and methods provided herein include archaeal, prokaryotic, or eukaryotic cells. In an embodiment of the present disclosure, the recombinant host cell is a prokaryotic cell. In an embodiment of the present disclosure, the recombinant host cell is a eukaryotic cell. In an embodiment of the present disclosure, the recombinant host cell is a *Pichia kudriavzevii* (*P. kudriavzevii*) strain. Methods of construction and genotypes of these recombinant host cells are described herein.

In some embodiments, the recombinant host cell is a yeast cell. In certain embodiments, the yeast cell belongs to the *Issatchenkia orientalis/Pichia fermentans* clade. In some embodiments, the yeast cell belongs to the genus *Pichia*, *Issatchenkia* or *Candida*. In some embodiments, the yeast cell is *Pichia kudriavzevii*. In some embodiments, the yeast cell belongs to the *Saccharomyces* clade. In some embodiments, the yeast cell is *Saccharomyces cerevisiae*. In other embodiments, the recombinant host cell is a prokaryotic cell. In some embodiments, the prokaryotic cell belongs to the genus *Escherichia*, *Corynebacterium*, *Bacillus*, or *Lactococcus*. In some embodiments, the prokaryotic cell is *Escherichia coli*, *Corynebacterium glutamicum*, *Bacillus subtilis*, or *Lactococcus lactis*.

2.1.1 Yeast Cells

In an embodiment of the present disclosure, the recombinant host cell is a yeast cell. Yeast cells are excellent host cells for construction of recombinant metabolic pathways comprising heterologous enzymes catalyzing production of small-molecule products. There are established molecular biology techniques and nucleic acids encoding genetic elements necessary for construction of yeast expression vectors, including, but not limited to, promoters, origins of replication, antibiotic resistance markers, auxotrophic markers, terminators, and the like. Second, techniques for integration/insertion of nucleic acids into the yeast chromosome by homologous recombination are well established. Yeast also offers a number of advantages as an industrial fermentation host. Yeast cells can generally tolerate high concentrations of organic acids and maintain cell viability at low pH and can grow under both aerobic and anaerobic culture conditions, and there are established fermentation broths and fermentation protocols. This characteristic results in efficient product biosynthesis when the host cell is supplied with a carbohydrate carbon source. Also, from a process standpoint, the ability to run fermentations under substantially anaerobic conditions can decrease production cost.

In various embodiments, yeast cells useful in the methods of the present disclosure include yeasts of the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In various embodiments, the yeast cell is of a species selected from the non-limiting group comprising *Candida albicans, Candida ethanolica, Candida guilliermondii, Candida krusei, Candida lipolytica, Candida methanosorbosa, Candida sonorensis, Candida tropicalis, Candida utilis, Cryptococcus curvatus, Hansenula polymorpha, Issatchenkia orientalis, Kluyveromyces lactis, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii* (*P. kudriavzevii*), *Pichia membranaefaciens, Pichia methanolica, Pichia pastoris, Pichia salicaria, Pichia stipitis, Pichia thermotolerans, Pichia trehalophila, Rhodosporidium toruloides, Rhodotorula glutinis, Rhodotorula graminis, Saccharomyces bayanus, Saccharomyces boulardi, Saccharomyces cerevisiae* (*S. cerevisiae*), *Saccharomyces kluyveri, Schizosaccharomyces pombe* (*S. pombe*) and *Yarrowia lipolytica*. This list encompasses yeast in the broadest sense.

The Crabtree phenomenon refers to the capability of yeast cells to convert glucose to alcohol in the presence of high sugar concentrations and oxygen instead of producing biomass via the tricarboxylic acid (TCA) cycle. Yeast cells produce alcohol to prevent growth of competing microorganisms in high sugar environments, which yeast cells can utilize later on when the sugars are depleted. Many yeast can typically use two pathways to produce ATP from sugars: the first involves the conversion of a sugars (via pyruvate) to carbon dioxide via the TCA cycle, and the second involves the conversion of sugars (via pyruvate) to ethanol. Yeast cells that display a Crabtree effect (known as Crabtree-positive yeast cells) are able to simultaneously use both pathways. Yeast cells that do not display a Crabtree effect (known as Crabtree-negative yeast cells) only convert pyruvate to ethanol when oxygen is absent. In some embodiments of the present disclosure, the host cell is a Crabtree-positive yeast cell. In other embodiments, the host cell is a Crabtree-negative yeast cell. In certain embodiments, the host cell displays a phenotype along a continuum of traits between Crabtree-positive and Crabtree-negative and is thus neither exclusively a Crabtree-positive yeast cell nor Crabtree negative yeast cell. It is advantageous to use a Crabtree-negative yeast or a yeast with perceptible Crabtree-negative tendencies or traits to produce glyceric acid because high glucose concentrations can be maintained during product biosynthesis without ethanol accumulation; ethanol is an undesired byproduct in glyceric acid production. *P. kudriavzevii* does not produce appreciable amounts of ethanol from pyruvate at high glucose concentrations in the presence of oxygen, and as such is a Crabtree-negative yeast. In some embodiments, the host cell is *P. kudriavzevii*.

In certain embodiments, the recombinant yeast cells provided herein are engineered by the introduction of one or more genetic modifications (including, for example, heterologous nucleic acids encoding enzymes and/or the disruption of native nucleic acids encoding enzymes) into a Crabtree-negative yeast cell. In certain of these embodiments, the host cell belongs to the *Pichia/Issatchenkia/Saturnispora/Dekkera* clade. In certain of these embodiments, the host cell belongs to the genus selected from the group comprising *Pichia, Issatchenkia,* or *Candida*. In certain embodiments, the host cell belongs to the genus *Pichia*, and in some of these embodiments the host cell is *P. kudriavzevii*. Members of the *Pichia/Issatchenkia/Saturnispora/Dekkera* or the *Saccharomyces* clade are identified by analysis of their 26S ribosomal DNA using the methods described by Kurtzman C. P., and Robnett C. J., ("Identification and Phylogeny of Ascomycetous Yeasts from Analysis of Nuclear Large Subunit (26S) Ribosomal DNA Partial Sequences", Atonie van Leeuwenhoek 73(4):331-371; 1998). Kurtzman and Robnett report analysis of approximately 500 ascomycetous yeasts were analyzed for the extent of divergence in the variable D1/D2 domain of the large subunit (26S) ribosomal DNA. Host cells encompassed by a clade exhibit greater sequence identity in the D1/D2 domain of the 26S ribosomal subunit DNA to other host cells within the clade as compared to host cells outside the clade. Therefore, host cells that are members of a clade (for example, the *Pichia/Issatchenkia/Saturnispora/Dekkera* or *Saccharomyces* clades) can be identified using the methods of Kurtzman and Robnett.

In certain embodiments of the present disclosure, the recombinant host cells are engineered by introduction of one or more genetic modifications into a Crabtree-positive yeast cell. In certain of these embodiments, the host cell belongs to the *Saccharomyces* clad. In certain of these embodiments, the host cell belongs to a genus selected from the group comprising *Saccharomyces, Schizosaccharomyces, Brettanomyces, Torulopsis, Nematospora* and *Nadsonia*. In certain embodiments, the host cell belongs to the genus *Saccharomyces*, and in one of these embodiments the host cell is *S. cerevisiae*.

2.1.2 Eukaryotic Cells

In addition to yeast cells, other eukaryotic cells are also suitable for use in accordance with methods of the present disclosure, so long as the engineered host cell is capable of growth and/or product formation. Illustrative examples of eukaryotic host cells provided by the present disclosure include, but are not limited to cells belonging to the genera *Aspergillus, Crypthecodinium, Cunninghamella, Entomophthora, Mortierella, Mucor, Neurospora, Pythium, Schizochytrium, Thraustochytrium, Trichoderma,* and *Xanthophyllomyces*. Examples of eukaryotic strains include, but are not limited to: *Aspergillus niger, Aspergillus oryzae, Cryptheco-dinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous*.

2.1.3 Archaeal Cells

Archaeal cells are also suitable for use in accordance with methods of the present disclosure, and in an embodiment of the present disclosure, the recombinant host cell is an archaeal cell. Illustrative examples of recombinant archaea host cells provided by the present disclosure include, but are not limited to, cells belonging to the genera: *Aeropyrum, Archaeglobus, Halobacterium, Methanococcus, Methanobacterium, Pyrococcus, Sulfolobus,* and *Thermoplasma*. Examples of archaea strains include, but are not limited to *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi,* and *Aeropyrum pernix*.

2.1.4 Prokaryotic Cells

In an embodiment of the present disclosure, the recombinant host cell is a prokaryotic cell. Prokaryotic cells are suitable host cells for construction of recombinant metabolic pathways comprising heterologous enzymes catalyzing production of small-molecule products. Illustrative examples of recombinant prokaryotic host cells include, but are not limited to, cells belonging to the genera *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Pantoea, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus,* and *Zymomonas*. Examples of prokaryotic strains include, but are not limited to, *Bacillus subtilis* (*B. subtilis*), *Brevibacterium ammoniagenes, Bacillus amyloliquefacines, Brevibacterium ammoniagenes, Brevibacterium immariophilum, Clostridium acetobutylicum, Clostridium beigerinckii, Corynebacterium glutamicum* (*C. glutamicum*), *Enterobacter sakazakii, Escherichia coli* (*E. coli*), *Lactobacillus acidophilus, Lactococcus lactis, Mesorhizobium loti, Pantoea ananatis* (*P. ananatis*), *Pseudomonas aeruginosa, Pseudomonas mevalonii, Pseudomonas pudita, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei,* and *Staphylococcus aureus*.

2.2 Glyceric Acid Pathway

Provided herein in certain embodiments are recombinant host cells having at least one active glyceric acid pathway from a glycolytic intermediate to glycerate. Recombinant host cells having an active glyceric acid pathway are used as described herein to produce one or more active enzymes necessary to catalyze each metabolic reaction in a glyceric acid pathway, and therefore are capable of producing glyceric acid in measurable yields and/or titers when cultured under suitable conditions. Recombinant host cells having a glyceric acid pathway comprise one or more heterologous nucleic acids encoding glyceric acid pathway enzyme(s) and are capable of producing glycerate. In some embodiments, the recombinant host cell is *Pichia kudriavzevii*.

Recombinant host cells may employ combinations of metabolic reactions for biosynthetically producing the compounds of the present disclosure. The biosynthesized compounds produced by the recombinant host cells comprise glycerate, glyceric acid, and the intermediates, products and derivatives of the glyceric acid pathway. The biosynthesized compounds can be produced intracellularly and/or secreted into the fermentation medium.

2.2.1 Glyceric Acid Pathway Enzymes

The glyceric acid pathway described herein produces glycerate from glucose with the following balanced, stoichiometric equation:

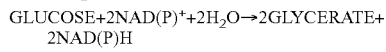
GLUCOSE+2NAD(P)$^+$+2H$_2$O→2GLYCERATE+ 2NAD(P)H

In many embodiments, recombinant host cells of the present disclosure comprise a glyceric acid pathway that proceeds via (1) 3-phosphoglycerate (3-PG; synonymous with glycerate-3-phosphate and 3-phosphoglyceric acid); or, (2) 2-phosphoglycerate (2-PG; synonymous with glycerate-2-phosphate and 2-phosphoglyceric acid); or, (3) 3-PG and 2-PG (Table 1). In some embodiments, the recombinant host cells comprise a glyceric acid pathway that proceeds via 3-PG, wherein a 3-PG phosphatase (EC #3.1.3.38) converts one molecule of 3-PG and one molecule of water into one molecule of glycerate and one molecule of orthophosphate. In other embodiments, the recombinant host cells comprise a glyceric acid pathway that proceeds via 2-PG, wherein a 2-PG phosphatase (EC #3.1.3.20) converts one molecule of 2-PG and one molecule of water into one molecule of glycerate and one molecule of orthophosphate. In some embodiments, the recombinant host cells comprise a glyceric acid pathway that proceeds via 2-PG. In some embodiments, the recombinant host cells comprise a glyceric acid pathway that proceeds via both 3-PG and 2-PG. In some embodiments, the recombinant host cells comprise a glyceric acid pathway with one or more enzymes that are derived from a phosphoglycerate monoester hydrolase (EC #3.1.3.X).

The advantaged thermodynamics of the pathway will help to achieve high glyceric acid yields, titers and/or productivities, and/or high downstream product yields, titers and/or productivities. The conversion of glucose to glycerate via the glyceric acid pathways described herein has a calculated change in Gibbs free energy of −73.8+/−3.4 kJ/mol (i.e., $\Delta_r G'''$ calculated at 1 mM metabolite concentrations, 25° C., pH 7.0, and 0.1 M ionic strength; conditions typically observed in yeast), a negative value indicative of a strong driving force that pushes the reaction to completion, favoring product formation. Due to its mechanism of action, the 3-PG/2-PG phosphatase-catalyzed reaction should also be irreversible, although this disclosure is not bound by any particular method or mechanism. Additionally, net formation of NAD(P)H via said reaction can be used by recombinant host cells for ATP generation in the electron transport chain, thereby minimizing the amount of additional glucose used to support product export and cellular maintenance.

TABLE 1

Enzymes in a glycerate-producing reaction

| EC # | Enzyme name | Reaction catalyzed |
|---|---|---|
| 3.1.3.38 | 3-Phosphoglycerate phosphatase | 3-Phosphoglycerate + H$_2$O → Glycerate + orthophosphate |
| 3.1.3.20 | 2-Phosphoglycerate phosphatase | 2-Phosphoglycerate + H$_2$O → Glycerate + orthophosphate |
| 3.1.3.X | A phosphoglycerate monoester hydrolase | A phosphoglycerate monoester substrate (with or without other reactants) → a glycerate monoester + orthophosphate (with or without other products) |

2.2.1.1 3-Phosphoglycerate Phosphatase

The 3-PG phosphatase (EC #3.1.3.38) described herein catalyzes a one-step reaction of the glyceric acid pathway, wherein one molecule of 3-PG and one molecule of water are converted to one molecule of glycerate and one molecule of orthophosphate (Table 1).

Any enzyme is suitable for use in accordance with this disclosure so long as the enzyme is capable of catalyzing said 3-PG phosphatase reaction described above. In an embodiment of the present disclosure, a glyceric acid pathway comprising a 3-PG phosphatase is calculated to thermodynamically favor the conversion of glucose to glycerate. In some embodiments, recombinant host cells comprise one or more heterologous nucleic acids encoding a 3-PG phosphatase wherein said recombinant host cells are capable of producing glycerate. In certain embodiments, recombinant host cells comprise one or more heterologous nucleic acids encoding a 3-PG phosphatase, wherein the heterologous nucleic acid is expressed in sufficient amounts to produce glycerate. In various embodiments, recombinant host cells may comprise multiple copies of a single heterologous nucleic acid and/or multiple copies of two or more heterologous nucleic acids. Recombinant host cells comprising multiple heterologous nucleic acids may comprise any number of heterologous nucleic acids. Although phosphatase enzymes are ubiquitous in nature, no enzyme is known to specifically catalyze this reaction. Some substrate-promiscuous phosphatases have been reported with activity towards 3-PG, but these enzymes also dephosphorylate a broad range of glycolytic intermediates and other phosphorylated compounds, and are either not specific enough or not active enough toward 3-PG. Further, not all phosphatases are substrate-promiscuous, and many substrate-specific phosphatases have also been characterized with good activity toward compounds structurally similar to 3-PG, including phosphoserine (EC #3.1.3.3), glycerol-3-phosphate (EC #3.1.3.21) and phosphoglycolate (EC #3.1.3.18). Thus, although any enzyme, particularly, any phosphoglycerate monoester hydrolase (EC #3.1.3.X), is suitable for use in accordance with this disclosure so long as the enzyme is capable of catalyzing said 3-PG phosphatase reaction, not any such natural enzyme is able to catalyze said reaction with sufficient specificity or efficiency to produce reasonable product yields and/or titers. In many embodiments, the 3-PG phosphatase has one or more active site mutations. In some embodiments, the one or more active site mutations lies in the active site, catalytic site, or substrate binding site.

Methods for identifying and improving enzymes towards desired 3-PG phosphatase activity are disclosed below in section 2.2.2 (on methods to identify and/or improve enzymes in the glyceric acid pathway). The methods described below for protein mutagenesis, identification, expression, purification, and characterization are methods widely-practiced by practitioners skilled in the art, who will appreciate that a wide variety of commercial solutions are available for such endeavors. Briefly, methods that may be used (as described in section 2.2.2) comprise random and rational mutagenesis methods such as site-specific mutagenesis, error-prone PCR, and directed evolution. Libraries of mutated genes or strains are generated, and mutagenized proteins are characterized, and integrated into the genome of recombinant host cells for further strain characterization. The methods disclosed may be adapted as needed depending on the target enzyme properties desired.

In some embodiments, the 3-PG phosphatase enables improved pathway flux. In some embodiments, the 3-PG phosphatase enables increased yield, titer and/or productivity. In some embodiments, the 3-PG phosphatase enables increased substrate specificity. In some embodiments, the 3-PG phosphatase displays improved kinetic properties, such as $K_m$ and $k_{cat}$. In some embodiments, the 3-PG phosphatase is a product of one or more protein engineering cycles. In some embodiments, the 3-PG phosphatase comprises one or more point mutations. In some embodiments, the 3-PG phosphatase has improved $K_m$ and/or $k_{cat}$ for the substrate 3-PG. In some embodiments, the 3-PG phosphatase has $K_m \leq 3$ mM with 3-PG as substrate. In some embodiments, the 3-PG phosphatase has $k_{cat} \geq 10$ per second with 3-PG as substrate.

In some embodiments, the 3-PG phosphatase is derived from a phosphoserine phosphatase (EC #3.1.3.3), glycerol-1-phosphatase (EC #3.1.3.21), or phosphoglycolate phosphatase (EC #3.1.3.18).

In some embodiments, the 3-PG phosphatase is derived from a bacterial source. In many of these embodiments, the 3-PG phosphatase is derived from a cell belonging to a genus selected from the group comprising Escherichia, Mycobacterium, Haemophilus and Synechococcus. Non-limiting examples of bacterial enzymes comprise Escherichia coli UniProt ID: P32662, Mycobacterium avium UniProt ID: AOQJI1, Haemophilus somnus UniProt ID: QOI1W8, Synechococcus elongatus UniProt ID: Q55320, and Escherichia coli UniProt ID: P27848.

In some embodiments, the 3-PG phosphatase is derived from the Escherichia coli phosphoglycolate phosphatase (abbv. EcGPH; UniProt ID: P32662; SEQ ID NO: 1). EcGPH catalyzes the conversion of one molecule of 2-phosphoglycolate (2P-Gly) and one molecule of water to one molecule of glycolate and one molecule of phosphate. 2P-Gly and 3-PG are structurally similar, making EcGPH a good starting point for engineering a 3-PG phosphatase. In various embodiments, the 3-PG phosphatase derived from a 2P-Gly phosphatase has one or more active site mutations resulting in increased enzyme activity and/or specificity toward 3-PG.

In some embodiments, the 3-PG phosphatase is derived from the Mycobacterium avium phosphoserine phosphatase (abbv. MaSERB; UniProt ID: AOQJI1; SEQ ID NO: 2; PDB: AOQJI1). MaSERB catalyzes the conversion of one molecule of O-phospho-L(or D)-serine and one molecule of water to one molecule of L(or D)-serine and one molecule of phosphate. O-phospho-L(or D)-serine and 3-PG are structurally similar, making MaSERB a good starting point for engineering a 3-PG phosphatase. In various embodiments, the 3-PG phosphatase derived from MaSERB has one or more active site mutations comprising E196S, T, N, Q, A, V, I or L; D189S, T, N, Q, A, V, I or L; or any combination thereof.

In some embodiments, the 3-PG phosphatase is derived from the Haemophilus somnus phosphoglycolate phosphatase (abbv. HsGPH; UniProt ID: QOI1W8; SEQ ID NO: 3; PDB: 2HSZ). HsGPH catalyzes the conversion of one molecule of 2P-Gly and one molecule of water to one molecule of glycolate and one molecule of phosphate. In various embodiments, the 3-PG phosphatase derived from HsGPH has one or more active site mutations at the amino acid positions comprising A49, Q178, N179, N199, Y200, N201, or any combination thereof.

In some embodiments, the 3-PG phosphatase is derived from the Synechococcus elongates alkaline phosphatase (abbv. SePHOV; UniProt ID: Q55320, SEQ ID NO: 6). SePHOV catalyzes the conversion of phosphate monoester and water to alcohol and phosphate. In various embodiments, the 3-PG phosphatase is without an N-terminal signal sequence. In some embodiments, the 3-PG phosphatase is without its first 20 amino acids. In various embodiments, the 3-PG phosphatase has one or more active site mutations In some embodiments, the 3-PG phosphatase is derived from the Escherichia coli phosphosugar phosphatase (abbv. EcYIGL; UniProt ID: P27848; SEQ ID NO: 8). EcYIGL catalyzes the conversion of one molecule of pyridoxal 5'-phosphate and one molecule of water to one molecule of pyridoxal and one molecule of phosphate. In various embodiments, the 3-PG phosphatase derived from EcYIGL has one or more active site mutations.

In some embodiments, the 3-PG phosphatase is derived from a eukaryotic source. In many of these embodiments, the 3-PG phosphatase is derived form a cell belonging to a genus selected from the group comprising Saccharomyces, Pichia, and Homo. In some embodiments, the recombinant host cell is Pichia kudriavzevii.

Non-limiting examples of eukaryotic enzymes comprise Saccharomyces cerevisiae UniProt ID: P40106, Saccharomyces cerevisiae UniProt ID: P19881, Saccharomyces cerevisiae UniProt ID: A6ZX98, Saccharomyces cerevisiae UniProt ID: G2WBT3, Saccharomyces cerevisiae UniProt ID: $C_7GJQ5$, Saccharomyces cerevisiae UniProt ID: P36151, Pichia kudriavzevii UniProt ID: A0A1Z8JUP5, Pichia kudriavzevii UniProt ID: A0A099NZ38, Pichia kudriavzevii UniProt ID: A0A1Z8JN52, and Homo sapiens UniProt ID: A6NDG6.

In some embodiments, the 3-PG phosphatase is derived from the Saccharomyces cerevisiae glycerol-1-phosphate phosphatase (abbv. ScGPP2; UniProt ID: P40106; SEQ ID NO: 4). ScGPP2 catalyzes the conversion of one molecule of glycerol-1-phosphate and one molecule of water to one molecule of glycerol and one molecule of phosphate. In various embodiments, the 3-PG phosphatase derived from ScGPP2 has one or more active site mutations comprising N204R, H, K, Q, A or Y.

In some embodiments, the 3-PG phosphatase is derived from the Homo sapiens glycerol-3-phosphate phosphatase (abbv. HsPGP; UniProt ID: A6NDG6; SEQ ID NO: 5). HsPGP catalyzes the conversion of glycerol-3-phosphate and water to glycerol and phosphate. In various embodiments, the 3-PG phosphatase has one or more active site mutations.

In some embodiments, the 3-PG phosphatase is derived from Saccharomyces cerevisiae 4-nitrophenylphosphatase (abbv. ScPHO13; UniProt ID: P19881; SEQ ID NO: 9). ScPHO13 catalyzes the conversion of one molecule of 4-nitrophenyl phosphate and one molecule of water to one molecule of 4-nitrophenol and one molecule of phosphate. In some embodiments, the 3-PG phosphatase derived from ScPHO13 has one or more active site mutations.

In some embodiments, the 3-PG phosphatase is derived from Pichia kudriavzevii Pho13 protein (abbv. PkPHO13; UniProt ID: A0A1Z8JUP5; SEQ ID NO: 10). PkPHO13 catalyzes the conversion of one molecule of 4-nitrophenyl phosphate and one molecule of water to one molecule of 4-nitrophenol and one molecule of phosphate. In some embodiments, the 3-PG phosphatase derived from PkPHO13 has one or more active site mutations.

In some embodiments, the 3-PG phosphatase is derived from Pichia kudriavzevii ORF64 protein (abbv. PkORF64; UniProt ID: A0A099NZ38; SEQ ID NO: 11). In some embodiments, the 3-PG phosphatase derived from PkORF64 has one or more active site mutations.

In some embodiments, the 3-PG phosphatase is derived from Pichia kudriavzevii ORF423 protein (abbv. PkORF423; UniProt ID: A0A1Z8JN52; SEQ ID NO: 12). In some embodiments, the 3-PG phosphatase derived from PkORF423 has one or more active site mutations.

In some embodiments, the 3-PG phosphatase is derived from *Saccharomyces cerevisiae* uncharacterized protein YKR070W (abbv. ScYKR070W; UniProt ID: P36151; SEQ ID NO: 13). In some embodiments, the 3-PG phosphatase derived from PkORF423 has one or more active site mutations.

In some embodiments, the 3-PG phosphatase has a $K_m$ of less than about 5 mM with 3-PG as the substrate. In some embodiments, the 3-PG phosphatase has a $K_m$ for 3-PG that is less than $K_m$ for other glycolytic intermediates. In some embodiments, the 3-PG phosphatase has a $k_{cat}$ of greater than about 10 turnovers per second with 3-PG as the substrate. In some embodiments, the 3-PG phosphatase has a $k_{cat}$ for 3-PG that is greater than the $k_{cat}$ for other glycolytic intermediates. In some embodiments, the 3-PG phosphatase has an improved $k_{cat}/K_m$ compared to the protein that it was derived from.

In many embodiments, recombinant host cells comprise one or more heterologous nucleic acids encoding a 3-PG phosphatase wherein said recombinant host cells are capable of producing glycerate. In various embodiments, proteins suitable for use in accordance with methods of the present disclosure have 3-PG phosphatase activity and comprise an amino acid sequence with at least 40%, at least 50%, at least 60%, at least 70%, at least 80%, at least 90%, or at least 95% sequence identity with SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, or SEQ ID NO: 13. In many embodiments, the recombinant host cell is a *P. kudriavzevii* strain.

The present disclosure also provides consensus sequences (defined above) useful in identifying and/or constructing glyceric acid pathway enzymes suitable for use in accordance with the methods of the present disclosure. In various embodiments, these consensus sequences comprise active site amino acid residues involved in substrate recognition and reaction catalysis, as described herein. Thus, an enzyme encompassed by a consensus sequence provided herein has an enzymatic activity that is identical, or essentially identical, or at least substantially similar with respect to ability to catalyze the reaction performed by one of the enzymes exemplified herein. For example, a 3-PG phosphatase encompassed by a 3-PG phosphatase consensus sequence provided herein has an enzymatic activity that is identical, or essentially identical, or at least substantially similar with respect to ability to convert one molecule of 3-PG and one molecule of water to one molecule of glycerate and one molecule of orthophosphate. As noted above, any protein substantially homologous to 3-PG phosphatase as described herein can be used in a recombinant host cell of the present disclosure.

The 3-PG phosphatase consensus sequence #1 (SEQ ID NO: 7) provides the sequence of amino acids in which each position identifies the amino acid (if a specific amino acid is identified) or a subset of amino acids (if a position is identified as variable) most likely to be found at a specific position in a 3-PG phosphatase. Many amino acids in SEQ ID NO: 7 are highly conserved and 3-PG phosphatases suitable for use in accordance with the methods of the present disclosure will comprise a substantial number, and sometimes all, of these highly conserved amino acids at positions aligning with the location of the indicated amino acid in SEQ ID NO: 7. In various embodiments, proteins suitable for use in accordance with the methods of the present disclosure have 3-PG phosphatase activity and comprise an amino acid sequence with at least 40%, at least 50%, at least 60%, or at least 70% sequence identity with SEQ ID NO: 7. For example, the *Ashbya aceri* yeast 4-nitrophenylphosphatase UniProt ID: R9XA12 sequence is 62% identical to consensus sequence #1 SEQ ID NO: 7, and is therefore encompassed by consensus sequence #1 SEQ ID NO: 7. The highly conserved amino acids in SEQ ID NO: 7 are D25, F27, F29, D30, C31, D32, G33, V34, W36, P43, E47, L52, K57, F61, V62, T63, N64, N65, K68, S69, R70, Y73, K76, F77, G81, F91, S93, A98, G118, G121, E125, L126, G130, G135, D161, V167, G170, L171, Y177, L187, F196, T199, N200, D202, T204, P206, G209, G214, A215, G216, G235, K236, P237, M241, I245, M261, G263, D264, R265, T268, D269, F272, G273, L278, T281, V284, L285, and G287. Example 5 demonstrates how recombinant host cells comprising many different heterologous nucleic acids encoding 3-PG phosphatase enzymes homologous SEQ ID NO: 7 increase glyceric acid production as compared to parental host cells that did not comprise said genetic modifications.

In other embodiments, any protein that shares the specific function of 3-PG phosphatase as described herein can be used in a recombinant host cell of the disclosure despite comprising insufficient sequence identity (i.e., less than 40% identity) with the 3-PG phosphatase consensus sequence.

2.2.1.2 2-Phosphoglycerate Phosphatase

In addition to 3-PG phosphatase enzymes, other enzymes can be used to convert glycolytic intermediates into glycerate. In some embodiments, the recombinant host cells comprise a 2-PG phosphatase; in these embodiments, the 2-PG phosphatase (EC #3.1.3.20) catalyzes another step in the glyceric acid pathway, wherein one molecule of 2-PG and one molecule of water are converted to one molecule of glycerate and one molecule of orthophosphate (Table 1). In some embodiments where recombinant host cells comprise a 3-PG phosphatase, said recombinant host cells further comprise a 2-PG phosphatase.

Any enzyme is suitable for use in accordance with this disclosure so long as the enzyme is capable of catalyzing said 2-PG phosphatase reaction described above. In an embodiment of the present disclosure, a glyceric acid pathway comprising a 2-PG phosphatase is calculated to thermodynamically favor the conversion of glucose to glycerate. In certain embodiments, recombinant host cells comprise one or more heterologous nucleic acids encoding a 2-PG phosphatase, wherein said recombinant host cells are capable of producing glycerate. In various embodiments, recombinant host cells may comprise multiple copies of a single heterologous nucleic acid and/or multiple copies of two or more heterologous nucleic acids. Recombinant host cells comprising multiple heterologous nucleic acids may comprise any number of heterologous nucleic acids.

Although phosphatase enzymes are ubiquitous in nature, no enzyme is known to specifically catalyze this reaction. Similar to 3-PG phosphatase, the 2-PG phosphatase of the present disclosure may be derived from a variety of phosphatases. Some substrate-promiscuous phosphatases have been reported with activity towards 2-PG, but these enzymes also dephosphorylate a broad range of glycolytic intermediates and other phosphorylated compounds, and are either not specific enough or not active enough toward 2-PG. Further, not all phosphatases are substrate-promiscuous, and many substrate-specific phosphatases have also been characterized with good activity toward compounds structurally similar to 2-PG, including phosphoserine (EC #3.1.3.3), glycerol-3-phosphate (EC #3.1.3.21) and phosphoglycolate (EC #3.1.3.18). Thus, although any enzyme, particularly, any phosphoglycerate monoester hydrolase (EC #3.1.3.X), is suitable for use in accordance with this disclosure so long as the enzyme is capable of catalyzing said 2-PG phosphatase reaction, not any such natural enzyme is able to catalyze said reaction with sufficient specificity or efficiency to produce reasonable product yields and/or titers. In many embodiments, the 2-PG phosphatase has one or more active site mutations. In some embodiments, the one or more active site mutations lies in the active site, catalytic site, or substrate binding site.

Methods for identifying and improving enzymes towards desired 2-PG phosphatase activity are disclosed below in section 2.2.2. The methods described herein for protein mutagenesis, expression, purification and characterization are methods widely-practiced by practitioners skilled in the art, who will appreciate that a wide variety of commercial solutions are available for such endeavors. Briefly, methods that may be used (as described in section 2.2.2) comprise random and rational mutagenesis methods such as site-specific mutagenesis, error-prone PCR, and directed evolution. Libraries of mutated genes or strains are generated, and mutagenized proteins are characterized, and integrated into the genome of recombinant host cells for further strain characterization. The methods disclosed may be adapted as needed depending on the target enzyme properties desired.

In some embodiments, the 2-PG phosphatase enables improved pathway flux. In some embodiments, the 2-PG phosphatase enables increased yield, titer and/or productivity. In some embodiments, the 2-PG phosphatase enables increased substrate specificity. In some embodiments, the 2-PG phosphatase displays improved kinetic properties, such as $K_m$ and $k_{cat}$. In some embodiments, the 2-PG phosphatase is a product of one or more protein engineering cycles. In some embodiments, the 2-PG phosphatase comprises one or more point mutations. In some embodiments, the 2-PG phosphatase has improved $K_m$ and/or $k_{cat}$ for the substrate 2-PG. In some embodiments, the 2-PG phosphatase has $K_m \leq 3$ mM with 2-PG as substrate. In some embodiments, the 2-PG phosphatase has $k_{cat} \geq 10$ per second with 2-PG as substrate. In some embodiments, the 2-PG phosphatase has an improved $k_{cat}/K_m$ compared to the protein that it was derived from.

In some embodiments, the 3-PG phosphatase is derived from a phosphoserine phosphatase (EC #3.1.3.3), glycerol-1-phosphatase (EC #3.1.3.21), or phosphoglycolate phosphatase (EC #3.1.3.18).

In some embodiments, the 2-PG phosphatase is derived from a bacterial source. In many of these embodiments, the 2-PG phosphatase is derived from a cell belonging to a genus selected from the group comprising *Escherichia*, *Mycobacterium*, *Haemophilus* and *Synechococcus*. Non-limiting examples of bacterial enzymes comprise *Escherichia coli* UniProt ID: P32662, *Mycobacterium avium* UniProt ID: AOQJI1, *Haemophilus somnus* UniProt ID: QOI1W8, *Synechococcus elongatus* UniProt ID: Q55320, and *Escherichia coli* UniProt ID: P27848.

In some embodiments, the 2-PG phosphatase is derived from the *Escherichia coli* phosphoglycolate phosphatase (abbv. EcGPH; UniProt ID: P32662; SEQ ID NO: 1). EcGPH catalyzes the conversion of one molecule of 2-phosphoglycolate (2P-Gly) and one molecule of water to one molecule of glycolate and one molecule of phosphate. 2P-Gly and 2-PG are structurally similar, making EcGPH a good candidate for mutagenesis. In various embodiments, the 2-PG phosphatase has one or more active site mutations.

In some embodiments, the 2-PG phosphatase is derived from the *Mycobacterium avium* phosphoserine phosphatase (abbv. MaSERB; UniProt ID: AOQJI1; SEQ ID NO: 2; PDB: AOQJI1). MaSERB catalyzes the conversion of one molecule of O-phospho-L(or D)-serine and one molecule of water to one molecule of L(or D)-serine and one molecule of phosphate. 0-phospho-L(or D)-serine and 2-PG are structurally similar, making MaSERB a good candidate for mutagenesis. In various embodiments, the 3-PG phosphatase has one or more active site mutations comprising E196S, T, N, Q, A, V, I or L; D189S, T, N, Q, A, V, I or L; or any combination thereof.

In some embodiments, the 2-PG phosphatase is derived from the *Haemophilus somnus* phosphoglycolate phosphatase (abbv. HsGPH; UniProt ID: QOI1W8; SEQ ID NO: 3; PDB: 2HSZ). HsGPH catalyzes the conversion of one molecule of 2P-Gly and one molecule of water to one molecule of glycolate and one molecule of phosphate. In various embodiments, the 3-PG phosphatase derived from HsGPH has one or more active site mutations at the amino acid positions comprising A49, Q178, N179, N199, Y200, N201, or any combination thereof.

In some embodiments, the 2-PG phosphatase is derived from the *Synechococcus elongates* alkaline phosphatase (abbv. SePHOV; UniProt ID: Q55320, SEQ ID NO: 6). SePHOV catalyzes the conversion of phosphate monoester and water to alcohol and phosphate. In various embodiments, the 2-PG phosphatase is without an N-terminal signal sequence. In some embodiments, the 2-PG phosphatase is without its first 20 amino acids. In various embodiments, the 2-PG phosphatase has one or more active site mutations In some embodiments, the 2-PG phosphatase is derived from the *Escherichia coli* phosphosugar phosphatase (abbv. EcYIGL; UniProt ID: P27848; SEQ ID NO: 8). EcYIGL catalyzes the conversion of one molecule of pyridoxal 5'-phosphate and one molecule of water to one molecule of pyridoxal and one molecule of phosphate. In various embodiments, the 2-PG phosphatase derived from EcYIGL has one or more active site mutations.

In some embodiments, the 2-PG phosphatase is derived from a eukaryotic source. In many of these embodiments, the 2-PG phosphatase is derived form a cell belonging to a genus selected from the group comprising *Saccharomyces*, *Pichia*, and *Homo*.

Non-limiting examples of eukaryotic enzymes comprise *Saccharomyces cerevisiae* UniProt ID: P40106, *Saccharomyces cerevisiae* UniProt ID: P19881, *Saccharomyces cerevisiae* UniProt ID: A6ZX98, *Saccharomyces cerevisiae* UniProt ID: G2WBT3, *Saccharomyces cerevisiae* UniProt ID: C7GJQ5, *Saccharomyces cerevisiae* UniProt ID: P36151, *Pichia kudriavzevii* UniProt ID: A0A1Z8JUP5, *Pichia kudriavzevii* UniProt ID: A0A099NZ38, *Pichia kudriavzevii* UniProt ID: A0A1Z8JN52, and *Homo sapiens* UniProt ID: A6NDG6.

In some embodiments, the 2-PG phosphatase is derived from the *Saccharomyces cerevisiae* glycerol-1-phosphate phosphatase (abbv. ScGPP2; UniProt ID: P40106; SEQ ID NO: 4). ScGPP2 catalyzes the conversion of one molecule of glycerol-1-phosphate and one molecule of water to one molecule of glycerol and one molecule of phosphate. In various embodiments, the 2-PG phosphatase derived from ScGPP2 has one or more active site mutations comprising N204R, H, K, Q, A or Y.

In some embodiments, the 2-PG phosphatase is derived from the *Homo sapiens* glycerol-3-phosphate phosphatase (abbv. HsPGP; UniProt ID: A6NDG6; SEQ ID NO: 5). HsPGP catalyzes the conversion of glycerol-3-phosphate and water to glycerol and phosphate. In various embodiments, the 2-PG phosphatase has one or more active site mutations.

In some embodiments, the 2-PG phosphatase is derived from *Saccharomyces cerevisiae* 4-nitrophenylphosphatase (abbv. ScPHO13; UniProt ID: P19881; SEQ ID NO: 9). ScPHO13 catalyzes the conversion of one molecule of 4-nitrophenyl phosphate and one molecule of water to one molecule of 4-nitrophenol and one molecule of phosphate. In some embodiments, the 2-PG phosphatase derived from ScPHO13 has one or more active site mutations.

In some embodiments, the 2-PG phosphatase is derived from *Pichia kudriavzevii* Pho13 protein (abbv. PkPHO13; UniProt ID: A0A1Z8JUP5; SEQ ID NO: 10). PkPHO13 catalyzes the conversion of one molecule of 4-nitrophenyl phosphate and one molecule of water to one molecule of 4-nitrophenol and one molecule of phosphate. In some embodiments, the 3-PG phosphatase derived from ScPHO13 has one or more active site mutations.

In some embodiments, the 2-PG phosphatase is derived from *Pichia kudriavzevii* ORF64 protein (abbv. PkORF64; UniProt ID: A0A099NZ38; SEQ ID NO: 11). In some embodiments, the 3-PG phosphatase derived from PkORF64 has one or more active site mutations.

In some embodiments, the 2-PG phosphatase is derived from *Pichia kudriavzevii* ORF423 protein (abbv. PkORF423; UniProt ID: A0A1Z8JN52; SEQ ID NO: 12). In some embodiments, the 3-PG phosphatase derived from PkORF423 has one or more active site mutations.

In some embodiments, the 2-PG phosphatase is derived from *Saccharomyces cerevisiae* uncharacterized protein YKR070W (abbv. ScYKR070W; UniProt ID: P36151; SEQ ID NO: 13). In some embodiments, the 2-PG phosphatase derived from PkORF423 has one or more active site mutations.

In some embodiments, the 2-PG phosphatase has a $K_m$ of less than about 5 mM with 2-PG as the substrate. In some embodiments, the 2-PG phosphatase has a $K_m$ for 2-PG that is less than $K_m$ for other glycolytic intermediates. In some embodiments, the 2-PG phosphatase has a $k_{cat}$ of greater than about 10 turnovers per second with 2-PG as the substrate. In some embodiments, the 2-PG phosphatase has a $k_{cat}$ for 2-PG that is greater than the $k_{cat}$ for other glycolytic intermediates.

In many embodiments, recombinant host cells comprise one or more heterologous nucleic acids encoding a 2-PG phosphatase wherein said recombinant host cells are capable of producing glycerate. In various embodiments, proteins suitable for use in accordance with methods of the present disclosure have 2-PG phosphatase activity and comprise an amino acid sequence with at least 40%, at least 50%, at least 60%, at least 70%, at least 80%, at least 90%, or at least 95% sequence identity with SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, or SEQ ID NO: 13. In many embodiments, the recombinant host cell is a *P. kudriavzevii* strain.

A consensus sequence is useful in identifying 2-PG phosphatases suitable for use in accordance with the methods of the present disclosure. A 2-PG phosphatase encompassed by a 2-PG phosphatase consensus sequence provided herein has an enzymatic activity that is identical, or essentially identical, or at least substantially similar with respect to ability to convert one molecule of 2-PG and one molecule of water to one molecule of glycerate and one molecule of orthophosphate. Thus, any protein substantially homologous to 2-PG phosphatase as described herein can be used in a recombinant host cell of the present disclosure.

Consensus sequence #1 (SEQ ID NO: 7) provides the sequence of amino acids in which each position identifies the amino acid (if a specific amino acid is identified) or a subset of amino acids (if a position is identified as variable) most likely to be found at a specific position in a 2-PG phosphatase. Many amino acids in SEQ ID NO: 7 are highly conserved and 2-PG phosphatases suitable for use in accordance with the methods of the present disclosure will comprise a substantial number, and sometimes all, of these highly conserved amino acids at positions aligning with the location of the indicated amino acid in SEQ ID NO: 7. In various embodiments, proteins suitable for use in accordance with the methods of the present disclosure have 2-PG phosphatase activity and comprise an amino acid sequence with at least 40%, at least 50%, at least 60%, or at least 70% sequence identity with SEQ ID NO: 7. For example, the *Ashbya aceri* yeast 4-nitrophenylphosphatase UniProt ID: R9XA12 sequence is 62% identical to consensus sequence #1 SEQ ID NO: 7, and is therefore encompassed by consensus sequence #1 SEQ ID NO: 7. The highly conserved amino acids in SEQ ID NO: 7 are D25, F27, F29, D30, C31, D32, G33, V34, W36, P43, E47, L52, K57, F61, V62, T63, N64, N65, K68, S69, R70, Y73, K76, F77, G81, F91, S93, A98, G118, G121, E125, L126, G130, G135, D161, V167, G170, L171, Y177, L187, F196, T199, N200, D202, T204, P206, G209, G214, A215, G216, G235, K236, P237, M241, I245, M261, G263, D264, R265, T268, D269, F272, G273, L278, T281, V284, L285, and G287.

In other embodiments, any protein that shares the specific function of 2-PG phosphatase as described herein can be used in a recombinant host cell of the disclosure despite comprising insufficient sequence identity (i.e., less than 40% identity) with the 2-PG phosphatase consensus sequence.

2.2.2 Methods to Identify and/or Improve Enzymes in the Glyceric Acid Pathway The present disclosure provides the construction and characterization of 3-PG phosphatases and 2-PG phosphatases in accordance with the present disclosure. The following methods have been developed for mutagenesis and diversification of genes for engineering specific or enhanced properties of targeted enzymes. The methods disclosed may be adapted as needed depending on the target enzyme properties desired. In some instances, the disclosed methods are suitable for use in engineering enzymes towards improved 3-PG phosphatase activity or 2-PG phosphatase activity of the glyceric acid pathway. In some embodiments, the 3-PG phosphatase is derived from an enzyme with native activity towards a substrate that is structurally similar to 3-PG. In many embodiments, the 3-PG phosphatase is derived from a phosphoric monoester hydrolase (EC #3.1.3.X), which comprises 3-PG phosphatase (EC #3.1.3.38), 2-PG phosphatase (EC #3.1.3.20), phosphoserine phosphatase (EC #3.1.3.3), glycerol-3-phosphate phosphatase (EC #3.1.3.21) and phosphoglycolate phosphatase (EC #3.1.3.18). Similarly, in embodiments that comprise a 2-PG phosphatase, the 2-PG phosphatase is derived from an enzyme with native activity towards a substrate that is structurally similar to 2-PG. In many embodiments, the 2-PG phosphatase is derived from a phosphoric monoester hydrolase (EC #3.1.3.X), which comprises 3-PG phosphatase (EC #3.1.3.38), 2-PG phosphatase (EC #3.1.3.20), phosphoserine phosphatase (EC #3.1.3.3), glycerol-3-phosphate phosphatase (EC #3.1.3.21) and phosphoglycolate phosphatase (EC #3.1.3.18).

Methods described herein for protein mutagenesis, identification, expression, purification, and characterization are methods widely-practiced by practitioners skilled in the art, who will appreciate that a wide variety of commercial solutions are available for such endeavors. Practitioners will understand that identification of mutated proteins comprise activity screens and phenotypic selections.

2.2.2.1 Generating Protein Libraries Via Mutagenesis

Enzymes that are identified as good mutagenesis starting points enter the protein engineering cycle, which comprises protein mutagenesis, protein identification, protein expression, protein characterization, recombinant host cell characterization, and any combination thereof. Iterative rounds of protein engineering are typically performed to produce an enzyme variant with properties that are different from the template/original protein. The enzyme variants of the present disclosure comprise 3-PG phosphatase and 2-PG phosphatase. Examples of enzyme characteristics that are improved and/or altered by protein engineering comprise, for example, substrate binding ($K_m$; i.e., a measure of enzyme binding affinity for a particular substrate) that includes non-natural substrate selectivity/specificity; enzymatic reaction rates ($k_{cat}$; the turnover rate of a particular enzyme-substrate complex into product and enzyme), to achieve desired pathway flux; temperature stability, for high temperature processing; pH stability, for processing in extreme pH ranges; substrate or product tolerance, to enable high product titers; removal of inhibition by products, substrates or intermediates; expression levels, to increase protein yields and overall pathway flux; oxygen stability, for operation of air sensitive enzymes under aerobic conditions; and anaerobic activity, for operation of an aerobic enzyme in the absence of oxygen. In some embodiments, the enzyme variant enables improved glyceric acid pathway flux. In some embodiments, the enzyme variant enables increased glycerate yield, titer and/or productivity. In some embodiments, the enzyme variant enables increased substrate specificity. In some embodiments, the enzyme variant displays improved kinetic properties, such as decreased $K_m$ and/or increased $k_{cat}$. In some embodiments, the enzyme variant has increased $K_m$ and/or decreased $k_{cat}$ for the substrate 3-PG or 2-PG. In some embodiments, the enzyme variant has $K_m \leq 3$ mM with 3-PG or 2-PG as substrate. In some embodiments, the enzyme variant has $k_{cat} \geq 10$ turnovers per second with 3-PG or 2-PG as substrate. In some embodiments, the enzyme variant is a product of one or more protein engineering cycles. In some embodiments, the enzyme variant comprises one or more point mutations.

In general, random and rational mutagenesis approaches are acceptable methods for generating DNA libraries of mutant proteins. Error-prone PCR is a random mutagenesis method widely used for generating diversity in protein engineering, is not only fast and easy, but it is also a method that has successfully produced mutated enzymes with altered activity from a wild type DNA template. (Wilson, D. S. & Keefe, A. D. Random mutagenesis by PCR. *Curr. Protoc. Mol. Biol.* Chapter 8, Unit 8.3 (2001.) To help increase the odds of identifying an enzyme with 3-PG/2-PG phosphatase activity, rational mutagenesis of a small number of active site mutations is also useful. For example, in embodiments wherein the starting protein for 3-PG phosphatase engineering is the *Escherichia coli* (*E. coli*) phosphoglycolate (EcGPH), atomic structures of EcGPH homologs are available to guide structural modeling of EcGPH with 3-PG bound in the active site. Structural modeling allows one to identify amino acids in the active site involved with substrate recognition. Other mutagenesis approaches that could be used comprise DNA shuffling and combinatorial mutagenesis. In some embodiments, the mutagenesis step is carried out more than once, resulting in iterative rounds of engineering.

Following library generation, mutated genes are typically cloned for expression in a host organism and in many cases the proteins are subsequently purified for in vitro phosphatase screening. In some embodiments, the host organism is *E. coli*. Mutated genes are cloned in a suitable expression plasmid comprising an auto-inducible promoter upstream of the gene and a His-tag sequence downstream of the gene. The proteins expressed from such a plasmid are isolated from whole cell lysate with Ni-NTA affinity purification methods, such as the Takara Capturem His-tagged Purification 96. Purified proteins then enter an in vitro phosphatase screen for characterization. The Ni-NTA affinity purification step helps to reduce background noise in the in vitro phosphatase screen by removing both native phosphatases as well as any free orthophosphate present in the lysate.

2.2.2.2 Generating Strain Libraries Via Directed Evolution

In another aspect of this disclosure, directed evolution methods are used to identify enzymes with phosphatase activity and/or improved the kinetic parameters (for example, decreasing the enzyme $K_m$ and/or increasing the enzyme $k_{cat}$ when using 3-PG as the substrate) of enzymes exhibiting suboptimal activity toward 3-PG or 2-PG. Directed evolution approaches are useful in generating strain libraries with a wide diversity of mutations wherein the mutations are driven by the process of natural selection given the constraints provided to the organism in its growth environment. Evolution approaches provide an effective and impartial way of introducing sequence mutations that give rise to functional change at an organism scale, enabling practitioners to explore non-intuitive mutations in the universe of possibilities that lie beyond the confines of one's understanding about structure-function specificity.

In some embodiments, a screen is designed to monitor the progress of evolution over time. In some of these embodiments, it is useful to link desired mutagenesis with a measurable phenotype so that the rate of evolution can be monitored over an extended period of time. In some of these embodiments, the measurable phenotype comprises cell growth, glucose consumption, and metabolite production. In some embodiments, the directed evolution experiment is designed so that mutations acquired in the target gene(s) is a measurable phenotype that is advantageous to the organism. In some of these embodiments, the advantageous measurable phenotype comprises cellular fitness, energy production, growth rate, tolerance to toxicity, and tolerance to extreme culture conditions (such as high or low pH, high or low temperature, high or low osmotic pressure, drought, and nutrient limitation). In various embodiments, one or more synthetic metabolic pathways are constructed by introducing exogenous nucleic acids to recombinant host cells. In these embodiments, the one or more synthetic metabolic pathways provide a method of applying selective pressure or a method of selecting strain variants that result from directed evolution.

Besides a well-crafted selection assay before the evolution experiment begins, starting nucleic acid templates for proteins of interest (i.e., target gene(s) or parent gene(s)) are also identified. In embodiments of the present disclosure, enzymes that serve as a good starting point for 3-PG phosphatase or 2-PG phosphatase engineering are identified. In these embodiments, 3-PG phosphatase/2-PG phosphatase-encoding nucleic acids are integrated into the genome of recombinant host cells. In some embodiments, the 3-PG phosphatase is derived from an enzyme with native activity towards a substrate that is structurally similar to 3-PG. In some embodiments, the 3-PG phosphatase is derived from a phosphoric monoester hydrolase (EC #3.1.3.X). Similarly, in embodiments comprising a 2-PG phosphatase, the 2-PG phosphatase is derived from an enzyme with native activity towards a substrate that is structurally similar to 2-PG. In some embodiments, the 2-PG phosphatase is derived from a phosphoric monoester hydrolase (EC #3.1.3.X).

Once a selection is established and target genes (i.e., for 3-PG phosphatases/2-PG phosphatases, according to embodiments of the present disclosure) are identified and integrated into the genome of recombinant host cells, recombinant host cells enter the directed evolution cycle, wherein the directed evolution cycle comprises: (1) mutagenesis in response to selective pressure; (2) analysis of recombinant host cells in the generated library for measurable phenotypic differences that arise due to selective pressure; and (3) isolation and characterization of evolved variants.

In some embodiments, acquisition of a mutation in the target gene enables the recombinant host cell to overcome the selective pressure. In some embodiments, recombinant host cells are passaged throughout the course of mutagenesis with selective pressure. In various embodiments, the selective pressure comprises nutrient limitation, cellular toxicity, and extreme culture conditions that further comprise high or low pH, high or low temperature, and high or low osmotic pressure. In some embodiments, the recombinant host cells are initially propagated without selective pressure prior to mutagenesis.

After exposure to selective pressure for some period of time, the evolved or evolving strains are screened for a change in phenotype in response to selective pressure. Non-limiting examples of phenotypic change comprise faster glucose consumption, faster cell growth, higher flux through a metabolic pathway or pathways, improved product yield/titer/productivity, decreased byproduct yield/titer, increased tolerance to toxicity, or increased tolerance to extreme culture conditions.

2.2.2.3 Enzyme Characterization

Following protein library generation, protein variants can be screened for phosphatase activity with any of a variety of published assays and commercial kits available for the measurement of free phosphate which can be used to screen 3-PG phosphatase/2-PG phosphatase activity. An example of a commercial in vitro assay is the Sigma-Aldrich assay kit catalog #MAK307 that produces a colorimetric output upon detection of free phosphate. With 3-PG as the substrate, for example, kinetic parameters $K_m$ (i.e., binding affinity for a substrate) and $k_{cat}$ (i.e., turnover rate of an enzyme-substrate complex into product and enzyme) are calculated from the assay. After identifying 3-PG phosphatases with this initial screen, the same assay kits can be used to test 3-PG phosphatase substrate specificity. In addition to 3-PG, a variety of glycolytic intermediates and other cellular metabolites can be provided as substrates in the assay to determine if the engineered 3-PG phosphatase can dephosphorylate other substrates, leading to byproducts that could be problematic in a commercial process. Non-limiting examples of intracellular metabolites that can serve as substrates comprise phosphoglycolate, glucose-6-phosphate, frustose-6-phosphate and glyceraldehyde-3-phosphate. 3-PG phosphatase $K_m$ and $k_{cat}$ are calculated for these substrates. In some embodiments, protein isolation is carried out prior to in vitro characterization, with commercially available kits such as the Takara Capturem His-tagged Purification 96.

Following strain library generation and screening, strain variants with desired evolved phenotype(s) are typically isolated and characterized. In some embodiments, mutations are acquired by the nucleic acids encoding target proteins. In these embodiments, nucleic acids encoding target proteins are sequenced so that acquired mutations are identified. In other embodiments, mutations are acquired by nucleic acids native to the recombinant host cells. In some embodiments, target proteins are analyzed for 3-PG phosphatase activity.

In some embodiments, iterative rounds of protein engineering are performed to produce enzyme variants with optimized properties, wherein the iterative rounds of protein engineering comprise rational mutagenesis, random mutagenesis, and directed evolution. In these embodiments, select variants from preceding rounds of protein engineering are identified for further protein engineering. Non-limiting examples of such properties comprise improved enzyme kinetics for specificity and/or turnover, improved pathway flux, increased metabolite yield, decreased byproduct yield. In some embodiments, culture medium or fermentation broth is analyzed for the presence of metabolites such as glyceric acid and/or byproducts, wherein the method of analysis is HPLC (high-performance liquid chromatography).

2.3 Glycolic Acid Pathway

Provided herein in certain embodiments are recombinant host cells having at least one active glycolic acid pathway from glycerate to glycolate. Recombinant host cells having an active glycolic acid pathway as used herein produce active enzymes useful to catalyze each metabolic reaction in a glycolic acid pathway, and therefore are capable of producing glycolic acid in measurable yields and/or titers when cultured under suitable conditions. Recombinant host cells having an active glycolic acid pathway comprise one or more heterologous nucleic acids encoding glycolic acid pathway enzymes and are capable of producing glycolate.

Recombinant host cells may employ combinations of metabolic reactions for biosynthetically producing the compounds of the present disclosure. The biosynthesized compounds produced by the recombinant host cells comprise glycolate, glycolic acid, and the intermediates, products and/or derivatives of the glycolic acid pathway. The biosynthesized compounds can be produced intracellularly and/or secreted into the fermentation medium. In certain embodiments, recombinant host cells of the present disclosure comprise a glycolic acid pathway that proceeds via glycerate.

2.3.1 Glycolic Acid Pathway Enzymes

The glycolic acid pathway described herein produces glycolate from glucose via the 3-PG phosphatase of the glyceric acid pathway with the following balanced, stoichiometric equation:

GLUCOSE+6NAD(P)⁺+4H₂O→2GLYCOLATE+ 6NAD(P)H+2CO₂

In a particular embodiment of the present disclosure, the glycolic acid pathway comprises three enzymes: hydroxypyruvate reductase (EC #1.1.1.81), hydroxypyruvate decarboxylase (EC #4.1.1.40), and glycoaldehyde reductase (EC #1.2.1.21). In some embodiments, all three glycolic acid pathway enzymes are required to convert glycerate to glycolate via the glycolic acid pathway of the present disclosure.

TABLE 2

Enzymes in the glycolic acid pathway

| EC # | Enzyme name | Reaction catalyzed |
|---|---|---|
| 1.1.1.81 | Hydroxypyruvate reductase | Glycerate + oxidized cofactor → Hydroxypyruvate + reduced cofactor |
| 4.1.1.40 | Hydroxypyruvate decarboxylase | Hydroxypyruvate + H₂O → Glycoaldehyde + CO₂ |
| 1.2.1.21 | Glycoaldehyde reductase | Glycoaldehyde + oxidized cofactor → Glycolate + reduced cofactor |

The glycolic acid pathway of the present disclosure is calculated to thermodynamically favor the conversion of glucose to glycolate. The advantaged thermodynamics of the pathway will help to achieve high glycolic acid yields, titers and/or productivities. The conversion of glucose to glycolate using the glyceric acid and glycolic acid pathways of the present disclosure as described herein has a calculated $\Delta_r G^m$ of −209.2+/−9.2 kJ/mol, indicative of a strong driving force that pushes the reaction to completion. Further, the pathway has net accumulation of 6 mol of NAD(P)H for every mol of glycolate produced from glucose, which can be used to help the cell generate ATP in aerobic fermentation, which is useful for product export, cellular maintenance, and other vital activities.

Specifically, two of the three reactions in the glycolic acid pathway are either thermodynamically irreversible (i.e., have a negative $\Delta_r G^m$ as described above), or are catalyzed by unidirectional enzymes (i.e., where the enzyme mechanism does not permit the reverse reaction); enzymes catalyzing these reactions are referred to as irreversible enzymes. The irreversible glycolic acid pathway enzymes are hydroxypyruvate decarboxylase (in the second step) and glycoaldehyde reductase (in the last step). As the pathway intermediates pass through these steps, they become locked into the portion of the glycolic acid pathway downstream of each irreversible enzyme. Generally speaking, when multiple enzymes in a metabolic pathway are irreversible this helps to increase product yields, titers, and productivities. Because the last two glycolic acid pathway steps are irreversible, a strong driving force pushes carbon out of the pathway to make the glycolate final product.

In certain embodiments, recombinant host cells comprise one or more heterologous nucleic acids encoding one, two, or all three enzymes of the glycolic acid pathway, or any combination thereof, wherein the heterologous nucleic acids are expressed in sufficient amounts to produce glycolate. In various embodiments, recombinant host cells may comprise multiple copies of a single heterologous nucleic acid and/or multiple copies of two or more heterologous nucleic acids. Recombinant host cells comprising multiple heterologous nucleic acids may comprise any number of heterologous nucleic acids.

The biosynthesized compounds produced by the recombinant host cells comprise glycolic acid, and the products and intermediates of the glycolic acid pathway, namely hydroxypyruvate, glycoaldehyde and glycolate. These products and intermediates can be produced intracellularly and/ or are secreted into the fermentation medium.

The present disclosure also provides consensus sequences useful in identifying and/or constructing glycolic acid pathway enzymes suitable for use in accordance with the methods of the present disclosure. For example, a hydroxypyruvate reductase encompassed by hydroxypyruvate reductase consensus sequence provided herein has an enzymatic activity that is identical, or essentially identical, or at least substantially similar with respect to ability to convert one molecule of glycerate and one molecule of NAD(P)⁺ to one molecule of hydroxypyruvate and one molecule of NAD(P) H.

2.3.1.1 Hydroxypyruvate Reductase

Hydroxypyruvate reductase (EC #1.1.1.81) described herein catalyzes the conversion of one molecule of glycerate and one molecule of NAD(P)⁺ to one molecule of hydroxypyruvate and one molecule of NAD(P)H. Any enzyme is suitable for use in accordance with this disclosure so long as the enzyme is capable of catalyzing said hydroxypyruvate reductase reaction.

In some embodiments, the hydroxypyruvate reductase is derived from a bacterial source. In some embodiments, the hydroxypyruvate reductase is derived from a cell belonging to a genus selected from the group comprising *Delftia*, *Hyphomicrobium*, *Methylobacterium*, *Paracoccus*, and *Pyrococcus*. Non-limiting examples of comprise *Pyrococcus furiosus* UniProt ID: Q8U3Y2, and *Pyrococcus yayanosii* UniProt ID: F8AEA4.

In some embodiments, the hydroxypyruvate reductase is derived from a eukaryotic source. In many embodiments, the hydroxypyruvate reductase is derived from a cell belonging to a genus selected from the group comprising *Arabidopsis*, *Bos*, *Brassica*, *Chlorella*, *Citrullus*, *Cucumis*, *Cucurbita*, *Homo*, *Hordeum*, *Mus*, *Nicotiana*, *Pisum*, *Rattus*, *Spinacia*, *Sus*, and *Zea*. Non-limiting examples comprise *Arabidopsis thaliana* UniProt ID: Q9C9W5, *Arabidopsis thaliana* UniProt ID: Q9LE33, *Arabidopsis thaliana* UniProt ID: Q9CA90, *Arabidopsis thaliana* UniProt ID: A0A1I9LPQ6, and *Homo sapiens* UniProt ID: Q9UBQ7.

In many embodiments, recombinant host cells comprise one or more heterologous nucleic acids encoding a hydroxypyruvate reductase wherein said recombinant host cells are capable of producing hydroxypyruvate. In various embodiments, proteins suitable for use in accordance with methods of the present disclosure have hydroxypyruvate reductase activity and comprise an amino acid sequence with at least 40%, at least 50%, at least 60%, at least 70%, at least 80%, at least 90%, or at least 95% sequence identity with UniProt ID: Q8U3Y2, UniProt ID: F8AEA4, UniProt ID: Q9C9W5, UniProt ID: Q9LE33, UniProt ID: Q9CA90, UniProt ID: A0A1I9LPQ6, and UniProt ID: Q9UBQ7. In many embodiments, the recombinant host cell is a *P. kudriavzevii* strain.

In other embodiments, any protein that shares the specific function of hydroxypyruvate reductase as described herein can be used in a recombinant host cell of the disclosure despite comprising insufficient sequence identity (i.e., less than 40% identity) with UniProt ID: Q8U3Y2, UniProt ID: F8AEA4, UniProt ID: Q9C$_9$W5, UniProt ID: Q9LE33, UniProt ID: Q9CA90, UniProt ID: A0A1I9LPQ6, or UniProt ID: Q9UBQ7.

2.3.1.2 Hydroxypyruvate Decarboxylase

Hydroxypyruvate decarboxylase (EC #4.1.1.40) described herein catalyzes the conversion of one molecule of hydroxypyruvate and one molecule of water to one molecule of glycoaldehyde and one molecule of carbon dioxide. Any enzyme is suitable for use in accordance with this disclosure so long as the enzyme is capable of catalyzing said hydroxypyruvate decarboxylase reaction.

In some embodiments, the hydroxypyruvate decarboxylase is derived from a eukaryotic source. In many embodiments, the hydroxypyruvate decarboxylase is derived from a cell belonging to a genus selected from the group comprising *Bos, Canis, Oryctolagus, Rattus* and *Sus*.

2.3.1.3 Glycoaldehyde Reductase

Glycoaldehyde reductase (EC #1.2.1.21) described herein catalyzes the conversion of one molecule of glycoaldehyde and one molecule of NAD(P)$^+$ to one molecule of glycolate and one molecule of NAD(P)H. Any enzyme is suitable for use in accordance with this disclosure so long as the enzyme is capable of catalyzing said glycoaldehyde reductase reaction.

In many embodiments, the glycoaldehyde reductase is derived from a bacterial source. In many embodiments, the glycoaldehyde reductase is derived from a cell belonging to a genus selected from the group comprising *Agrobacterium, Alcaligenes, Bacillus, Corynebacterium, Enterobacter, Escherichia, Flavobacterium, Klebsiella, Micrococcus, Pimelobacter, Protaminobacter, Proteus, Pseudomonas, Rhodococcus, Salmonella*, and *Staphylococcus*.

In some embodiments, the glycoaldehyde reductase is the *Escherichia coli* ALDA protein (abbr. EcALDA; UniProt ID: P25553; SEQ ID NO: 30). In many embodiments, recombinant host cells comprise one or more heterologous nucleic acids encoding a glycoaldehyde reductase wherein said recombinant host cells are capable of producing glycolate. In various embodiments, proteins suitable for use in accordance with methods of the present disclosure have glycoaldehyde reductase activity and comprise an amino acid sequence with at least 40%, at least 50%, at least 60%, at least 70%, at least 80%, at least 90%, or at least 95% sequence identity with SEQ ID NO: 30. In many embodiments, the recombinant host cell is a *P. kudriavzevii* strain.

In other embodiments, any protein that shares the specific function of glycoaldehyde reductase as described herein can be used in a recombinant host cell of the disclosure despite comprising insufficient sequence identity (i.e., less than 40% identity) with SEQ ID NO: 30.

2.4 Ancillary Proteins

In addition to the glyceric acid pathway enzymes and/or downstream product pathway enzymes, ancillary proteins are other proteins that are overexpressed in recombinant host cells of the present disclosure whose overexpression results in an increase in glyceric acid and/or downstream product yields, productivities, and/or titers as compared to control, or cells that do not overexpress said proteins. Ancillary proteins function outside the glyceric acid pathway and/or the downstream product pathway, wherein each ancillary protein may play a role that indirectly boosts the recombinant host cell's ability to produce glyceric acid and/or downstream product. Ancillary proteins comprise any protein (excluding glyceric acid pathway enzymes and downstream product pathway enzymes) of any structure or function that can increase glyceric acid and/or downstream product yields, titers, or productivities when overexpressed. Non-limiting examples of classes of proteins comprise transcription factors, transporters, scaffold proteins, proteins that decrease byproduct accumulation, and proteins that regenerate or synthesize redox cofactors.

Provided herein in certain embodiments are recombinant host cells comprising one or more heterologous nucleic acids encoding one or more ancillary proteins wherein said recombinant host cell is capable of producing higher glyceric acid and/or downstream product yields, titers, or productivities as compared to control cells, or host cells that do not comprise said heterologous nucleic acid(s). In some embodiments, that host recombinant cell naturally produces glyceric acid and/or downstream product, and in these cases, the glyceric acid and/or downstream product yields, titers, and/or productivities are increased. In other embodiments, the recombinant host cell comprises one or more heterologous nucleic acids encoding one or more glycolic acid pathway enzymes and/or downstream product pathway enzymes.

In certain embodiments of the present disclosure, the recombinant host cells comprise one or more heterologous nucleic acids encoding one or more glyceric acid pathway enzymes and/or one or more downstream product pathway enzymes, and one or more heterologous nucleic acids encoding one or more ancillary proteins. In certain of these embodiments, the recombinant host cells may be engineered to express more of these ancillary proteins. In these particular embodiments, the ancillary proteins are expressed at a higher level (i.e., produced at a higher amount as compared to cells that do not express said ancillary proteins) and may be operatively linked to one or more exogenous promoters or other regulatory elements.

In certain embodiments, recombinant host cells comprise both endogenous and heterologous nucleic acids encoding one or more glyceric acid pathway enzymes and/or one or more downstream product pathway enzymes, and one or more ancillary proteins. In certain embodiments, the recombinant host cells comprise one or more heterologous nucleic acids encoding one or more glyceric acid pathway enzymes and/or one or more ancillary proteins, and one or more endogenous nucleic acids encoding one or more glyceric acid pathway enzymes and/or one or more downstream product pathway enzymes, and/or one or more ancillary proteins.

In certain embodiments, endogenous nucleic acids of ancillary proteins are modified in situ (i.e., on chromosome in the recombinant host cell genome) to alter levels of expression, activity, or specificity. In some embodiments, heterologous nucleic acids are inserted into endogenous nucleic acids of ancillary proteins.

2.4.1 Ancillary Proteins for Redox Cofactor Recycling

One type of ancillary proteins is proteins that recycle the redox cofactors that are produced during glycolic acid pathway activity. Redox balance is fundamental to sustained metabolism and cellular growth in living organisms. Intracellular redox potential is determined by redox cofactors that facilitate the transfer of electrons from one molecule to another within a cell. Redox cofactors in yeast comprise the nicotinamide adenine dinucleotides, NAD and NADP, the flavin nucleotides, FAD and FMN, and iron sulfur clusters (Fe—S clusters).

Redox constraints play a role in end-product formation. Additional reducing power is provided to produce compounds whose degree of reduction is higher than that of the substrate. Conversely, producing compounds with a degree of reduction lower than that of the substrate will force the synthesis of byproducts with higher degrees of reduction to compensate for excess reducing power generated from substrate oxidation. Thus, redox neutrality is maintained to ensure high end-product yields. For example, the glycolic acid pathway results in a net formation of 3 mol of NAD(P)H for each mol of glycolic acid in the cytosol. Re-oxidation of NAD(P)H to NAD(P)$^+$ is involved in maintaining the thermodynamic driving force necessary for efficient and rapid glycolic acid production. This means that other processes in the cell can operate to restore the redox imbalance caused. In yeast, overflow metabolism can occur to reoxidize surplus cytosolic NAD(P)H, leading to byproduct accumulation, thereby decreasing product titers, yields and/or productivities. Non-limiting examples of ancillary proteins that can be overexpressed to restore this redox balance comprise NADH dehydrogenase and NADH oxidase. The enzymes of the glycolic acid pathway function in the cytosol, thus creating a redox imbalance with an excess of NAD(P)H in the cytosol. In certain embodiments, the ancillary proteins are expressed in the cytosol of recombinant host cells. In certain embodiments, the ancillary proteins are associated with the mitochondrial or cell membrane of the recombinant host cells.

In some embodiments, recombinant host cells comprise one or more heterologous and/or endogenous nucleic acids encoding a NADH dehydrogenase ancillary protein. The yeast NADH dehydrogenase catalyzes the oxidation of NAD(P)H to NAD(P)$^+$, providing cytosolic NAD(P)H to the mitochondrial respiratory chain. Any NAD(P)H dehydrogenase can be used in accordance with the present disclosure so long as it is capable of oxidizing NAD(P)H to NAD(P)$^+$ in the cytosol, restoring redox balance in the correct cellular space. In many embodiments, the NADH dehydrogenase ancillary protein is expressed in the cytosol. In some embodiments, the NADH dehydrogenase has an active site that is accessible to the cytosol. In some embodiments, the NADH dehydrogenase is a mitochondrial external NADH dehydrogenase. In yeast, the mitochondrial external NADH dehydrogenase is an inner-membrane mitochondrial protein with its catalytic site facing the intermembrane space. Because the mitochondrial outer membrane is permeable to most small molecules, the mitochondrial intermembrane space is considered to have the same environment as the cytosol. Therefore, the mitochondrial external NADH dehydrogenase contributes to the oxidation of cytosolic NAD(P)H and is a suitable ancillary protein for glycolic acid production. In some embodiments, the mitochondrial external NADH dehydrogenase is the *P. kudriavzevii* Nde1 protein (abbv. PkNDE1; SEQ ID NO: 20). In some embodiments, recombinant host cells comprise one or more heterologous nucleic acids encoding one or more proteins suitable for use in accordance with methods of the present disclosure having NAD(P)H dehydrogenase activity, and further comprise an amino acid sequence with at least 40%, at least 50%, at least 60%, at least 70%, at least 80%, at least 90%, or at least 95% sequence identity with SEQ ID NO: 20.

In some embodiments, recombinant host cells comprise one or more heterologous and/or endogenous nucleic acids encoding a NADH oxidase ancillary protein. The NADH oxidase converts NAD(P)H to NAD(P)$^+$ and can restore redox balance in the recombinant host cell cytosol while reducing molecular oxygen, resulting in the formation of one mol water per mol NADH. Any NAD(P)H oxidase can be used in accordance with the present disclosure so long as it is capable of oxidizing NAD(P)H to NAD(P)$^+$ and reducing molecular oxygen to water in the cytosol, restoring redox balance in the correct cellular space. In some embodiments, the NADH oxidase is the water-forming NADH oxidase. In some embodiments, the water-forming NADH oxidase is the *Lactococcus lactis* NoxE protein (abbv. L1NOXE; UniProt ID A2RIB7; SEQ ID: NO 21). In some embodiments, the NADH oxidase is derived from a bacterial source. In some embodiments, the NADH oxidase is derived from an archaeal source. In some embodiments, recombinant host cells comprise one or more heterologous nucleic acids encoding one or more proteins suitable for use in accordance with methods of the present disclosure have NAD(P)H oxidase activity and comprise an amino acid sequence with at least 40%, at least 50%, at least 60%, at least 70%, at least 80%, at least 90%, or at least 95% sequence identity with SEQ ID NO: 21.

2.4.2 Ancillary Proteins for Redox Cofactor Biogenesis

As explained in preceding paragraphs, redox balance is crucial for cell growth and sustained metabolism. Two out of the four glycolic acid pathway enzymes utilize redox cofactors that can be generated, in addition to being recycled, for robust metabolism and cell vitality. In some embodiments of the present disclosure, recombinant host cells comprise a hydroxypyruvate reductase that that utilizes NAD(P)$^+$. In some embodiments, recombinant host cells comprise a glycoaldehyde dehydrogenase that utilizes NAD(P)$^+$. Thus, biogenesis and homeostasis of these cofactors are crucial for efficient catalysis of these enzymatic reactions.

The NAD and NADP cofactors are involved in electron transfer and contribute to approximately 12% of all biochemical reactions in a cell (Osterman A., EcoSal Plus, 2009). NAD is assembled from L-aspartate, dihydroxyacetone phosphate (DHAP; glycerone), phosphoribosyl pyrophosphate (PRPP) and ATP. The NADP is assembled in the same manner and further phosphorylated. In some embodiments, recombinant host cells comprise heterologous and/or endogenous nucleic acids encoding one or more ancillary proteins that facilitate NAD and NADP cofactor assembly. In some embodiments, the ancillary proteins comprise one, more or all proteins suitable for use in accordance with methods of the present disclosure having NAD and/or NADP assembly capability, NAD and/or NADP transfer capability, NAD and/or NADP chaperone capability, or any combination thereof.

Similarly, Fe—S clusters facilitate various enzyme activities that require electron transfer. Because both iron and sulfur atoms are highly reactive and toxic to cells, Fe—S cluster assembly requires carefully coordinated synthetic pathways in living cells. The three known pathways are the Isc (iron sulfur cluster) system, the Suf (sulfur formation) system, and the Nif (nitrogen fixation) system. Each of these systems has a unique physiological role, yet several functional components are shared between them. First, a cysteine desulfurase enzyme liberates sulfur atoms from free cysteine. Then, a scaffold protein receives the liberated sulfur for Fe—S cluster assembly. Finally, the Fe—S cluster is transferred to a target apoprotein. In some embodiments of the present disclosure, recombinant host cells comprise heterologous and/or endogenous nucleic acids encoding one or more ancillary proteins that facilitate Fe—S cluster assembly. In some embodiments, the ancillary proteins comprise one, more or all proteins of the Isc system, the Suf system, the Nif system, or any combination thereof. In some embodiments, recombinant host cells comprise one or more heterologous nucleic acids encoding one or more proteins suitable for use in accordance with methods of the present disclosure having cysteine desulfurase activity, Fe—S cluster assembly capability, Fe—S cluster transfer capability, iron chaperone capability, or any combination thereof.

2.4.3 Ancillary Proteins for Glyceric Acid and/or Downstream Product Transport Another class of ancillary proteins useful for increasing glyceric acid and/or downstream product yields, titers, and/or productivities are organic acid transporter proteins. In some embodiments, recombinant host cells comprise one or more heterologous and/or endogenous nucleic acids encoding one or more organic acid transporter proteins. In many embodiments, the organic acid transporter is derived from a fungal source. In some embodiments, the organic acid transporter is selected from the group comprising *Saccharomyces cerevisiae* PDR12 (abbv. ScPDR12; UniProt ID: Q02785; SEQ ID NO: 22), *Saccharomyces cerevisiae* WAR1 (abbv. ScWAR1; UniProt ID: Q03631; SEQ ID NO: 23), *Schizosaccharomyces pombe* MAE1 (abbv. SpMAE1; UniProt ID: P50537; SEQ ID NO: 27), and *Kluyveromyces marxianus* PDC12 (abbv. KmPDR12; UniProt ID: W0T9C6; SEQ ID NO: 24). In some embodiments, recombinant host cells comprise one or more heterologous nucleic acids encoding one or more proteins suitable for use in accordance with methods of the present disclosure have glyceric acid and/or downstream product transporter activity. In some embodiments, recombinant host cells comprise one or more heterologous nucleic acids encoding one or more proteins that comprise an amino acid sequence with at least 40%, at least 50%, at least 60%, at least 70%, at least 80%, at least 90%, or at least 95% sequence identity with ScPDR12, ScWAR1, SpMAE1, and/or KmPDR12.

2.5 Decreasing or Eliminating Expression of Byproduct Pathway Enzymes

In an additional aspect of this disclosure, nucleic acids encoding byproduct pathway enzymes are disrupted in recombinant host cells of the present disclosure to increase glyceric acid and/or downstream product yields, productivities, and/or titers; and/or to decrease byproduct titers and/or yields as compared to control cells, or host cells that express native/undisrupted levels of said byproduct pathway enzymes. Byproduct pathway enzymes comprise any protein (excluding glyceric acid pathway enzymes and/or downstream product pathway enzymes) of any structure or function that can decrease glyceric acid and/or downstream product yields, titers, and/or productivities when disrupted because they utilize intermediates or products of the glyceric acid pathway and/or the downstream product pathway.

Byproducts that accumulate during glyceric acid and/or downstream product production can lead to: (1) lower glyceric acid and/or downstream product acid titers, productivities, and/or yields; and/or (2) accumulation of byproducts in the fermentation broth that increase the difficulty of downstream purification processes. In some embodiments, recombinant host cells may comprise genetic disruptions that encompass alternations, deletions, knockouts, substitutions, promoter modifications, premature stop codons, or knock-downs that decrease byproduct accumulation. In some embodiments, recombinant host cells comprising a disruption of one or more genes encoding a byproduct pathway enzyme will have altered performance characteristics as compared to cells without said genetic disruption(s), such as decreased or eliminated byproduct pathway enzyme expression, decreased or eliminated byproduct accumulation, improved glyceric acid and/or downstream product pathway activity, altered metabolite flux through the glyceric acid and/or downstream product pathway, higher glyceric acid and/or downstream product titers, glyceric acid and/or downstream product productivities, glyceric acid and/or downstream product yields, and/or altered cellular fitness.

One reason to decrease byproduct formation is to increase glyceric acid and/or downstream product pathway activity, resulting in an increased amount of glyceric acid and/or downstream product produced. In many embodiments, recombinant host cells of the present disclosure comprising one or more genetic disruptions of one or more genes encoding a byproduct pathway enzyme produce an increased glyceric acid and/or downstream product titer as compared to host cells that do not comprise said genetic disruption(s). In some of these embodiments, the glyceric acid titer in the fermentation broth is increased by 0.5 g/l, 1 g/l, 2.5 g/l, 5 g/l, 7.5 g/l, 10 g/l, or more than 10 g/l. In some of these embodiments, the downstream product titer in the fermentation broth is increased by 0.5 g/l, 1 g/l, 2.5 g/l, 5 g/l, 7.5 g/l, 10 g/l, or more than 10 g/l.

In addition to increasing glyceric acid and/or downstream product titers, decreasing byproduct formation can also help increase glyceric acid and/or downstream product yields. Because yield is independent of the volume of the fermentation broth, which can change during the course of a fermentation, it is often advantageous to measure glyceric acid and/or downstream product yields. In many embodiments, recombinant host cells of the present disclosure comprising one or more genetic disruptions of one or more genes encoding byproduct pathway enzymes produce an increased glyceric acid and/or downstream product yield as compared to host cells that do not comprise said genetic disruption. In some of these embodiments, the glyceric acid and/or downstream product yield is increased by 0.5%, 1%, 2.5%, 5%, 7.5%, 10%, or more than 10% (g-glyceric acid/g-substrate, or g-downstream product/g-substrate). The substrate in this yield calculation is the fermentation substrate, which is typically glucose, but may also be other, non-glucose substrates (for example, sucrose or glycerol).

Increasing glyceric acid and/or downstream product production can decrease manufacturing costs, and it can also be useful to disrupt genes encoding byproduct pathway enzymes in order to decrease byproduct formation. Byproducts are typically unwanted chemicals, are disposed of as waste, and their disposal can involve elaborate processing steps and containment requirements. Therefore, decreasing byproduct formation can lower production costs. In many embodiments, recombinant host cells of the present disclosure comprising one or more genetic disruptions of one or more genes encoding a byproduct pathway enzyme produces a lower byproduct titer as compared to host cells that do not comprise said genetic disruption. In some of these embodiments, a recombinant host cell of the disclosure comprising genetic disruption of one or more byproduct pathway enzymes produces a byproduct titer that is 0.5 g/l, 1 g/l, 2.5 g/l, 5 g/l, 7.5 g/l, 10 g/l, or greater than 10 g/l less than host cells that do not comprise said genetic disruption.

In many embodiments, recombinant host cells of the present disclosure comprising one or more genetic disruptions of one or more genes encoding a byproduct pathway enzyme produces a lower byproduct yield as compared to host cells that do not comprise said genetic disruption(s). In some of these embodiments, recombinant host cells comprise genetic disruption of one or more genes encoding byproduct pathway enzymes produce a byproduct yield that is 0.5%, 1%, 2.5%, 5%, 7.5%, 10%, or greater than 10% (percentage of g-byproduct for every g-substrate that is consumed) less than host cells that do not comprise said genetic disruption. As with the glycolic acid yield calculation, the substrate used in the byproduct yield calculation is the carbon source provided to the fermentation; this is typically glucose, sucrose, or glycerol, but may be any carbon substrate.

Non-limiting examples of byproducts that arise due to consumption of a glyceric acid pathway or a downstream product pathway substrate, intermediate or product comprise 2-phosphoglycerate, 3-phosphoglycerate, glycerol 3-phosphate, pyruvate, hydroxypyruvate, tartronate semialdehyde, 3-phosphonooxypyruvate, glyceraldehyde, 1-deoxy-D-xylulose 5-phosphate, DHAP, methylglyoxal, fructose 6-phosphoric acid, inositol-3-monophosphate, and 6-phospho-glucono-1,5-lactone, acetaldehyde, carbon dioxide, acetic acid, and ethanol. In the event of a redox imbalance, an undesirable excess of reduced or oxidized cofactors may also accumulate; thus, the redox cofactors NADH, $NAD^+$, NADPH and $NADP^+$ can also be considered byproducts.

A non-limiting list of enzyme-catalyzed reactions that utilize the glycolic acid pathway substrate (i.e., 3-PG or 2-PG), a glycolic acid pathway intermediate, or glycolic acid itself, are found in Table 3. Decreasing or eliminating expression of one, some or all of the genes encoding the enzymes in Table 3 can increase glyceric and/or glycolic acid production and/or decrease byproduct production. In many cases, the product of the enzyme-catalyzed reactions provided in Table 3 can accumulate in the fermentation broth; in such cases, this indicates that expression of the native gene encoding the listed enzyme should be reduced or eliminated. For example, the occurrence of dihydroxyacetone (abbv. DHAP; also known as glycerone) in the fermentation broth indicates that expression of a native gene encoding glycerol dehydrogenase should be decreased or eliminated. In some cases, the product of the specific reaction listed in Table 2 is further converted, either spontaneously or through the action of other enzymes, into a byproduct that accumulates in the fermentation broth. For example, dihydroxyacetone is generally metabolized to glycerol, which is found to accumulate in the fermentation broth. In cases where byproduct accumulation is due to the activity of multiple enzymes, one or more of the genes encoding the one or more byproduct pathway enzymes can be deleted or disrupted to reduce byproduct formation.

In some embodiments of the present disclosure, recombinant host cells comprise microbial strains with decreased or eliminated expression of one, some or all of the genes encoding enzymes listed in Table 3. In some embodiments, recombinant host cells comprise microbial strains with decreased byproduct accumulation wherein the byproducts are formed through the activity of one, some or all of the enzymes listed in Table 3. In some embodiments, recombinant host cells comprise microbial strains with decreased expression of pyruvate-utilizing enzymes. In some embodiments, recombinant host cells comprise microbial strains with decreased expression of glycolic acid-utilizing enzymes. In some embodiments, recombinant host cells comprise microbial strains with inability to catabolize or breakdown glyceric acid and/or glycolic acid. In some embodiments, recombinant host cells comprise genetic modifications that reduce the ability of the host cells to catabolize the glyceric acid and/or glycolic acid pathway intermediates except via the glyceric acid and/or glycolic acid pathway. In some embodiments, recombinant host cells comprise genetic modifications that decrease the ability of the host cells to catabolize pyruvate except via the glyceric acid and/or glycolic acid pathway.

TABLE 3

Enzyme-catalyzed reactions that consume glyceric acid pathway substrate, intermediate or product

| Substrate | EC # | Enzyme name | Reaction formula |
|---|---|---|---|
| 3-Phosphoglycerate | 5.4.2.12 | Phosphoglycerate mutase | 3-Phosphoglycerate → 2-Phosphoglycerate |
| 3-Phosphoglycerate | 1.1.1.95 | Phosphoglycerate dehydrogenase | 3-Phosphoglycerate + Oxidized cofactor → 3-Phosphonooxypyruvate + Reduced cofactor |
| 2-Phosphoglycerate | 4.2.1.11 | Enolase | 2-Phosphoglycerate → Phosphoenolpyruvate + $H_2O$ |
| Glycerate | 2.7.1.31 | Glycerate 3-kinase | Glycerate + ATP → 3-Phosphoglycerate + ADP |
| Glycerate | 2.7.1.165 | Glycerate 2-kinase | Glycerate + ATP → 2-Phosphoglycerate + ADP |
| Glycerate | 1.1.1.60 | Tartronate semialdehyde reductase | Glycerate + Oxidized cofactor → Tartronate semialdehyde + Reduced cofactor |
| Hydroxypyruvate | 2.6.1.45 | Serine-glyoxylate amino transferase | Glyoxylate + L-Serine → Glycine + Hydroxypyruvate |
| Hydroxypyruvate | 1.4.1.7 | Serine dehydrogenase | $NH_3$ + Hydroxypyruvate + Reduced cofactor → Serine + $H_2O$ + Oxidized cofactor |
| Hydroxyacetaldehyde | 1.1.1.2 | Alcohol dehydrogenase | Hydroxyacetaldehyde + Reduced cofactor → Ethylene glycol + Oxidized cofactor |

TABLE 3-continued

Enzyme-catalyzed reactions that consume glyceric acid pathway substrate, intermediate or product

| Substrate | EC # | Enzyme name | Reaction formula |
|---|---|---|---|
| Glucose 6-phosphate | 5.5.1.4 | Inositol 1-phosphate synthase | Glucose 6-phosphate → Inositol-3-monophosphate |
| Glucose 6-phosphate | 1.1.1.49 | Glucose-6-phosphate dehydrogenase | Glucose 6-phosphate + Oxidized cofactor → 6-Phosphoglucono-1,5-lactone + Reduced cofactor |
| Fructose-1,6-biphosphate | 3.1.3.11 | Fructose-1,6-biphosphate phosphatase | Fructose-1,6-bisphosphate + $H_2O$ → Fructose 6-phosphoric acid + Orthophosphate |
| DHAP | 1.1.1.8 | Glycerol-3-phosphate dehydrogenase | DHAP + NAD(P)H → NAD(P)$^+$ + Glycerol 3-phosphate |
| DHAP | 3.1.3.X | Dihydroxy acetone phosphate phosphatase | DHAP + $H_2O$ Dihydroxyacetone + Phosphate |
| DHAP | 4.2.3.3 | Methylglyoxal synthase | DHAP → Orthophosphate + Methylglyoxal |

2.5.1 Decreasing or Eliminating Expression of Phosphoglycerate Mutase

In some embodiments, it is beneficial to decrease or eliminate carbon flux through glycolysis (downstream of 3-PG) by decreasing or eliminating expression of phosphoglycerate mutase (EC #5.4.2.12). Phosphoglycerate mutase catalyzes the conversion of one molecule of 3-PG to one molecule of 2-phosphoglycerate (2-PG) diverting 3-PG from the glyceric acid and/or downstream product pathway to glycolysis. In some cases, it is beneficial to eliminate expression of genes encoding phosphoglycerate mutase activity, and in some of these cases, it is necessary to grow the biomass on an alternative carbon source to glucose (for example, ethanol, acetate, pyruvate, or citrate). In other cases, it is beneficial to decrease expression of phosphoglycerate mutase such that a small amount of glucose is converted to pyruvate during the production phase of the fermentation.

Several amino acids in phosphoglycerate mutase homologs are highly conserved. Any protein that is a phosphoglycerate mutase homolog will comprise a substantial number of highly conserved amino acids. In *P. kudriavzevii*, the phosphoglycerate mutase is PkGPM1 (UniProt ID: A0A099P7A2; SEQ ID NO: 14). Decreasing or eliminating expression of one or more homologs of PkGPM1 is useful for increasing glycolic acid production and/or decreasing carbon flux through glycolysis. As described above, homologous proteins share substantial sequence identity with each other. Any protein that is homologous to the phosphoglycerate mutase of the present disclosure (UniProt ID: A0A099P7A2; SEQ ID NO: 14) will share substantial sequence identity.

In some embodiments, recombinant host cells comprise genetic disruptions in one or more phosphoglycerate mutase homologs. As defined above, genetic disruptions encompass nucleic acid deletions, knockouts, nucleic acid insertions, nucleic acid substitutions, nucleic acid mutations, premature stop codons and promoter modifications. In some embodiments, recombinant host cells of the present disclosure comprise a genetic disruption of a homologous phosphoglycerate mutase gene with at least 40%, at least 50%, at least 60%, at least 70%, at least 80%, at least 90%, at least 95%, or more than 95% homology when compared to PkGPM1 (UniProt ID: A0A099P7A2; SEQ ID NO: 14). In some of these embodiments, the recombinant host cell is a *P. kudriavzevii* strain. In some embodiments, recombinant host cells comprise one or more gene disruptions that produce altered, decreased or eliminated activity in one, two or all three, phosphoglycerate mutase proteins. In some of these other embodiments, the recombinant host cell is a *P. kudriavzevii* strain.

The phosphoglycerate mutase consensus sequence #3 (SEQ ID NO: 25) provides the sequence of amino acids in which each position identifies the amino acid (if a specified amino acid is identified) or a subset of amino acids (if a position is identified as variable) most likely to be found at a specific position in a phosphoglycerate mutase. Many amino acids in SEQ ID NO: 25 are highly conserved and phosphoglycerate mutases encoded by nucleic acids suitable for deletion or disruption in accordance with the methods of the present disclosure will comprise a substantial number, and sometimes all, of these highly conserved amino acids at positions aligning with the location of the indicated amino acids in SEQ ID NO: 25. In various embodiments, proteins encoded by nucleic acids suitable for disruption in accordance with the methods of the present disclosure have phosphoglycerate mutase activity and comprise an amino acid sequence with at least 40%, at least 50%, at least 60%, or at least 70% sequence identity with SEQ ID NO: 25. For example, the *Scheffersomyces stipites* phosphoglycerate mutase UniProt ID: A3LN94 is 81% identical to consensus sequence #3 (SEQ ID NO: 25), and is therefore encompassed by consensus sequence #3 (SEQ ID NO: 25).

In some embodiments, recombinant host cells comprise heterologous nucleic acids encoding glyceric acid and/or glycolic acid pathway enzymes, and further comprise one or more genetic disruptions in one, more, or all phosphoglycerate mutase homologs. Example 2 describes recombinant *P. kudriavzevii* host cells comprising genetic disruption of the native phosphoglycerate mutase resulting in glyceric acid production whereas the wild type host cell produced no glyceric acid. Furthermore, Example 5 describes recombinant *P. kudriavzevii* host cells comprising heterologous nucleic acids encoding glyceric acid pathway enzymes and also comprising genetic disruption of the native phosphoglycerate mutase. Recombinant host cells comprising both genetic modifications (i.e., expressing the glyceric acid pathway enzyme and disruption of the phosphoglycerate mutase) produced more glyceric acid than recombinant host cells comprising only genetic disruption of the phosphoglycerate mutase.

In said recombinant host cells, carbon flux through glycolysis to pyruvate and native byproducts, including ethanol and/or acetate, is reduced. In certain embodiments, pyruvate, ethanol, and/or acetate byproduct titers (i.e., g of byproduct/liter of fermentation volume) at the end of fermentation are 10 g/l or less, preferably 5 g/l or less, and most preferably 2.5 g/l or less. In certain embodiments, pyruvate, ethanol, and/or acetate byproduct yield (i.e., percentage of g of byproduct/g of substrate) at the end of fermentation is 10% or less, 5% or less, 2.5% or less, and preferably, 1% or less.

2.5.2 Decreasing or Eliminating Expression of Phosphoglycerate Dehydrogenase Another enzyme that depletes the cellular pool of 3-PG is phosphoglycerate dehydrogenase (EC #1.1.1.95); it catalyzes the conversion of one molecule of 3-PG and one molecule of NAD(P)$^+$ to one molecule of 3-phosphonooxypyruvate and one molecule of NAD(P)H. In some cases, it is beneficial to decrease or eliminate expression of genes encoding phosphoglycerate dehydrogenase to prevent 3-PG depletion.

Several amino acids in phosphoglycerate dehydrogenase homologs are highly conserved. Any protein that is a phosphoglycerate dehydrogenase homolog will comprise a substantial number of highly conserved amino acids. For example, in S. cerevisiae, there are at least two phosphoglycerate dehydrogenase homologs: ScSER3 protein (UniProt ID: P40054; SEQ ID NO: 15) and ScSER33 (UniProt ID: P40510). ScSER33 shares substantial sequence identity with ScSER3 and is thus a protein homolog of ScSER3. In some embodiments, recombinant host cells of the present disclosure comprise one or more genetic disruptions to one or more phosphoglycerate dehydrogenase homologs with at least 40%, at least 50%, at least 60%, at least 70%, at least 80%, at least 90%, at least 95%, or more than 95% homology when compared to ScSER3 (SEQ ID NO: 15).

The phosphoglycerate dehydrogenase consensus sequence #2 (SEQ ID NO: 17) provides the sequence of amino acids in which each position identifies the amino acid (if a specified amino acid is identified) or a subset of amino acids (if a position is identified as variable) most likely to be found at a specific position in a phosphoglycerate dehydrogenase. Many amino acids in SEQ ID NO: 17 are highly conserved and phosphoglycerate dehydrogenases suitable for use in accordance with the methods of the present disclosure will comprise a substantial number, and sometimes all, of these highly conserved amino acids at positions aligning with the location of the indicated amino acids in SEQ ID NO: 17. In various embodiments, proteins suitable for use in accordance with the methods of the present disclosure have phosphoglycerate dehydrogenase activity and comprise an amino acid sequence with at least 40%, at least 50%, at least 60%, or at least 70% sequence identity with SEQ ID NO: 17. For example, the Aspergillus clavatus D-3-phosphoglycerate dehydrogenase UniProt ID: A1C9P2 is 63% identical to consensus sequence #2 (SEQ ID NO: 17), and is therefore encompassed by consensus sequence #2 (SEQ ID NO: 17).

In some embodiments, recombinant host cells comprise heterologous nucleic acids encoding glyceric acid and/or glycolic acid pathway enzymes, and further comprise one or more genetic disruptions in one, more, or all phosphoglycerate dehydrogenase homologs.

3-phosphonoxypyruvate is an intermediate in the biosynthesis of serine and in certain embodiments, serine byproduct titer (i.e., g of byproduct/liter of fermentation volume) at the end of fermentation is 10 g/l or less, preferably 5 g/l or less, and most preferably 2.5 g/l or less. In certain embodiments, serine byproduct yield (i.e., percentage of g of byproduct/g of substrate) at the end of fermentation is 10% or less, 5% or less, 2.5% or less, and preferably, 1% or less.

2.5.3 Decreasing or Eliminating Expression of Enolase

In some embodiments, it is beneficial to decrease or eliminate carbon flux through glycolysis (downstream of 2-PG) by decreasing or eliminating expression of enolase (EC #4.2.1.11). Enolase catalyzes the conversion of one molecule of 2-PG to one molecule of phosphoenolpyruvate and on molecule of water, diverting 2-PG from the glyceric acid and/or downstream product enolase activity, and in some of these cases, it will be necessary to grow the biomass on an alternative carbon source to glucose (for example, ethanol, acetate, pyruvate, or citrate). In other cases, it is beneficial to decrease expression of enolase such that a small amount of glucose is converted to pyruvate during the production phase of the fermentation.

Several amino acids in enolase homologs are highly conserved. Any protein that is an enolase homolog will comprise a substantial number of highly conserved amino acids. For example, in S. cerevisiae, there are least two enolase homologs: ScENO1 protein (UniProt ID: P00924; SEQ ID NO: 28) and ScENO2 (UniProt ID: P00925, SEQ ID NO: 29). ScENO1 shares substantial sequence identity with ScENO2 and is thus a protein homolog of ScENO1. In some embodiments, recombinant host cells of the present disclosure comprise one or more genetic disruptions to one or more enolase homologs with at least 40%, at least 50%, at least 60%, at least 70%, at least 80%, at least 90%, at least 95%, or more than 95% homology when compared to ScENO1 (SEQ ID NO: 28) or ScENO2 (SEQ ID NO: 29).

The enolase consensus sequence #4 (SEQ ID NO: 26) provides the sequence of amino acids in which each position identifies the amino acid (if a specified amino acid is identified) or a subset of amino acids (if a position is identified as variable) most likely to be found at a specific position in an enolase. Many amino acids in SEQ ID NO: 26 are highly conserved and enolase suitable for use in accordance with the methods of the present disclosure will comprise a substantial number, and sometimes all, of these highly conserved amino acids at positions aligning with the location of the indicated amino acids in SEQ ID NO: 26. In various embodiments, proteins suitable for use in accordance with the methods of the present disclosure have enolase activity and comprise an amino acid sequence with at least 40%, at least 50%, at least 60%, or at least 70% sequence identity with SEQ ID NO: 26. For example, the Ajellomyces capsulatus enolase UniProt ID: C0NAB0 is 83% identical to consensus sequence #4 (SEQ ID NO: 26), and is therefore encompassed by consensus sequence #4 (SEQ ID NO: 26).

In some embodiments, recombinant host cells comprise heterologous nucleic acids encoding glyceric acid and/or glycolic acid pathway enzymes, and further comprise one or more genetic disruptions in one, more, or all enolase homologs.

In said recombinant host cells, carbon flux through glycolysis to pyruvate and native byproducts, including ethanol and/or acetate, is reduced. In certain embodiments, pyruvate, acetate, and/or ethanol byproduct titer (i.e., g of byproduct/liter of fermentation volume) at the end of fermentation is 10 g/l or less, preferably 5 g/l or less, and most preferably 2.5 g/l or less. In certain embodiments, pyruvate, ethanol, and/or ethanol byproduct yield (i.e., percentage of g of byproduct/g of substrate) at the end of fermentation is 10% or less, 5% or less, 2.5% or less, and preferably, 1% or less.

2.5.4 Decreasing or Eliminating Expression of Glycerate 3-Kinase

In some embodiments, it is beneficial to decrease or eliminate expression of glycerate 3-kinase (EC #2.7.1.31) to prevent glycerate from being converted back to 3-PG, reversing the 3-PG phosphatase reaction, thus leaving downstream product pathway(s). In some cases, it is advantageous to decrease or eliminate expression of genes encoding enzymes with glycerate kinase.

Several amino acids in glycerate 3-kinase homologs are highly conserved. Any protein that is a glycerate 3-kinase homolog will comprise a substantial number of highly conserved amino acids. In *Escherichia coli*, there is at least one glycerate 3-kinase: the GlxK protein (abbv. EcGLXK; UniProt ID: P77364; SEQ ID NO: 16.) In some embodiments, recombinant host cells of the present disclosure comprise one or more genetic disruptions to one or more glycerate 3-kinase homologs with at least 40%, at least 50%, at least 60%, at least 70%, at least 80%, at least 90%, at least 95%, or more than 95% homology when compared to EcGLXK2.

In some embodiments, recombinant host cells comprise heterologous nucleic acids encoding glyceric acid and/or glycolic acid pathway enzymes, and further comprise one or more genetic disruptions in one, more, or all glycerate 3-kinase homologs.

In said recombinant host cells, carbon flux through glycolysis to pyruvate and native byproducts, including ethanol and/or acetate, is reduced. In certain embodiments, pyruvate, ethanol, and/or acetate byproduct titers (i.e., g of byproduct/liter of fermentation volume) at the end of fermentation are 10 g/l or less, preferably 5 g/l or less, and most preferably 2.5 g/l or less. In certain embodiments, pyruvate, ethanol, and/or acetate byproduct yield (i.e., percentage of g of byproduct/g of substrate) at the end of fermentation is 10% or less, 5% or less, 2.5% or less, and preferably, 1% or less. In certain embodiments, 3-PG byproduct titer (i.e., g of byproduct/liter of fermentation volume) at the end of fermentation is 10 g/l or less, preferably 5 g/l or less, and most preferably 2.5 g/l or less. In certain embodiments, 3-PG byproduct yield (i.e., percentage of g of byproduct/g of substrate) at the end of fermentation is 10% or less, 5% or less, 2.5% or less, and preferably, 1% or less.

2.5.5 Decreasing or Eliminating Expression of Glycerate 2-Kinase

Another enzyme that depletes the cellular pool of glycerate is glycerate 2-kinase. In some embodiments, it is beneficial to decrease or eliminate expression of glycerate 2-kinase (EC #2.7.1.165) to prevent glycerate from being converted to 2-phosphoglycerate (2-PG), thus leaving the glycolic acid pathway. In some cases, it is beneficial to decrease or eliminate expression of genes encoding enzymes with glycerate 2-kinase activity prevent glycerate depletion.

Several amino acids in glycerate 2-kinase homologs are highly conserved. Any protein that is a glycerate 2-kinase homolog will comprise a substantial number of highly conserved amino acids. For example, in *Escherichia coli*, there is at least one glycerate 2-kinase homologs: the GarK protein (abbv. EcGARK; UniProt ID: P23524; SEQ ID NO: 18). In some embodiments, recombinant host cells of the present disclosure comprise one or more genetic disruptions to one or more glycerate 2-kinase homologs with at least 40%, at least 50%, at least 60%, at least 70%, at least 80%, at least 90%, at least 95%, or more than 95% homology when compared to EcGARK.

In some embodiments, recombinant host cells comprise heterologous nucleic acids encoding glyceric acid and/or glycolic acid pathway enzymes, and further comprise one or more genetic disruptions in one, more, or all glycerate 2-kinase homologs.

In said recombinant host cells, carbon flux through glycolysis to pyruvate and native byproducts, including ethanol and/or acetate, is reduced. In certain embodiments, pyruvate, ethanol, and/or acetate byproduct titers (i.e., g of byproduct/liter of fermentation volume) at the end of fermentation are 10 g/l or less, preferably 5 g/l or less, and most preferably 2.5 g/l or less. In certain embodiments, pyruvate, ethanol, and/or acetate byproduct yield (i.e., percentage of g of byproduct/g of substrate) at the end of fermentation is 10% or less, 5% or less, 2.5% or less, and preferably, 1% or less. In certain embodiments, 2-PG byproduct titer (i.e., g of byproduct/liter of fermentation volume) at the end of fermentation is 10 g/l or less, preferably 5 g/l or less, and most preferably 2.5 g/l or less. In certain embodiments, 2-PG byproduct yield (i.e., percentage of g of byproduct/g of substrate) at the end of fermentation is 10% or less, 5% or less, 2.5% or less, and preferably, 1% or less.

2.5.6 Decreasing or Eliminating Expression of Glycerol-3-Phosphate Dehydrogenase In addition to the possible byproducts derived from 3-PG and glycolic acid pathway intermediates and product, additional byproducts can arise from intermediates in glycolysis (Table 2). Glycerol is a common byproduct that occurs under conditions of excess NADH. NAD-dependent glycerol-3-phosphate dehydrogenase (EC #1.1.1.8) catalyzes the conversion of one molecule of dihydroxyacetone phosphate (DHAP; glycerone phosphate) and one molecule of NAD (P)H to one molecule of glycerol 3-phosphate and one molecule of NAD(P)$^+$, leading to the formation of the undesired byproduct glycerol. In *P. kudriavzevii*, NAD-dependent glycerol-3-phosphate dehydrogenase activity is the Gpd1 protein (abbv. PkGPD1; SEQ ID NO: 19).

Although this glycerol-3-phosphate dehydrogenase-catalyzed reaction is reversible, glycerol 3-phosphate production is favored during glyceric and glycolic acid production due to NADH accumulation in the cytosol. Decreasing or eliminating the expression of PkGPD1 or its homologs is useful for decreasing glycerol byproduct accumulation. In some embodiments of the present disclosure, recombinant host cells comprise one or more genetic disruptions in one or more nucleic acids encoding a glycerol-3-phosphate dehydrogenase that gives rise to decreased, altered or eliminated expression and/or protein activity. In embodiments where the recombinant host cell is a *P. kudriavzevii* strain, the glycerol-3-phosphate dehydrogenase is PkGPD1.

Several amino acids in glycerol-3-phosphate dehydrogenase are highly conserved. Any protein that is homologous to PkGPD1 will comprise amino acids corresponding to a substantial number of highly conserved amino acids in PkGPD1. In some embodiments, recombinant host cells of the present disclosure comprise one or more genetic disruptions in one or more PkGPD1 homologs with at least 40%, at least 50%, at least 60%, at least 70%, at least 80%, at least 90%, at least 95%, or more than 95% homology when compared to PkGPD1.

In some embodiments, recombinant host cells comprise heterologous nucleic acids encoding glyceric acid pathway enzymes, and further comprise one or more genetic disruptions in one, more, or all PkGPD1 homologs. Glycerol-3-phosphate is an intermediate in the byproduct pathway resulting in glycerol. In certain embodiments, glycerol 3-phosphate byproduct titer at the end of fermentation is 10 g/l or less, preferably at a titer of 5 g/l or less, and most preferably at a titer of 2.5 g/l or less. In certain embodiments, glycerol 3-phosphate byproduct yield at the end of fermentation is 10% or less, 5% or less, 2.5% or less, and preferably, 1% or less. In certain embodiments, glycerol byproduct titer at the end of fermentation is 10 g/l or less, preferably at a titer of 5 g/l or less, and most preferably at a titer of 2.5 g/l or less. In certain embodiments, glycerol byproduct yield at the end of fermentation is 10% or less, 5% or less, 2.5% or less, and preferably, 1% or less.

2.6 Genetic Engineering

Expression of glyceric acid pathway enzymes is achieved by transforming host cells with exogenous nucleic acids encoding glyceric acid pathway enzyme(s), producing recombinant host cells of the present disclosure. The same is true for expression of downstream product pathway enzymes and ancillary proteins. Any method can be used to introduce exogenous nucleic acids into a host cell to produce a recombinant host cell of the present disclosure. Many such methods are known to practitioners in the art. Some examples comprise electroporation, chemical transformation, and conjugation. Some examples comprise electroporation, chemical transformation, and conjugation. After exogenous nucleic acids enter the host cell, nucleic acids may integrate in to the cell genome via homologous recombination.

Recombinant host cells of the present disclosure may comprise one or more exogenous nucleic acid molecules/elements, as well as single or multiple copies of a particular exogenous nucleic acid molecule/element as described herein. These molecules/elements comprise transcriptional promoters, transcriptional terminators, protein coding regions, open reading frames, regulatory sites, flanking sequences for homologous recombination, and intergenic sequences.

Exogenous nucleic acids can be maintained by recombinant host cells in various ways. In some embodiments, exogenous nucleic acids are integrated into the host cell genome. In other embodiments, exogenous nucleic acids are maintained in an episomal state that can be propagated, either stably or transiently, to daughter cells. Exogenous nucleic acids may comprise selectable markers to ensure propagation. In some embodiments, the exogenous nucleic acids are maintained in recombinant host cells with selectable markers. In some embodiments, the selectable markers are removed and exogenous nucleic acids are maintained in a recombinant host cell strain without selection. In some embodiments, removal of selectable markers is advantageous for downstream processing and purification of the fermentation product.

In some embodiments, endogenous nucleic acids (i.e., genomic or chromosomal elements of a host cell), are genetically disrupted to alter, mutate, modify, modulate, disrupt, enhance, remove, or inactivate a gene product. In some embodiments, genetic disruptions alter expression or activity of proteins native to a host cell. In some embodiments, genetic disruptions circumvent unwanted byproduct formation or byproduct accumulation. Genetic disruptions occur according to the principle of homologous recombination via methods well known in the art. Disrupted endogenous nucleic acids can comprise open reading frames as well as genetic material that is not translated into protein. In some embodiments, one or more marker genes replace deleted genes by homologous recombination. In some of these embodiments, the one or more marker genes are later removed from the chromosome using techniques known to practitioners in the art.

Section 3: Methods of Producing Glyceric Acid, Glycerate Salts, and/or Downstream Products with Recombinant Host Cells Methods are provided herein for producing glyceric acid, glycerate salts, and/or downstream products from recombinant host cells of the present disclosure. In certain embodiments, the methods comprise the steps of: (1) culturing recombinant host cells as provided by the present disclosure in a fermentation broth containing at least one carbon source and one nitrogen source under conditions such that glycerate is produced; and (2) recovering the glycerate, glyceric acid or glycerate salt from the fermentation broth. In some embodiments, the glyceric acid is first converted to a glycerate salt before the glycerate salt is recovered from the fermentation broth. In some embodiments, the glyceric acid or glycerate salt is first converted to a downstream product before the downstream product is recovered from the fermentation broth. In some embodiments, the glyceric acid or glycerate salt is converted to a downstream product by recombinant host cells of the present disclosure. In some embodiments, the downstream products comprise glycolic acid and glycolate salt.

3.1 Fermentative Production of Glyceric Acid, Glycerate Salts, and/or Downstream Products by Recombinant Host Cells Any of the recombinant host cells of the present disclosure can be cultured to produce and/or secret glycerate (i.e., glycerate salt and glyceric acid). In some embodiments, the recombinant host cells of the present disclosure can be cultured to also produce one or more downstream products, such as glycolate salt and glycolic acid. As disclosed herein, the glycerate or downstream product can then be esterified and distilled to generate a purified ester.

Materials and methods for the maintenance and growth of microbes, as well as fermentation conditions, are well known to practitioners of ordinary skill in the art. It is understood that consideration can be given to appropriate culture medium, pH, temperature, revival of frozen stocks, growth of seed cultures and seed trains, and requirements for aerobic, microaerobic, or anaerobic conditions, depending on the specific requirements of the host cells, the fermentation, and process flows.

The methods of producing glycerate and/or one or more downstream products provided herein may be performed in a suitable fermentation broth in a suitable bioreactor such as a fermentation vessel, including but not limited to a culture plate, a flask, or a fermenter. Further, the methods can be performed at any scale of fermentation known in the art to support microbial production of small-molecules on an industrial scale. Any suitable fermenter may be used including a stirred tank fermenter, an airlift fermenter, a bubble column fermenter, a fixed bed bioreactor, or any combination thereof.

In some embodiments of the present disclosure, the fermentation broth is any fermentation broth in which a recombinant host cell capable of producing glycerate and/or a downstream product according to the present disclosure, and can subsist (i.e., maintain growth, viability, and/or catabolize glucose or other carbon source). In some embodiments, the fermentation broth is an aqueous medium comprising assimilable carbon, nitrogen, and phosphate sources. Such a medium can also comprise appropriate salts, minerals, metals, and other nutrients. In some embodiments, the carbon source and cell nutrients are provided to the fermentation broth incrementally or continuously, and maintained at essentially the minimum level required for efficient assimilation by growing cells. Examples of cell growth procedures comprise batch fermentation, fed-batch fermentation with batch separation, fed-batch fermentation with continuous separation, and continuous fermentation with continuous separation. These procedures are well known to practitioners of ordinary skill in the art.

In some embodiments of the present disclosure, the handling and culturing of recombinant host cells to produce glycerate and/or downstream product may be divided up into phases, such as growth phase, production phase, and/or recovery phase. The following paragraphs provide examples of features or purposes that may relate to these different phases. These features or purposes may vary based on the recombinant host cells used, the desired glycerate and/or downstream product yield, titer, and/or productivity, or other factors. While it may be beneficial in some embodiments for the glyceric acid pathway enzymes and/or downstream product pathway enzymes, ancillary proteins and/or endogenous host cell proteins to be constitutively expressed, in other embodiments, it may be preferable to selectively express or repress any or all of the aforementioned proteins.

During growth phase, recombinant host cells may be cultured to focus on growing cell biomass by utilizing the carbon source provided. In some embodiments, expression of glyceric acid pathway enzymes, and/or downstream product pathway enzymes, and/or ancillary proteins are repressed or uninduced. In some embodiments, no appreciable amount of glycerate, downstream product, or any of their pathway intermediates are made. In some embodiments, proteins that contribute to cell growth and/or cellular processes may be selectively expressed.

During production phase, however, recombinant host cells may be cultured to stop producing cell biomass and to focus on glycerate and/or downstream product biosynthesis by utilizing the carbon source provided. In some embodiments, glyceric acid pathway enzymes, downstream product pathway enzymes, and/or ancillary proteins, may be selectively expressed during production to generate high product titers, yields and productivities. The production phase is synonymous with fermentation, fermentation run or fermentation phase.

In some embodiments, the growth and production phases take place at the same time. In other embodiments, the growth and production phases are separate. While in some embodiments, product is made exclusively during production phase, in other embodiments some product is made during growth phase before production phase begins.

The recovery phase marks the end of the production phase, during which cellular biomass is separated from fermentation broth and glycerate or downstream product is purified from fermentation broth. In some fermentation methods, for example, fill-draw and continuous fermentations, there may be multiple recovery phases where fermentation broth containing biomass and glycolic acid are removed from the fermentation system. The draws of fermentation broth may be processed independently or may be stored, pooled, and processed together. In other fermentation methods, for example, batch and fed-batch fermentations, there may only be a single recovery phase.

Fermentation procedures are particularly useful for the biosynthetic production of commercial glycerate and/or downstream product. Fermentation procedures can be scaled up for manufacturing glycerate and/or downstream product and examples of fermentation procedures comprise, for example, fed-batch fermentation and batch product separation; fed-batch fermentation and continuous product separation; batch fermentation and batch product separation; and continuous fermentation and continuous product separation.

3.1.1 Carbon Source

The carbon source provided to the fermentation can be any carbon source that can be fermented by recombinant host cells. Suitable carbon sources comprise, but are not limited to, monosaccharides, disaccharides, polysaccharides, glycerol, acetate, ethanol, methanol, methane, or one or more combinations thereof. Examples of monosaccharides suitable for use in accordance to the methods of the present disclosure comprise, but are not limited to, dextrose (glucose), fructose, galactose, xylose, arabinose, and any combination thereof. Examples of disaccharides suitable for use in accordance to the methods of the present disclosure comprise, but are not limited to, sucrose, lactose, maltose, trehalose, cellobiose, and any combination thereof. Examples of polysaccharides suitable for use in accordance to the methods of the present disclosure comprise, but are not limited to, starch, glycogen, cellulose, and combinations thereof. In some embodiments, the carbon source is dextrose. In other embodiments, the carbon source is sucrose. In some embodiments, mixtures of some or all the aforementioned carbon sources can be used in fermentation.

3.1.2 pH

The pH of the fermentation broth can be controlled by the addition of acid or base to the culture medium. Preferably, fermentation pH is controlled at the beginning of fermentation and then allowed to drop as glycolic acid accumulates in the broth, minimizing the amount of base added to the fermentation (thereby improving process economics) as well as minimizing the amount of salt formed. Specifically, the pH during fermentation is maintained in the range of 2-8, and more preferably, in the range of 4-8. At the end of fermentation, the final pH is in the range of 2-5. Non-limiting examples of suitable acids used to control fermentation pH comprise acetic acid, hydrochloric acid, and sulfuric acid. Non-limiting examples of suitable bases used to control fermentation pH comprise sodium bicarbonate ($NaHCO_3$), sodium hydroxide (NaOH), potassium bicarbonate ($KHCO_3$), potassium hydroxide (KOH), calcium hydroxide ($Ca(OH)_2$), calcium carbonate ($CaCO_3$), ammonia, ammonium hydroxide, and diammonium phosphate. In some embodiments, a concentrated acid or concentrated base is used to limit dilution of the fermentation broth.

Base cations and glycerate anions react to form ionic compounds in fermentation broths. Base cations and downstream product anions also react to form ionic compounds in fermentation broths. For example, base $Na^+$ cations and glycerate anions react to form sodium glycerate; similarly, base Na+ cations and glycolate anions react to form sodium glycolate. In some embodiments, the ionic compounds formed by base cations and glycerate or glycolate anions are soluble in fermentation broth. In other embodiments, the ionic compounds formed by base cations and glycerate or glycolate anions are insoluble salts and may crystallize in the fermentation broth.

3.1.3 Temperature

The temperature of the fermentation broth can be any temperature suitable for growth of the recombinant host cells and/or production of glycerate and/or downstream product. Preferably, during glycerate and/or downstream product production, the fermentation broth is maintained within a temperature range of from about 20° C. to about 45° C., and more preferably in the range of from about 25° C. to about 42° C.

3.1.4 Oxygen/Aeration

Generally speaking, microbial production of glycerate and/or downstream product from glucose results in the formation of NAD(P)H, redox cofactors that are to be converted back to NAD(P)+ in order to maintain catabolism of glucose. Under aerobic conditions, microbes will commonly use molecular oxygen as an electron acceptor to reoxidize these cofactors. If the fermentation is not appropriately oxygenated, glycerate and/or downstream product production will decrease. During cultivation, aeration and agitation conditions are selected to produce an oxygen transfer rate (OTR; rate of dissolution of dissolved oxygen in a fermentation medium) that results in glycerate and/or downstream product formation. In various embodiments, fermentation conditions are selected to produce an OTR of greater than 10 mmol/l/hr. In some embodiment, fermentation conditions are selected to produce an OTR of greater than 20 mmol/l/hr, greater than 30 mmol/l/hr, greater than 40 mmol/l/hr, greater than 50 mmol/l/hr, greater than 75 mmol/l/hr, greater than 100 mmol/l/hr, greater than 125 mmol/l/hr, greater than 150 mmol/l/hr, greater than 175 mmol/l/hr, or greater than 200 mmol/l/hr. OTR, as used herein, refers to the volumetric rate at which oxygen is consumed during the fermentation. Inlet and outlet oxygen concentrations can be measured by exhaust gas analysis, for example by mass spectrometers. OTR can be calculated using the Direct Method described in Bioreaction Engineering Principles $3^{rd}$ Edition, 2011, Spring Science+Business Media, p. 449. The recombinant host cells of the present disclosure are able to produce glyceric acid and/or downstream product(s) under a wide range of oxygen concentrations.

3.1.5 Yields and Titers

A high yield of glycerate and/or downstream product from the provided carbon source(s) is desirable to decrease the production cost. As used herein, yield is calculated as the percentage of the mass of carbon source catabolized by recombinant host cells of the present disclosure and used to produce glycerate and/or downstream product. In some cases, only a fraction of the carbon source provided to a fermentation is catabolized by the cells, and the remainder is found unconsumed in the fermentation broth or is consumed by contaminating microbes in the fermentation. Thus, fermentation ought to be both substantially pure of contaminating microbes and that the concentration of unconsumed carbon source at the completion of the fermentation is measured. For example, if 100 grams of glucose is fed into the fermentation, and at the end of the fermentation 25 grams of glycerate is produced and there remains 10 grams of glucose, the glycerate yield is 27.7% (i.e., percentage of 25 grams glycerate produced per 90 grams glucose consumed). In certain embodiments of the methods provided herein, the final yield of glycerate on the carbon source is at least 10%, at least 20%, at least 30%, at least 35%, at least 40%, at least 50%, at least 60%, at least 70%, at least 80%, or greater than 80%. In certain embodiments, the recombinant host cells provided herein are capable of producing at least 70%, at least 75%, or greater than 80% by weight of carbon source to glycerate. When a glycerate salt is found in the fermentation broth, the glyceric acid yield can be determined by calculating the mols of glycerate salt present and adjusting for the molecular weight difference between the glycerate salt and glyceric acid.

In addition to yield, the titer (or concentration), of glycerate and/or downstream product produced in the fermentation, is another metric for production. Assuming all other metrics are equal, a higher titer is preferred to a lower titer. Generally speaking, titer is provided as grams of product (for example, glycerate or downstream product) per liter of fermentation broth (i.e., g/l). In some embodiments, the glyceric acid or glycerate salt titer is at least 1 g/l, at least 5 g/l, at least 10 g/l, at least 15 g/l, at least 20 g/l, at least 25 g/l, at least 30 g/l, at least 40 g/l, at least 50 g/l, at least 60 g/l, at least 70 g/l, at least 80 g/l, at least 90 g/l, at least 100 g/l, or greater than 100 g/l at some point during the fermentation, and preferably at the conclusion of the fermentation. As with yield calculations, a glyceric acid titer can be calculated from the glycerate salt titer by adjusting for molecular weight differences between the glycerate salt and glyceric acid.

Further, productivity, or the rate of product (i.e., glycerate or downstream product) formation, is useful in decreasing production cost, and, assuming all other metrics are equal a higher productivity is preferred over a lower productivity. Generally speaking, productivity is provided as grams product produced per liter of fermentation broth per hour (i.e., g/l/hr). In some embodiments, glyceric acid and/or downstream product productivity is at least 0.1 g/l/hr, at least 0.25 g/l/hr, at least 0.5 g/l/hr, at least 0.75 g/l/hr, at least 1.0 g/l/hr, at least 1.25 g/l/hr, at least 1.25 g/l/hr, at least 1.5 g/l/hr, or greater than 1.5 g/l/hr over some time period during the fermentation.

HPLC is an appropriate method to determine the amount of glycerate or downstream product produced, the amount of any byproducts produced (for example, organic acids and alcohols), the amount of any pathway metabolite or intermediate produced, and the amount of unconsumed glucose left in the fermentation broth. Aliquots of fermentation broth can be isolated for analysis at any time during fermentation, as well as at the end of fermentation. Briefly, molecules in the fermentation broth are first separated by liquid chromatography (LC); then, specific liquid fractions are selected for analysis using an appropriate method of detection (for example, UV-VIS, refractive index, and/or photodiode array detectors). In some embodiments of the present disclosure, a salt (for example, glycerate or downstream product) is the fermentative product present in the fermentation broth. The salt is acidified before or during HPLC analysis to produce glyceric acid or corresponding organic acid of a downstream product. Hence, the acid concentration calculated by HPLC analysis can be used to calculate the salt titer in the fermentation broth by adjusting for difference in molecular weight between the two compounds.

Gas chromatography-mass spectrometry (GC-MS) is also an appropriate method to determine the amount of target product and byproducts, particularly if they are volatile. Samples of fermentation can be isolated any time during and after fermentation and volatile compounds in the headspace can be extracted for analysis. Non-volatile compounds in the fermentation medium (for example, organic acids) can also be analyzed by GC-MS after derivatization (i.e., chemical alteration) for detection by GC-MS. Non-volatile compounds can also be extracted from fermentation medium by sufficiently increasing the temperature of the fermentation medium, causing non-volatile compounds to transition into gas phase for detection by GC-MS. Molecules are carried by an inert gas carries as they move through a column for separation and then arrive at a detector.

Section 4: Purification of Fermentation Products Glyceric Acid, Glycerates, Glycolic Acid and Glycolates The present disclosure describes the methods for purifying fermentation product synthesized by recombinant cells of the present disclosure, wherein the fermentation product comprises glyceric acid, glycerates, glycolic acid, and glycolates. The methods comprise separating soluble fermentation product from fermentation broth, cells, cell debris and soluble impurities, and isolating the soluble fermentation product. In some examples, the methods may also comprise converting fermentation product from soluble form to insoluble, crystalline form, and isolating the crystalline fermentation product.

At the end of fermentation, the fermentation broth contains fermentation product, in soluble and/or insoluble forms, together with biomass and soluble impurities that comprise salts, proteins, unconverted sugars, and other impurities including color bodies. Biomass and soluble impurities are removed via a series of purification steps. In certain embodiments of the present disclosure, purification steps may comprise centrifugation, microfiltration, ultrafiltration, nanofiltration, diafiltration, ion exchange, crystallization, and any combination thereof. In some of these embodiments, ion exchange resins and nanofiltration membranes are used as polishing steps to remove trace amounts of soluble impurities, unconverted sugars and color bodies.

4.1 Removal of Cells and Cell Debris

In some embodiments, the method of purifying fermentation product (i.e., glyceric acid, glycerates, glycolic acid, and glycolates) comprises a step of separating a liquid fraction containing fermentation product from a solid fraction that contains cells and cell debris. For this separation, any amount of fermentation broth can be processed, including the entirety of the fermentation broth. The amount of fermentation broth processed can depend on the type of fermentation method used, such as batch or continuous fermentation methods. In various embodiments, removal of cells and cell debris can be accomplished, for example, via centrifugation using specific g-forces and residence times, and/or filtration using molecular weight cutoffs that are suitable for efficiently separating the liquid fraction containing fermentation product from the solid fraction that contains cells and cell debris. In some embodiments, removal of cells and cell debris is repeated at least once at one or in more than one step in the methods provided herein.

In some embodiments, centrifugation is used to provide a liquid fraction comprising fermentation product that is substantially free of cells. Many types of centrifuges useful for the removal of cells and solids from fermentation broth are known to those skilled in the art, including disc-stack and decanter centrifuges. Centrifuges are well suited for separating solids with a particle size of between 0.5 μm to 500 μm and density greater than that of the liquid phase (ca. 1.0 g/mL). Yeast cells, as a non-limiting example of a fermentation product-producing microbe, typically have a particle size between 4-6 μm and a density of around 1.1 g/mL; therefore, centrifugation is well suited for removing yeast cells from fermentation broth.

In some embodiments, a disc-stack centrifuge is used to provide a liquid fraction comprising fermentation product that substantially free of cells. A disc stack centrifuge separates solids, which are discharged intermittently during operation, from liquids, typically in a continuous process. A disc-stack centrifuge is well suited for separating soft, non-abrasive solids, including cells. In some embodiments, a decanter centrifuge is used to provide a liquid fraction comprising fermentation product that is substantially free of cells. A decanter centrifuge can typically process larger amounts of solids and is often preferred over a disc-stack centrifuge for processing fermentation broth when the cell mass and other solids exceeds about 3% w/w.

Other methods can be used in addition to, or alone, with the above centrifugation processes. For example, microfiltration is also an effective means to remove cells from fermentation broth. Microfiltration includes filtering the fermentation broth through a membrane having pore sizes from about 0.5 μm to about 5 μm. In some embodiments, microfiltration is used to provide a liquid fraction comprising fermentation product that is substantially free of cells.

In some embodiments, cells removed by centrifugation and/or microfiltration are recycled back into the fermentation. Recycling cells back into the fermentation can increase fermentation product yield since less carbon source (for example, glucose) is to be used to generate new cells. Additionally, recycling cells back into the fermentation can also increase fermentation product productivity since the concentration of cells producing glycerate and/or downstream product in the fermenter can be increased.

While suitable for removing cells, centrifugation and microfiltration are not generally not effective at removing cells debris, proteins, DNA and other smaller molecular weight compounds from the fermentation broth. Ultrafiltration is a process similar to microfiltration, but the membrane has pore sizes ranging from about 0.005 μm to 0.1 μm. This pore size equates to a molecular weight cut-off (the size of macromolecule that will be ca. 90% retained by the membrane) from about 1,000 Daltons to about 200,000 Daltons. The ultrafiltration permeate will contain low-molecular weight compounds, including fermentation product and various other soluble salts while the ultrafiltration retentate will contain the majority of residual cell debris, DNA, and proteins. In some embodiments, ultrafiltration is used to provide a liquid fraction comprising glycerate salts that is substantially free of cell debris and proteins.

4.2 Nanofiltration and Ion Exchange Polishing of Clarified Fermentation Broth Containing Fermentation Product In some embodiments, nanofiltration is used to separate out certain contaminating salts, sugars, color forming bodies, and other organic compounds present in clarified fermentation broth containing fermentation product (i.e., glyceric acid, glycerates, glycolic acid, and glycolates). In nanofiltration, the clarified fermentation broth (i.e., the fermentation broth resulting from the combination of centrifugation, microfiltration, and/or ultrafiltration steps described above) is filtered through a membrane having pore sizes ranging from 0.0005 µm to 0.005 µm, equating to a molecular weight cut-off of about 100 Daltons to about 2,000 Daltons. Nanofiltration can be useful for removing divalent and multivalent ions, maltose and other disaccharides (for example, sucrose), polysaccharides, and other complex molecules with a molecular weight larger than fermentation product (for example, sodium glycerate 128.059 g/mol, potassium glycerate 144.167 g/mol or calcium glycerate 286.246 g/mol). Non-limiting examples of nanofiltration materials comprise ceramic membranes, metal membranes, polymer membranes, and composite membranes.

In some embodiments, ion exchange is used to remove specific contaminating salts present in clarified fermentation broth containing fermentation product. Ion exchange elements can take the form of resin beads as well as membranes. Frequently, the resins are cast in the form of porous beads. The resins can be cross-linked polymers having active groups in the form of electrically charged sites. At these sites, ions of opposite charge are attracted but may be replaced by other ions depending on their relative concentrations and affinities for the sites. Ion exchangers can be cationic or anionic. Factors that determine the efficiency of a given ion exchange resin include the favorability for a given ion, and the number of active sites available.

A combination of nanofiltration and ion exchange steps can be combined to produce a purified solution of fermentation product from clarified fermentation broth.

4.3 Crystallization of Fermentation Product

Fermentation product (i.e., glyceric acid, glycerates, glycolic acid, and glycolates) purified as described thus far are crystallized to further remove water and any remaining trace, water-soluble impurities. The solution of purified fermentation product as produced by the aforementioned steps is then fed to the fermentation product crystallization step. In some embodiments of the present disclosure, the majority of one or more glycerate salts is recovered in an insoluble, crystallized form with a minor fraction of glycerate salt remaining in the mother liquor. In other embodiments, the majority of the glyceric acid is recovered in an insoluble, crystallized form with a minor fraction of glyceric acid remaining in the mother liquor.

In some embodiments of the present disclosure, the temperature of the mother liquor is changed to facilitate fermentation product crystallization. In some embodiments, the mother liquor is cooled to a temperature below 20° C. to decrease fermentation product solubility. In some these embodiments, the mother liquor is heated to evaporate excess water. In some of these embodiments, evaporative crystallization is preferred as it offers a high yield of fermentation product and prevents the formation of stable gels, which may occur if temperature is reduced below the gelling point of concentrated fermentation product solutions. In some of these embodiments, fermentation product crystallization is achieved by combining various heating and cooling steps. In some of these embodiments, supersaturation is achieved by evaporative crystallization wherein the solute is more concentrated in a bulk solvent that is normally possible under given conditions of temperature and pressure; increased supersaturation of fermentation product in the mother liquor causes the fermentation product to crystallize. Non-limiting examples of crystallizers comprise forced circulation crystallizers, turbulence/draft tube and baffle crystallizers, induced circulation crystallizers and Oslo-type crystallizers.

In some embodiments of the present disclosure, the aforementioned heating step, cooling step and change in pH are combined in various ways to crystallize fermentation product, and modified as needed, as apparent to practitioners skilled in the art.

In some embodiments, insoluble fermentation product crystals (for example, calcium glycerate or calcium glycolate) is formed during the fermentation and the resulting product crystals are isolated. Fermentation product crystals can be isolated from the mother liquor by any technique apparent to those of skill in the art. In some embodiments of the present disclosure, fermentation product crystals are isolated based on size, weight, density, or combinations thereof. Fermentation product crystal isolation based on size can be accomplished, for example, via filtration, using a filter with a specific particle size cutoff. Fermentation product crystal isolation based on weight or density can be accomplished, for example, via gravitational settling or centrifugation, using, for example, a settler, decanter centrifuge, disc-stack centrifuge, basket centrifuge, or hydrocyclone wherein suitable g-forces and settling or centrifugation times can be determined using methods known in the art. In some embodiments in which the fermentation product is calcium glycerate, the calcium glycerate crystals are isolated from the mother liquor via settling for from 30 minutes to 2 hours at a g-force of 1. In other embodiments in which the fermentation product is calcium glycerate, the calcium glycerate crystals are isolated from the fermentation broth via centrifugation for 20 seconds to 60 seconds at a g-force of from 275 x-g to 1,000 x-g.

Following isolation from the mother liquor, fermentation product crystals are wet with residual mother liquor that coats the crystals. Thus, it is useful to wash the fermentation product crystals with water to remove these trace impurities that may be in the mother liquor. When washing fermentation product crystals, it is useful to minimize the dissolution of isolated crystals in the wash water; for this reason, cold wash (around 4° C.) water is generally used. Additionally, it is useful to minimize the amount of wash water used to minimize crystal dissolution. In many embodiments, less than 10% w/w wash water is used to wash the fermentation product crystals.

In some embodiments, the methods further comprise the step of removing impurities from fermentation product crystals. Impurities may react with fermentation product crystals and reduce final yields, or contribute to fermentation product crystals of lesser purity that limits industrial utility. Non-limiting examples of impurities comprise acetic acid, succinic acid, malic acid, ethanol, glycerol, pyruvic acid, citric acid, and propionic acid. In some embodiments, removal of such impurities is accomplished by dissolving the isolated fermentation product crystals into an aqueous solution and recrystallizing the fermentation product. A non-limiting example of dissolving and recrystallizing fermentation product crystals can comprise dissolving the fermentation product in water and evaporating the resulting aqueous solution (as mentioned above), and finally re-isolating the fermentation product crystals by filtration and/or centrifugation. None, one, or more than one cycle of fermentation product recrystallization may be used so long as the resulting fermentation product are of suitable quality.

In some embodiments, no fermentation product recrystallizations are performed. In other embodiments, one fermentation product recrystallization is performed. In still further embodiments, more than one fermentation product recrystallization is performed.

In some embodiments of the present disclosure, fermentation product crystals are dewatered using a combination of screening and drying methods apparent to practitioners skilled in the art. In some of these embodiments, crystal dewatering steps comprise centrifugation, belt drying, filtration, application of vacuum, or a combination thereof. In some of these embodiments, vacuum is applied at 20 mm of Hg below atmospheric pressure. Suitable devices for crystal dewatering may include a Horizontal Vacuum Belt Filter (HVBF) or a Rotary Drum Vacuum Filter (RDVF). Fermentation product crystal isolation based on size can be accomplished, for example, via filtration, using, for example, a filter press, candlestick filter, or other industrially used filtration system with appropriate molecular weight cutoff. Fermentation product crystal isolation based on weight or density can be accomplished, for example, via gravitational settling or centrifugation, using, for example, a settler, decanter centrifuge, disc-stack centrifuge, basket centrifuge, or hydrocyclone, wherein suitable g-forces and settling or centrifugation times can be determined using methods known in the art.

In some embodiments of the present disclosure, fermentation products are crystallized in the fermentation broth prior to removal of cells, cell debris, contaminating salts and various soluble impurities. In many of these embodiments, the fermentation product crystals are separated from fermentation broth, cells, cell debris, contaminating salts and various soluble impurities by sedimentation, centrifugation, ultrafiltration, nanofiltration, ion exchange, or any combination thereof.

Section 5: Esterification of Glycerate Salts and Recovery of Esterification Products 5.1 Esterification of Glycerate Salt for Glycerate Ester Production This disclosure provides methods for esterification of glycerate using supercritical carbon dioxide ($sCO_2$) and alcohol to produce a glycerate ester.

The method for esterification of glycerate comprises incubating a reaction mixture for a sufficient period of time to allow for formation of one or more esterification products, wherein the reaction mixture comprises: (1) a glycerate salt; (2) $sCO_2$; (3) a catalyst; and (4) an alcohol co-solvent. In some embodiments, the esterification method is repeated one or more times. In some embodiments, the esterification method further comprises a step that separates the glycerate ester product from leftover reaction components, reaction intermediates, and/or byproducts. In some embodiments, the esterification method is performed using a one-pot synthesis strategy.

In some embodiments, the glycerate salt is purified from recombinant host cells. In some embodiments, the glycerate salt is dissolved, dried, dewatered, and/or concentrated before esterification. In many embodiments, the glycerate salt is sodium glycerate. In other embodiments, the glycerate salt is calcium glycerate.

This disclosure provides methods for esterification of glycerate using an alcohol and esterification catalyst (see, for example, Section 5 of the present disclosure). In some embodiments, the esterification catalyst is selected from the group consisting of one or more mineral acids, organic acids, and solid acid catalyst. Examples of mineral acid catalysts that can be used in accordance with the methods of this disclosure comprise, but are not limited to, sulfuric acid, hydrochloric acid, nitric acid, phosphoric acid, boric acid, hydrofluoric acid, or hydrobromic acid. In some embodiments, the mineral acid catalyst is sulfuric acid ($H_2SO_4$). Examples of organic acid catalysts that can be used in accordance with the methods of this disclosure comprise, but are not limited to, formic acid and acetic acid. In some embodiments, the organic acid catalyst is acetic acid. An example of a solid acid catalyst useful accordance with the methods of this disclosure is a solid acid catalyst such as Amberlyst-15. In some embodiments, the solid acid catalyst is an acidic ion exchange resin.

In some embodiments, the co-solvent is an esterification alcohol. In some embodiments, the co-solvent is selected from the group comprising methanol, 1-propanol, 2-propanol, 1-butanol, isobutanol, 1-hexanol, 3-pentanol, and ethanol (EtOH). In some embodiments, the co-solvent(s) is recovered from the downstream distillation step and reused in the esterification step.

The reaction can be carried out in a distillation column, a jacketed glass reactor with a condenser, a Parr stirred reactor system, or other appropriate reaction vessel as deemed appropriate by skilled practitioners in the art. During the glycerate salt dissolution and esterification processes, the reaction mixture is often mixed.

In some embodiments of the present disclosure, the esterification conditions comprise a temperature within the range of 150° C. to 300° C., and a reaction pressure within the range of 1 atm to 10 atm. In some embodiments, the esterification conditions comprise a temperature that does not exceed the boiling point of the esterification alcohol. In some embodiments, the esterification conditions comprise a temperature greater than 25° C.

In some embodiments, the esterification conditions comprise a pressure within the range of 500 psi to 2,000 psi, depending on the temperature.

5.2 Distillation of Glycerate Esters

In various embodiments of the present disclosure, the glycerate ester is purified via distillation from esterification reaction mixtures (filtered or unfiltered), which are both described above. The reaction mixtures are distilled according to methods known to practitioners skilled in the art to separate unconverted esterification alcohol and partially converted species.

In some embodiments, distillation temperature is maintained within the range of 50° C. to 300° C., depending on the pressure. In some embodiments, distillation temperature is maintained within the range of 50° C. to 100° C. Distillation temperature refers to the temperature measured at the bottom of the distillation vessel.

In some embodiments, the distillation pressure is maintained within the range of 0 Torr to 100 Torr, depending on the temperature. In some embodiments, distillation pressure is maintained within the range of 2 kPa to 6 kPa.

Purified glycerate esters can be analyzed by a variety of methods known to practitioners skilled in the art, including HPLC (high-performance liquid chromatography) and GC-MS (gas chromatography mass spectrometry). Chromatography methods are useful for reporting the percentage product purity as a percentage of total measured organic compounds. In some embodiments, glycerate ester purity as a percentage of total organic compounds is greater than 95%. In some embodiments, glycerate ester purity as a percentage of total organic compounds is greater than 98%. In some embodiments, glycerate ester purity as a percentage of total organic compounds is greater than 99%. In some embodiments, glycerate ester purity as a percentage of total organic compounds is greater than 99.5%. In some embodiments, glycerate ester purity as a percentage of total organic compounds is greater than 99.8%.

In addition to chromatographic measurement of purity, a useful measure of product quality is water content and Karl Fischer titration can be used to determine the water content of purified glycerate ester. In some embodiments, the amount of amount of water present in the purified glycerate ester solution is less than 0.1%. In some embodiments, the amount of amount of water present in the purified glycerate ester solution is less than 0.05%.

Another useful measure of product purity is color. The presence or absence of color in purified glycerate ester solution can be measured at the end of distillation, and over a period of time when the product is in storage. Color measurements can be made using a colorimeter such as a HunterLab colorimeter. For near white solutions, the presence or absence of color can be reported according to the Yellowness Index (YI) with calculations according to the ASTM E313 standard. A change in YI over time is a measure of color formation over time. In some embodiments of the present disclosure, YI of purified glycerate ester at the end of distillation is low. In some embodiments, YI of purified glycerate ester remains substantially the same over time. In some embodiments, YI of purified glycerate ester does not change significantly over time. In some embodiments, YI of purified glycerate ester reflects desirable visual and/or optical/photonic properties.

Section 6: Deoxydehydration of Glycerate Ester and Recovery of Deoxydehydration Products The disclosure provides methods for deoxydehydration of glycerate esters to generate acrylate ester products. In a single step, catalytic deoxydehydration removes two hydroxyl groups from vicinal diols, providing alkene functionality with concomitant release of one molecule water as well as oxidation of an alcohol. Glycerates, and in particular glycerate esters, are attractive substrates for deoxydehydration since terminal diols and cis-vicinal diols are more reactive than internal diols and trans-diols. When applied toward a glycerate ester, deoxydehydration provides the cognate acrylate ester, sought after chemicals of great industrial importance. For example, methyl glycerate, ethyl glycerate, butyl glycerate, and 2-ethylhexyl glycerate are transformed into methyl acrylate, ethyl acrylate, butyl acrylate, and 2-ethylhexyl acrylate, respectively, by deoxydehydration. Thus, the present disclosure provides methods to convert glyceric acid, and in particular fermentation-derived glyceric acid, into acrylate esters.

The general method for deoxydehydration of glycerate esters comprises incubating a reaction mixture for a sufficient period of time to allow for formation of one or more deoxydehydration products, wherein the reaction mixture comprises: (1) a glycerate ester reactant; (2) a transition metal-based catalyst; (3) a reducing agent; (4) a solvent; (5) optionally, an acid; and (6) optionally, a gas. In many cases the reducing agent and the solvent are the same. In many embodiments, the glycerate ester reactant is selected from the non-limiting group comprising methyl glycerate, ethyl glycerate, butyl glycerate, and 2-ethylhexyl glycerate. In some embodiments, the glycerate ester is methyl glycerate. In some embodiments, the glycerate ester is ethyl glycerate. In some embodiments, the glycerate ester is butyl glycerate. In yet still further embodiments, the glycerate ester is 2-ethylhexyl glycerate. One or more glycerate esters can be included in the same deoxydehydration reaction mixture to generate a corresponding mixture of acrylate ester products. Post deoxydehydration, the different acrylate esters can then be separated, using, for example, fractional distillation, to generate individual, purified acrylate esters.

The catalysts used in the deoxydehydration reaction are transition metal-based catalysts. In many embodiments, the transition metal-based catalyst is selected from the group comprising molybdenum compounds, rhenium compounds, ruthenium compounds, and vanadium compounds. In many of these embodiments, the transition metal-based catalyst is an oxidized molybdenum, oxidized rhenium, oxidized ruthenium, and/or oxidized vanadium compound. The deoxydehydration catalyst can be homogenous or heterogeneous. In many cases, it is advantageous for the deoxydehydration catalyst to be heterogeneous to ease the separation of the catalyst from the reaction mixture.

In some embodiments, the deoxydehydration catalyst is a rhenium compound. In some of these embodiments, the rhenium compound is an oxidized rhenium compound selected from the non-limiting group comprising methyltrioxorhenium (MTO; $CH_3ReO_3$), $HReO_4$, $KReO_4$, $Re_2(CO)_{10}$, $BrRe(CO)_5$, and $NH_4ReO_4$. In particular embodiments, the deoxydehydration catalyst is MTO. Since MTO is a crystalline solid with a simple ligand free structure, it is a particularly advantageous rhenium catalyst. In particular embodiments, the deoxydehydration catalyst is $NH_4ReO_4$.

In some embodiments, the deoxydehydration catalyst is a molybdenum compound. As compared to rhenium, molybdenum is more abundant, and as such it both less expensive and has lower volatility in price. In some of these embodiments, the molybdenum compound is an oxidized molybdenum compound selected from the non-limiting group comprising $(NH_4)_6Mo_7O_{24} \cdot 4H_2O$ (AHM), $MoO_2Cl_2$, $MoO_2(CH_3)_2$, $MoO_2Cl_2$, $MoO_2Br_2$, or $(Bu_4N)_2Mo_6O_{19}$. In specific embodiments, the deoxydehydration catalyst is AHM, a particularly cheap and commercially available catalyst.

In some embodiments, the deoxydehydration catalyst is a vanadium compound. In some of these embodiments, the vanadium compound is an oxidized vanadium compound selected from the non-limiting group comprising $NH_4VO_3$ (ammonium metavanadate), $(nBu_4N)[VO_2(N-(2-benzylidene)thiophene-2-carbohydrazide)]$, and $[Bu_4N][VO_2(pyridine-2,6-dicarboxylate)]$.

In particular embodiments, the catalyst is a ruthenium compound. In some of these embodiments, the ruthenium compound is $(Cp*Ru(CO)_2)_2$.

Catalyst cost is a factor in development of a low-cost synthetic deoxydehydration process. Generally speaking, it is desirable to run the reaction with low catalyst loading (i.e., the molar percentage of catalyst to reactant). In many embodiments, the catalyst loading is less than 10% (percent mol-catalyst per mol-reactant). In some embodiments, catalyst loading is less than 5%. In yet still further embodiments, catalyst loading is less than 2.5%.

A reducing agent is required in the reaction mixture that donates electrons to the glycerate ester. Any reducing agent is suitable for use in accordance with the methods of this disclosure so long as the glycerate ester can be reduced to the corresponding acrylate ester. Often times the reducing agent is also used as the solvent, and in these cases, it is advantageous for the glycerate ester to be reasonably soluble in the reducing agent. Primary and secondary alcohols make, generally speaking, good reductants and solvents for transformation of glycerate esters to acrylate esters.

In some embodiments, the reducing agent is selected from the group comprising PPh$_3$, H$_2$, Na$_2$SO$_3$, benzene, toluene, 5-nonanol, 3-octanol, 2-octanol, 1-butanol, 3-pentanol, 2-methyl-1-butanol, isopropanol, and 2-ethylhexanol. In some embodiments, the reducing agent is H$_2$. In many embodiments, the reducing agent is an alcohol. Small alcohols are generally ineffective reductants and four carbon or higher chain length alcohols provide higher product yields as compared to alcohols less than three carbons. For this reason, n-butanol and 2-ethylhexanol are particularly attractive reducing agents; additionally, the two alcohols are relatively inexpensive, are good solvents in which glycerate esters are soluble, and the corresponding acrylate esters, butyl acrylate and 2-ethylhexyl acrylate, are articles of commerce. In some embodiments, the reductant is n-butanol. In other embodiments, the reductant is 2-ethylhexanol.

When the reductant included in the deoxydehydration reaction mixture is a primary alcohol it is often times advantageous for the alkyl group of the glycerate ester to be the same as the primary alcohol used as the reductant. For example, when the reductant is 1-butanol the reactant is butyl glycerate. This can reduce the formation of unwanted acrylate ester byproducts generated when the two alcohol groups are different. In some embodiments when the glycerate ester is butyl glycerate, the reductant is 1-butanol and the product is butyl acrylate. In some embodiments where the glycerate ester is 2-ethylhexyl glycerate, the reductant is 2-ethylhexyanol and the product is 2-ethylhexyl acrylate.

The deoxydehydration reaction can be performed at any temperature so long as the reactant is converted to its cognate reduced product at appreciable yields. Maintaining the deoxydehydration reaction temperature at above ambient temperature, however, is useful for increasing the reaction rate and often times the product yield. The temperature of the reaction mixture may be held at an elevated temperature for some or all of the reaction period. In some instances, and in particular when the reactant is heat labile, reaction yields can be increased by running the reaction at a lower temperature for a period of time and then raising the reaction temperature to complete the reaction (i.e., increase the percentage conversion of reactant to product). In some embodiments, the temperature of the reaction mixture is above 25° C. In some embodiments, the temperature of the reaction mixture ranges from 150° C. to 300° C.

In some embodiments, the solvent is selected from the group comprising benzene, chlorobenzene, ethanol, methanol, butanol, isopropyl alcohol, 2-ethylhexanol, and 3-pentanol.

In some embodiments, the gas is selected from the group comprising nitrogen, argon, or hydrogen. In some embodiments, the deoxydehydration reaction is carried out in air. In some embodiments, the deoxydehydration reaction is carried out in nitrogen.

In some embodiments, the reaction time ranges from 1 hour to 24 hours.

In some embodiments, the deoxydehydration reaction is carried out at atmospheric pressure. In some embodiments, the deoxydehydration reaction is carried out with the pressure range of 50 psi to 300 psi.

In some embodiments, the deoxydehydration method is repeated one or more times. In some embodiments, the deoxydehydration method further comprises a step that separates the product from leftover reaction components, reaction intermediates, and/or byproducts. In some embodiments, the deoxydehydration method is performed using a one-pot synthesis strategy.

Section 7: Poly(Glycerate Carbonate) Compounds and Methods

In one aspect, provided herein is a poly(glycerate carbonate) compound comprising repeat units of formula (I) or a salt thereof:

—[OCH(C(=O)OR$^1$)CH$_2$OC(=O)]— (I)

wherein each R$^1$ is independently hydrogen, optionally substituted C$_1$-C$_5$ alkyl, and optionally substituted aryl.

In one embodiment, the compound provided comprises repeat units of formula (IA): —[OCH(C(=O)OCH$_3$)CH$_2$OC(=O)]— (IA). In another embodiment, the compound provided comprises repeat units of formula (IB): —[OCH(C(=O)OC$_2$H$_5$)CH$_2$OC(=O)]— (IB). In another embodiment, the compound provided comprises repeat units of formula (IC): —[OCH(C(=O)OC$_3$H$_7$)CH$_2$OC(=O)]— (IC). In another embodiment, the compound provided comprises repeat units of formula (ID): —[OCH(C(=O)OC$_4$H$_9$)CH$_2$OC(=O)]— (ID).

The disclosure provides methods for conversion of glyceric acid, glycerate esters, and glycerate epoxides to generate poly(glycerate carbonate) compounds. In one route, glyceric acid is esterified with one or more alcohols to generate the corresponding glycerate ester(s) which is subsequently reacted with carbon dioxide to generate the poly(glycerate carbonate) compound. In a second, alternative route, the vicinal diol of the glycerate ester(s) is converted to an epoxide, and the resulting glycidate epoxide is reacted with carbon dioxide to generate the poly(glycerate carbonate) compound.

The general method for esterification of glyceric acid comprises incubating a reaction mixture for a sufficient period of time to allow for formation of one or more esterification products, wherein the reaction mixture comprises: (1) glyceric acid; (2) a catalyst; and, (3) an alcohol reactant.

In many embodiments, the alcohol reactant is selected from the non-limiting group comprising methanol, ethanol, 1-propanol, 1-butanol, and benzyl alcohol. In some embodiments, the alcohol reactant is methanol and the glycerate ester is methyl glycerate. In some embodiments, the alcohol reactant is ethanol and the glycerate ester is ethyl glycerate. In some embodiments, the alcohol reactant is 1-propanol and the glycerate ester is propyl glycerate. In some embodiments, the alcohol reactant is 1-butanol and the glycerate ester is butyl glycerate. In yet still further embodiments, the alcohol reactant is 2-ethylhexanol and the glycerate ester is 2-ethylhexyl glycerate. One or more alcohol reactants can be included in the same esterification reaction mixture to generate a corresponding mixture of glycerate ester products. Post esterification, the different glycerate esters can then be separated, using, for example, fractional distillation, to generate individual, purified glycerate esters.

In one embodiment, a poly(glycerate carbonate) compound provided herein comprises carbon atoms all of which are non-petrochemical based carbons or having $^{14}$C amounts substantially higher than zero such as about 0.5 or 1 parts per trillion or more. In one embodiment, a poly(glycerate carbonate) compound provided herein comprises carbon atoms substantially all of which are non-petrochemical based carbons or having $^{14}$C amounts substantially higher than zero such as about 0.5 or 1 parts per trillion or more.

In one embodiment, the poly(glycerate carbonate) compounds provided herein comprises an alkyl glycerate moiety which comprises a carbon-backbone having all carbon atoms that are non-petrochemical based carbons or having $^{14}C$ amounts substantially higher than zero such as about 0.5 or 1 parts per trillion or more. In another embodiment, the poly(glycerate carbonate) compounds provided herein comprise an alkyl glycerate moiety which comprises a carbon-backbone having substantially all carbon atoms that are non-petrochemical based carbons or having $^{14}C$ amounts substantially higher than zero such as about 0.5 or 1 parts per trillion or more In one embodiment, the poly(glycerate carbonate) compounds provided herein comprises a $^{14}C$ amount substantially higher than zero, such as about 0.5, or 1 parts per trillion or more.

In some embodiments, the method comprises an alkyl glycerate moiety which comprises a carbon-backbone having all or substantially all carbon atoms that are non-petrochemical based carbons or having $^{14}C$ amounts substantially higher than zero such as about 0.5 or 1 parts per trillion or more.

In another aspect, provided herein is a poly(glycerate carbonate) compound provided by the methods provided herein.

In another aspect, provided herein is an article or manufacture comprising the poly(glycerate carbonate) compound provided herein. In some embodiment, the article of manufacture is superabsorbent polymer.

In some embodiments, the poly(glycerate carbonate) provided herein can be extruded to form fibers or films. Such techniques are well known. The fibers can be twisted to form yarns which can be woven into fabrics which are useful in the manufacture of wearing apparel and for numerous other purposes. The films can be employed for the wrapping of various packaged products and for use as a dielectric in the manufacture of electrical condensers, electric motors, transformers, etc.

In some embodiments the poly(glycerate carbonate) provided herein can be converted into a hydrogel. The hydrogel properties can be tailored by controlling degree of cross linking and functional side groups and employed in applications such as hygiene, drug delivery, tissue engineering, food additives, wound dressings and biomedical applications.

In another aspect, the poly(glycerate carbonate) compounds provided herein are degradable through hydrolytic or biological action to provide functional or stimuli-responsive degradation at end-of-life and avoid accumulation of harmful materials in the environment.

In another aspect, the poly(glycerate carbonate) compounds provided herein are bioabsorbable to provide functional or stimuli-responsive degradation in-vivo after performing the desired purpose such as drug release or providing a scaffold for in-growth of tissue with.

Section 8: Examples

Parent Strain Used in the Examples

The parent strain in Example 1 was a *P. kudriavzevii* strain auxotrophic for histidine and uracil due to genetic disruptions in URA2 and HIS3 (i.e., the strain cannot grow in media without histidine and uracil supplementation). Histidine auxotrophy in the parent strain enables selection of new, engineered strains that carry a HIS3 marker, enabling histidine prototrophy and indicating desired nucleic acid modification. Likewise, uracil auxotrophy in the parent strain enables selection of new, engineered strains that carry a URA2 marker, enabling uracil prototrophy and indicating desired nucleic acid modification. Thus, cells that were successfully modified with exogenous nucleic acids to comprise desired genetic modifications can grow in media without histidine and/or uracil supplementation, dependent on the selection marker included in the exogenous nucleic acid. Following confirmation of correct strain engineering, the selection marker(s) were removed by, for example, homologous recombination and marker loopout. Removing the marker enables subsequent rounds of strain engineering using the same selection markers.

Media Used in the Examples

Complete supplement mixture (CSM) medium. CSM medium comprised Adenine 10 mg/L; L-Arginine HCl 50 mg/L; L-Aspartic Acid 80 mg/L; L-Histidine HCl 20 mg/L; L-Isoleucine 50 mg/L; L-Leucine 100 mg/L; L-Lysine HCl 50 mg/L; L-Methionine 20 mg/L; L-Phenylalanine 50 mg/L; L-Threonine 100 mg/L; L-Tryptophan 50 mg/L; L-Tyrosine 50 mg/L; Uracil 20 mg/L; L-Valine 140 mg/L. The YNB used in the CSM comprised Ammonium sulfate 5.0 g/L, Biotin 2.0 µg/L, Calcium pantothenate 400 µg/L, Folic acid 2.0 µg/L, Inositol 2.0 mg/L, Nicotinic acid 0-400 µg/L, p-Aminobenzoic acid 200 µg/L, Pyridoxine HCl 400 µg/L, Riboflavin 200 µg/L, Thiamine HCl 400 µg/L, Boric acid 500 µg/L, Copper sulfate 40 µg/L, Potassium iodide 100 µg/L, Ferric chloride 200 µg/L, Manganese sulfate 400 µg/L, Sodium molybdate 200 µg/L, Zinc sulfate 400 µg/L, Potassium phosphate monobasic 1.0 g/L, Magnesium sulfate 0.5 g/L, Sodium chloride 0.1 g/L, and Calcium chloride 0.1 g/L.

Complete supplement mixture minus histidine (CSM-His) medium. CSM-His medium is identical to CSM medium with the exception that histidine was not included in the medium. Engineered strains auxotrophic for histidine are unable to grow on CSM-His medium while engineered strains containing exogenous nucleic acids comprising a histidine selectable marker (for example, HIS3) are capable of growth in CSM-His medium.

Complete supplement mixture minus uracil (CSM-Ura) medium. CSM-Ura medium is identical to CSM medium with the exception that uracil was not included in the medium. Engineered strains auxotrophic for uracil are unable to grow on CSM-Ura medium while engineered strains containing exogenous nucleic acids comprising a uracil selectable marker (for example, URA2) are capable of growth in CSM-Ura medium.

BM02 medium. BM02 medium is Glucose 125 g/l, $K_2SO_4$ 0.816 g/l, $Na_2SO_4$ 0.1236, $MgSO_4\text{-}7H_2O$ 0.304 g/l, Urea 4.3 g/l, Myo-inositol 2 mg/l, Thiamin HCl 0.4 mg/l, Pyridoxal HCl 0.4 mg/l, Niacin 0.4 mg/l, Ca-Pantothenate 0.4 mg/l, Biotin µg/l, Folic acid 2 µg/l, PABA 200 µg/l, Riboflavin 200 µg/l, Boric acid 0.25 mg/l, Copper sulfate pentahydrate 393 µg/l, Iron sulfate 11.0 mg/l, Manganese chloride 1.6 mg/l, Sodium molybdate 100 µg/l, Zinc sulfate 4 mg/l, and EDTA 11 mg/l.

BM02-P medium. BM02-P medium is BM02 medium with 1 g/l potassium phosphate.

YPE medium. YPE medium is Bacto peptone 20 g/l, Yeast extract 10 g/l, and Ethanol 2% (v/v).

Example 1: Construction of the Recombinant *P. kudriavzevii* Strain LPK151290 with Eliminated Expression of Phosphoglycerate Mutase This example describes the construction of the *P. kudriavzevii* strain LPK151290 that comprises genetic disruption in both native copies of phosphoglycerate mutase, resulting in eliminated expression of phosphoglycerate mutase. The endogenous Gpm1 gene that encodes for phosphoglycerate mutase in *P. kudriavzevii* (PkGPM1; SEQ ID NO: 14) was disrupted to prevent the conversion of 3-PG to 2-PG in the glycolytic pathway. The deliberate, consequential buildup of 3-PG provided ample 3-PG substrate for the glyceric acid pathway, which was constructed as described in Example 3 (see below).

The parent *P. kudriavzevii* strain used in this example was LPK15775—it was diploid and had two copies of Gpm1, providing a GPM plus phenotype (i.e., native phenotype with respect to Gpm1 expression). The parent LPK15775 strain was also auxotrophic for uracil and histidine. Gpm1 in LPK15775 was disrupted by deletion of both gene copies to produce the GPM minus strain LPK151290.

Both copies of Gpm1 in LPK15775 were disrupted by insertion of a HIS3 selectable marker via homologous recombination. The HIS3 selectable marker, amplified by PCR, was provided to the parent LPK15775 strain to complement the histidine auxotrophic deficiency. The HIS3 selectable marker comprised unique upstream and downstream homologous regions for homologous recombination at the *P. kudriavzevii* Gpm1 locus, a transcriptional promoter, a HIS3 coding region, and a transcriptional terminator. The transcriptional promoter 5' of HIS3 was the *P. kudriavzevii* TEF1 promoter (pPkTEF1) and the transcriptional terminator 3' of HIS3 was the *S. cerevisiae* TDH3 terminator (tScTDH3).

The PCR product of the HIS3 selectable marker was purified and provided as exogenous nucleic acids to *P. kudriavzevii*. Transformation was carried out in a single step and gene deletion was achieved by homologous recombination. Transformants were selected on CSM-His medium and successful deletion of both copies of the gene encoding PkGPM1 was confirmed by genetic sequencing of this locus and the flanking regions.

This example produced the GPM minus, LPK151290 strain that cannot convert 3-PG to 2-PG via PkGPM1. Thus, all engineered *P. kudriavzevii* strains derived from this parental strain had the GPM minus phenotype, resulting in disrupted carbon flux through glycolysis downstream of 3-PG.

Example 2: Recombinant *P. kudriavzevii* Strain LPK151290 Produces Low Amounts of Glyceric Acid This example describes the culturing and analysis of the GPM minus strain, LPK151290 (from Example 1), for basal level glyceric acid production before glyceric acid pathway strains were constructed (see Example 3 below). Recall that the parent strain of LPK151290 is LPK15775 (see Example 1). The parent LPK15775 strain expressed native levels of PkGPM1 (i.e., GPM plus) and was also cultured and analyzed for comparison.

In this example, LPK151290 (GPM minus) and LPK15775 (GPM plus) colonies were used to inoculate replicate tubes of 2 mL to 4 mL of YPE medium with 1% glycerol and incubated at 30° C. with shaking at 250 rpm for 20 hours. These replicate tubes of pre-cultures were each pelleted and resuspended in 0.5 mL of BM02-P media with 5% glucose, 1% ethanol and 50 µg/mL uracil, and placed into 96-well plates. The 96-well plate cultures were then incubated at 30° C. with 80% humidity and shaking at 250 rpm. After 48 hours, 1x volume of 12 M HCl was added to 10x volume of culture for each culture sample. The HCl-culture sample mixtures were spin-filtered and frozen for storage. Samples were analyzed by HPLC within 48 hours of harvest.

For HPLC analysis, frozen samples were thawed analyzed by HPLC using a Bio-Rad Aminex 87H column (300×7.8 mm) and a Bio-Rad Fermentation Monitoring column (#1250115; 150×7.8 mm) installed in series, with an isocratic elution rate of 0.8 ml/min with water at pH 1.95 (with sulfuric acid) at 30° C. Refractive index and UV 210 nm measurements were acquired for 35 minutes.

While the LPK15775 GPM plus strain did not produce detectable amounts of glyceric acid, the LPK151290 GPM minus strain produced a yield of 6% (i.e., percentage of the amount of glyceric acid produced per amount of glucose consumed). This result demonstrated that disruption of GPM activity alone was sufficient to produce detectable, albeit low amounts of glyceric acid in a *P. kudriavzevii* strain background, and more generally in microbes. Thus, all engineered *P. kudriavzevii* strains without heterologous nucleic acids that encode the glyceric acid pathway of the present disclosure can produce appreciable amounts of glyceric acid. Incorporation of heterologous nucleic acids that encode the glyceric acid pathway should increase glyceric acid yields (Example 4).

Example 3: Analysis of Strains LPK15775 (GPM Plus) and LPK151290 (GPM Minus) for the Formation of Byproducts Pyruvate, Ethanol, and Acetate Example 3 describes the culturing and analysis of LPK15775 (GPM plus; parent *P. kudriavzevii* strain) and LPK151290 (GPM minus; from Example 1) recombinant host cells for in vivo production of byproducts pyruvate, ethanol and acetate. Native *P. kudriavzevii* cells are capable of producing downstream metabolites pyruvate, ethanol and acetate. The presence of these metabolites indicates that 3-PG is siphoned from the glyceric acid pathway of the present disclosure, thereby causing decreased fermentation yield of glyceric acid and/or downstream product.

In this example, LPK15775 and LPK151290 are cultured and analyzed by HPLC as described above in Example 2. While the GPM plus LPK15775 produce low amounts of pyruvate, ethanol and acetate, the GPM minus LPK151290 produce relatively lower amounts of pyruvate, ethanol and acetate. This example demonstrates, in accordance with the present disclosure, the successful decrease of byproducts ethanol and acetate from fermentation by genetic disruption of PkGPM in recombinant *P. kudriavzevii* for glyceric acid and/or downstream product synthesis.

Example 4: Construction of Recombinant *P. kudriavzevii* Strains Expressing Glyceric Acid Pathway Enzymes with Decreased or Eliminated Expression of Phosphoglycerate Mutase Example 4 describes the construction of recombinant host cells of the present disclosure that each comprise heterologous nucleic acids encoding a glyceric acid pathway of the present disclosure. The parent *P. kudriavzevii* strain LPK15775 used in this example was auxotrophic for uracil and histidine. Heterologous nucleic acids encoding 3-PG phosphatases of the glyceric acid pathway were integrated into the PkGPM1 locus. Thus, each strain described in this example not only comprised a glyceric acid pathway, but also comprised a GPM minus phenotype due to eliminated expression of phosphoglycerate mutase.

The heterologous nucleic acids used in this example encoded 3-PG phosphatases of the glyceric acid pathway that were derived from EcGPH; SEQ ID NO: 1, HsGPH; SEQ ID NO: 3, ScPHO13; SEQ ID NO: 9, PkPHO13; SEQ ID NO: 10, PkORF64; SEQ ID NO: 11, PkORF423; SEQ ID NO: 12, or ScYKR070W; SEQ ID NO: 13. Heterologous nucleic acids encoding HsGPH were codon-optimized for yeast and were synthesized and provided by Twist Bioscience. Heterologous nucleic acids encoding ScPHO13 and ScYKR070W were amplified form *Saccharomyces cerevisiae* genomic DNA. Heterologous nucleic acids encoding PkPHO13 and PkORF64, and PkORF423 were amplified from *Pichia kudriavzevii* genomic DNA. Heterologous nucleic acids encoding EcGPH was amplified form *Escherichia coli* genomic DNA. The transcriptional promoters cloned in front (5') of each gene were constitutive and derived from *P. kudriavzevii*. The promoters for EcGPH, HsGPH, ScPHO13, PkPHO13, PkORF64, PkORF423, and ScYKR070W were the *P. kudriavzevii* TDH1 promoter (pPkTDH1). The transcriptional terminators cloned behind (3') of each gene were derived from *S. cerevisiae*. The terminators for EcGPH, HsGPH, ScPHO13, PkPHO13, PkORF64, PkORF423, and ScYKR070W were the *Saccharomyces cerevisiae* PYC2 terminator (tScPYC2). Additionally, a HIS3 marker was included in the heterologous expression cassette to complement the histidine auxotrophic deficiency in the background strain. This HIS3 marker comprised a transcriptional promoter, a HIS3 coding region, and a transcriptional terminator. The transcriptional promoter 5' of HIS3 was the *P. kudriavzevii* TEF1 promoter (pPkTEF1) and the transcriptional terminator 3' of HIS3 was the *S. cerevisiae* TDH3 terminator (tScTDH3). All genetic elements were amplified from various templates with upstream and downstream homologous regions to neighboring genetic elements to drive correct assembly of the full-length pathway. The 5' and 3' ends of the expression cassette comprised regions homologous to the genomic sequences upstream and downstream of the *P. kudriavzevii* GPM1 locus, thereby facilitating integration of the heterologous nucleic acids encoding the glyceric acid pathway enzymes at the GPM1 locus in the *P. kudriavzevii* genome. Consequently, one or both copies of the PkGPM1 gene were deleted from the host genome; thus, genomic integration of the glyceric acid pathway simultaneously decreased or eliminated expression of PkGPM1.

All PCR products were purified and provided as exogenous nucleic acids to *P. kudriavzevii*. Transformation was carried out in a single step. Transformants were selected on CSM-His medium. Successful integration of all nucleic acids encoding glyceric acid pathway enzymes were confirmed by genetic sequencing of this locus and the flanking regions.

This example produced GPM minus strains which also comprised a glyceric acid pathway of the present disclosure with the following strain designations: LPK151910 (with EcGPH; SEQ ID NO: 1), LPK151909 (with HsGPH; SEQ ID NO: 3), LPK151954 (with ScPHO13; SEQ ID NO: 9), LPK152365 (with PkPHO13; SEQ ID NO: 10), LPK152367 (with PkORF64; SEQ ID NO: 11), LPK152366 (with PkORF423; SEQ ID NO:12), and LPK151912 (with ScYKR070W; SEQ ID NO: 13).

Example 5: Recombinant *P. kudriavzevii* Strains LPK151910, LPK151909, LPK151954, LPK152365, LPK152367, LPK152366, and LPK151912 Produced Increased Amounts of Glyceric Acid Example 5 describes the culturing and analysis of recombinant host cells LPK151910, LPK151909, LPK151954, LPK152365, LPK152367, LPK152366, and LPK151912 from Example 4 (GPM minus, with genomic insertion of a glyceric acid pathway). All seven recombinant strains were cultured and analyzed by HPLC according to methods described above in Example 2.

In this example, all recombinant strains with a glyceric acid pathway produced a glyceric acid yield of 10-20% as compared to the lower, 6% product yield achieved when culturing the sister LPK151290 GPM minus strain that lacked a heterologous glyceric acid pathway. This example demonstrates, in accordance with the present disclosure, the expression of heterologous nucleic acids encoding a glyceric acid pathway in recombinant *P. kudriavzevii* increased glyceric acid yields as compared to a host cell lacking the heterologous glyceric acid pathway but otherwise genetically identical.

It should be noted that there are alternative ways of implementing the embodiments disclosed herein. Accordingly, the present embodiments are to be considered as illustrative and not restrictive; various modifications can be made without departing from the spirit of this disclosure. Furthermore, the claims are not to be limited to the details given herein, and are entitled their full scope and equivalents thereof.

```
                         SEQUENCE LISTING

SEQ ID NO: 1. Escherichia coli
MNKFEDIRGV AFDLDGTLVD SAPGLAAAVD MALYALELPV AGEERVITWI
GNGADVLMER ALTWARQERA TQRKTMGKPP VDDDIPAEEQ VRILRKLFDR
YYGEVAEEGT FLFPHVADTL GALQAKGLPL GLVTNKPTPF VAPLLEALDI
AKYFSVVIGG DDVQNKKPHP DPLLLVAERM GIAPQQMLFV GDSRNDIQAA
KAAGCPSVGL TYGYNYGEAI DLSQPDVIYQ SINDLLPALG LPHSENQESK
ND -252

SEQ ID NO: 2. Mycobacterium avium
MNSPPKVSVL ITVTGVDQPG VTATLFEVLS GHGVELLNVE QVVIRHRLTL
GVLVCCPADV ADGPALRHDV EAAIRKVGLD VSIERSDDVP IIREPSTHTI
FVLGRPITAA AFGAVAREVA ALGVNIDLIR GVSDYPVIGL ELRVSVPPGA
DGALRTALNR VSSEEHVDVA VEDYTLERRA KRLIVFDVDS TLVQGEVIEM
LAAKAGAEGQ VAAITDAAMR GELDFAQSLQ QRVATLAGLP ATVIDEVAGQ
LELMPGARTT LRTLRRLGYA CGVVSGGFRR IIEPLAEELM LDYVAANELE
IVDGTLTGRV VGPIIDRAGK ATALREFAQR AGVPMAQTVA VGDGANDIDM
LAAAGLGIAF NAKPALREVA DASLSHPYLD TVLFLLGVTR GEIEAADAID
GEVRRVEIPP E -411
```

SEQUENCE LISTING

SEQ ID NO: 3. *Haemophilus somnus*
MTQFKLIGFD LDGTLVNSLP DLALSINSAL KDVNLPQASE NLVMTWIGNG
ADVLSQRAVD WACKQAEKEL TEDEFKYFKR QFGFYYGENL CNISRLYPNV
KETLEALKAQ GYILAVVTNK PTKHVQPILT AFGIDHLFSE MLGGQSLPEI
KPHPAPFYYL CGKFGLYPKQ ILFVGDSQND IFAAHSAGCA VVGLTYGYNY
NIPIAQSKPD WIFDDFADIL KITQ -224

SEQ ID NO: 4. *Saccharomyces cerevisiae*
MGLTTKPLSL KVNAALFDVD GTIIISQPAI AAFWRDFGKD KPYFDAEHVI
QVSHGWRTFD AIAKFAPDFA NEEYVNKLEA EIPVKYGEKS IEVPGAVKLC
NALNALPKEK WAVATSGTRD MAQKWFEHLG IRRPKYFITA NDVKQGKPHP
EPYLKGRNGL GYPINEQDPS KSKVVVFEDA PAGIAAGKAA GCKIIGIATT
FDLDFLKEKG CDIIVKNHES IRVGGYNAET DEVEFIFDDY LYAKDDLLKW
-250

SEQ ID NO: 5. *Homo sapiens*
MAAAEAGGDD ARCVRLSAER AQALLADVDT LLFDCDGVLW RGETAVPGAP
EALRALRARG KRLGFITNNS SKTRAAYAEK LRRLGFGGPA GPGASLEVFG
TAYCTALYLR QRLAGAPAPK AYVLGSPALA AELEAVGVAS VGVGPEPLQG
EGPGDWLHAP LEPDVRAVVV GFDPHFSYMK LTKALRYLQQ PGCLLVGTNM
DNRLPLENGR FIAGTGCLVR AVEMAAQRQA DIIGKPSRFI FDCVSQEYGI
NPERTVMVGD RLDTDILLGA TCGLKTILTL TGVSTLGDVK NNQESDCVSK
KKMVPDFYVD SIADLLPALQ G -321

SEQ ID NO: 6. *Synechococcus elongatus*
MKIKLLCISL AVLFCSSANA QKKQAKVQPS VFPQTVARPK LVVGMVIDQM
RWDYLYRFYA RYGNGGFKRL INEGFSAENT LIPYTPTLTA CGHSSIYTGS
VPAINGIIGN NWFDPQLGRD VYCVEDKSVK TVGSSSNEGL MSPKNLLVTT
VTDELRMATN FRSKVISVSI KDRGAILPGG HTANGAYWYD DMTGSFISST
HYMQQLPTWV NDFNAQRLPN KYFEQDWNTL YPIETYTEST ADAKPYERTF
KGAKTSSFPH LFKQYANKNY SMMASMPQGN SFTLEFAKAA IPAEKLGQTG
NTDFLAVSLS STDYVGHQFG PNSIELEDTY LRLDKDLEDF FNYLDKTIGK
GNYLLFLTAD HGATHVPGFL RNKMPGGRLL LKVQTDLDSL IFNEFKVRCN
FTIINNQVIF DTDAIKEAKA DYAKIKQSTI DYLVKQDGVL NAVDIKNMGA
VTIPQEIKNK IINGYNARRS GDVYIILDAG WYPTLTPGTG HAAWNPYDSH
IPALFMGWGV KPGKTNKEYY MSDIAPTVSA LLHIQQPSGS IGKVITDLLK
-550

SEQ ID NO: 7. Artificial Sequence
MMTTTMMPIK ITTKEQVQEF LDKYDTFLFD CDGVLWLGDH LLPSVKETLD
LLKSLGKQLI FVTNNSTKSR AAYTKKFAKF GITGVTEDEI FGSSYASAVY
VRDFLKLPPG KDKVWVFGES GIEEELKEMG YETLGGTDPR LDEPGVKFDA
DTSPFLVNGL DPDVGCVVAG LDTKINYHRL AITLQYLQKD NPSVPFVATN
IDSTFPQKGK LLPGAGSIIE SVAFASGRQP DAACGKPNQN MLNSIKAAKP
GLNLDPSRCC MVGDRLNTDM KFGRDGGLGG TLLVLTGIET EERALALSDE
HPAPKYYADK LGDLYELTHN N -321

SEQ ID NO: 8. *Escherichia coli*
MYQVVASDLD GTLLSPDHTL SPYAKETLKL LTARGINFVF ATGRHHVDVG
QIRDNLEIKS YMITSNGARV HDLDGNLIFA HNLDRDIASD LFGVVNDNPD
IITNVYRDDE WFMNRHRPEE MRFFKEAVFQ YALYEPGLLE PEGVSKVFFT
CDSHEQLLPL EQAINARWGD RVNVSFSTLT CLEVMAGGVS KGHALEAVAK
KLGYSLKDCI AFGDGMNDAE MLSMAGKGCI MGSAHQRLKD LHPELEVIGT
NADDAVPHYL RKLYLS -266

SEQ ID NO: 9. *Saccharomyces cerevisiae*
MTAQQGVPIK ITNKEIAQEF LDKYDTFLFD CDGVLWLGSQ ALPYTLEILN
LLKQLGKQLI FVTNNSTKSR LAYTKKFASF GIDVKEEQIF TSGYASAVYI
RDFLKLQPGK DKVWVFGESG IGEELKLMGY ESLGGADSRL DTPFDAAKSP
FLVNGLDKDV SCVIAGLDTK VNYHRLAVTL QYLQKDSVHF VGTNVDSTFP
QKGYTFPGAG SMIESLAFSS NRRPSYCGKP NQNMLNSIIS AFNLDRSKCC
MVGDRLNTDM KFGVEGGLGG TLLVLSGIET EERALKISHD YPRPKFYIDK
LGDIYTLTNN EL -312

SEQ ID NO: 10. *Pichia kudriavzevii*
MTIKIATRGA AEKILDKYDT YLFDCDGVIW IGNELLPSVK ETLELLQSKK
KNLIFVSNNS TKARDQYIEK LAGLGIHGVE LEQIINSCYS TAIYINEVLQ
LDKAKKIWVL GQEGITKEVE KFGYETVTFK DLEAKFQEEE LTVDNIQSLI
DPQVGCVIVG LDFQVTYLKI AITQQYLFDR KIPFIATNID STFPFGKTKL
PGAGSIVEVA SFCSGREPDA ICGKPQSGMM DSILSHHSLN KETTIMVGDR
LNTDMKFGSV NGIDTLLVLT GIEVEESVAN GHSDVTYYAD KLGDLYDLTK
-300

SEQ ID NO: 11. *Pichia kudriavzevii*
MTNSEIQRMS TPVEEVSQQL ESKQDIGFVF DIDGVLLKGK KRIVEATEII
TYLQKEKIPF ILLTNGGGMT EKKRIDFINM TLQLETPIHP DQLIQAHTPM

```
KTLIPHHKRV LICGGPKDDV REVAESYGFE DVIRPVDIIR ANPTIWPYHM
FTDEQIEQWG RDPNDTKLDV DGTGCKENLP IDSILCFNDS RALGAEIQII
SDLLNSENGV LGTRRTVKSS KPSIPIVFSN NDFLWANEFV QPRFAMGVLK
IATQTIYSKI NGGEELEQLT LGKPEKVCYD YAHHILIDWR DVLLGKKKAG
NVCLPQLNNE PLNSPFKKVY MVGDNPESDI TGGNRYNWGT ILVKTGVYQE
GDFERNPEIS KPSLGVFANV KEGVMHALKL NGLA -384

SEQ ID NO: 12. Pichia kudriavzevii
MLSLQFKRLI HSIKKSPVGF AFDIDGVLMQ SKNPILPYAR DTLTLLQDHK
IPFVLLTNGG GQTEASRVSF LNKSLSLKNP LRTSQIVLSH TPMRNLTGKY
NRVLVVGGDD PQTREVAQSY GFQEVIRPID IVREAPNIWP FIRYTREEIQ
ALSKPVDLRQ PIDAAFVFND PRDMGTDTQI VIDALCSENG VLGTRRGIGS
SKPSVPIIFS NMDLLWSTGY PIPRFGQGAF RLTIRELYKQ LNNAELEDIV
LGKPWPVSYT YAENVLNDEW KLLNGDRSGA NEIPELGVKP KEQLVENVYM
VGDNPQSDIS GGNNYGWETI LVETGVYKEG DFHKYPTLAK PTFGIFPNVW
DGVTSALKRH QV -362

SEQ ID NO: 13. Saccharomyces cerevisiae
MIGKRFFQTT SKKIAFAFDI DGVLFRGKKP IAGASDALKL LNRNKIPYIL
LTNGGGFSER ARTEFISSKL DVDVSPLQII QSHTPYKSLV NKYSRILAVG
TPSVRGVAEG YGFQDVVHQT DIVRYNRDIA PFSGLSDEQV MEYSRDIPDL
TTKKFDAVLV FNDPHDWAAD IQIISDAINS ENGMLNTLRN EKSGKPSIPI
YFSNQDLLWA NPYKLNRFGQ GAFRLLVRRL YLELNGEPLQ DYTLGKPTKL
TYDFAHHVLI DWEKRLSGKI GQSVKQKLPL LGTKPSTSPF HAVFMVGDNP
ASDIIGAQNY GWNSCLVKTG VYNEGDDLKE CKPTLIVNDV FDAVTKTLEK
YA -352

SEQ ID NO: 14. Pichia kudriavzevii
MVHKLILVRH GQSEWNEKNL FTGWVDVKLS EKGRQEAVRA GELLKEADIK
PDVLYTSLLT RAIQTANIAL ENADRLHIPV VRSWRLNERH YGALQGKDKA
QTLETYGPEK FQQWRRSFDI PPPPIEDHSE FSQFGEERYS NVDPNVLPKT
ESLALVIDRL LPFWQDVIAK DLLANKTVII TAHGNSLRGL VKHLDNISDD
DIAGLNIPTA IPLVYELDDN LKPIKPAYYL DPEAAAAGAA AVAAQGQKK
-249

SEQ ID NO: 15. Saccharomyces cerevisiae
MTSIDINNLQ NTFQQAMNMS GSPGAVCTSP TQSFMNTVPQ RLNAVKHPKI
LKPFSTGDMK ILLLENVNQT AITIFEEQGY QVEFYKSSLP EEELIEKIKD
VHAIGIRSKT RLTSNVLQHA KNLVCIGCFC IGTNQVDLDY ATSRGIAVFN
SPFSNSRSVA ELVIAEIISL ARQLGDRSIE LHTGTWNKVA ARCWEVRGKT
LGIIGYHIG SQLSVLAEAM GLHVLYYDIV TIMALGTARQ VSTLDELLNK
SDFVTLHVPA TPETEKMLSA PQFAAMKDGA YVINASRGTV VDIPSLIQAV
KANKIAGAAL DVYPHEPAKN GEGSFNDELN SWTSELVSLP NIILTPHIGG
STEEAQSSIG IEVATALSKY INEGNSVGSV NFPEVALKSL SYDQENTVRV
LYIHQNVPGV LKTVNDILSN HNIEKQFSDS NGEIAYLMAD ISSVDQSDIK
DIYEQLNQTS AKISIRLLY -469

SEQ ID NO: 16. Escherichia coli
MKIVIAPDSF KESLSAEKCC QAIKAGFSTL FPDANYICLP IADGGEGTVD
AMVAATGGNI VTLEVCGPMG EKVNAFYGLT GDGKTAVIEM AAASGLMLVA
PEKRNPLLAS SFGTGELIRH ALDNDIRHII LGIGGSATVD GGMGMAQALG
VRFLDADGQA LAANGGNLAR VASIEMDECD PRLANCHIEV ACDVDNPLVG
ARGAAAVFGP QKGATPEMVE ELEQGLQNYA RVLQQQTEIN VCQMAGGGAA
GGMGIAAAVF LNADIKPGIE IVLNAVNLAQ AVQGAALVIT GEGRIDSQTA
GGKAPLGVAS VAKQFNVPVI GIAGVLGDGV EVVHQYGIDA VFSILPRLAP
LAEVLASGET NLFNSARNIA CAIKIGQGIK N -381

SEQ ID NO: 17. Artificial Sequence
MSSPQDINNL QNDLLARARS FQQALNLSGS PGNAVSTSPP TSFGGSFMNQ
LPRRLSRTAA SKPAKALKPF STGDIKILLL ENVNQTARDI FKEQGYQVEF
LKSSLPEDEL IEKIRDVHAI GIRSKTKLTA KVLKHAKNLI VIGCFCIGTN
QVDLEYAAKH GIAVFNSPFS NSRSVAELVI AEIISLARQL GDRSIEMHTG
TWNKVSAKCW EIRGKTLGII GYGHIGSQLS VLAEAMGMNV IYYDVVTIMA
LGTAKQVPTL DELLNKADFV TLHVPETPET KNMISAPQFA AMKDGAYLIN
ASRGTVVDIP ALIQAMKSGK IAGAALDVYP NEPAKNGDGY FNDDLNSWAS
ELRSLKNVIL TPHIGGSTEE AQSAIGVEVA TALVKYINEG NSLGAVNFPE
VSLRSTLDQ PNHVRVLYIH QNVPGVLRTV NEILSNHNIE KQFSDSRGDI
AYLMADISDV DQSDIKDLYE QLEQTSSKIS TRLLYL -486

SEQ ID NO: 18. Escherichia coli
MKIVIAPDSY KESLSASEVA QAIEKGFREI FPDAQYVSVP VADGGEGTVE
AMIAATQGAE RHAWVTGPLG EKVNASWGIS GDGKTAFIEM AAASGLELVP
AEKRDPLVTT SRGTGELILQ ALESGATNII IGIGGSATND GGAGMVQALG
AKLCDANGNE IGFGGGSLNT LNDIDISGLD PRLKDCVIRV ACDVTNPLVG
DNGASRIFGP QKGASEAMIV ELDNNLSHYA EVIKKALHVD VKDVPGAGAA
```

```
            GGMGAALMAF LGAELKSGIE IVTTALNLEE HIHDCTLVIT GEGRIDSQSI
            HGKVPIGVAN VAKKYHKPVI GIAGSLTDDV GVVHQHGIDA VFSVLTSIGT
            LDEAFRGAYD NICRASRNIA ATLAIGMRNA G -381

SEQ ID NO: 19. Pichia kudriavzevii
            MVSPAERLST IASTIKPNRK DSTSLQPEDY PEHPFKVTVV GSGNWGCTIA
            KVIAENTVER PRQFQRDVNM WVYEELIEGE KLTEIINTKH ENVKYLPGIK
            LPVNVVAVPD IVEACAGSDL IVFNIPHQFL PRILSQLKGK VNPKARAISC
            LKGLDVNPNG CKLLSTVITE ELGIYCGALS GANLAPEVAQ CKWSETTVAY
            TIPDDFRGKG KDIDHQILKS LFHRPYFHVR VISDVAGISI AGALKNVVAM
            AAGFVEGLGW GDNAKAAVMR IGLVETIQFA KTFFDGCHAA TFTHESAGVA
            DLITTCAGGR NVRVGRYMAQ HSVSATEAEE KLLNGQSCQG IHTTREVYEF
            LSNMGRTDEF PLFTTTYRII YENFPIEKLP ECLEPVED -388

SEQ ID NO: 20. Pichia kudriavzevii
            MIPRLNPLLN ISHLRGGPKF IGKAIKPSQF EFRKNNFRFN STSTKTGSAR
            TIKSGFLSWS FRAATFTGIA GWLYLTYLVY KETNPGSQSP QTEFSEIGNK
            KKNIVILGSG WGAVSVLKTL DTTKYNVTIV SPRNYFLFTP LLPSVPSGTI
            DIKSICDSIR TIARQTPGEV TYLEAAATDI DPVKKTIKLE HKSQRFLIGD
            AFTSEGDVIE NELSYDYLVY AVGATVNTFG IPGIPEYASY LKEANDATAV
            RQKLFNQIEA SRLLPKDSED RKRLLSFVVC GGGPTGVELA AEIKDYIDQD
            LCKFIPGIEK EMQVTLIEAQ HNVLSMFHPK LIEYTKEVFK QQNLHLQVDT
            MVKKVDDKNV YATYRHPDGK TEDMVIPYGT LVWAGGNAQR KLTRDLSSKI
            IEQKTARRGL LVDEYLKLDG DDSIYAIGDC TFTPNPPTAQ VAHQQGEYLG
            EHFNKLAKID ELNYLITNST DDSTKYSKRL ERAEKAIKPF EYDHQGALAY
            VGSERAVADL HWGSWSTVAL GGTMTFFFWR TAYVSMLLSI RNKILVVTDW
            VKVAIFGRDC SQE -563

SEQ ID NO: 21. Lactococcus lactis
            MKIVVIGTNH AGIATANTLI DRYPGHEIVM IDRNSNMSYL GCGTAIWVGR
            QIEKPDELFY AKAEDFEKKG VKILTETEVS EIDFTNKMIY AKSKTGEKIT
            ESYDKLVLAT GSRPIIPNLP GKDLKGIHFL KLFQEGQAID EEFAKNDVKR
            IAVIGAGYIG TEIAEAAKRR GKEVLLFDAE STSLASYYDE EFAKGMDENL
            AQHGIELHFG ELAQEFKANE KGHVSQIVTN KSTYDVDLVI NCIGFTANSA
            LAGEHLETFK NGAIKVDKHQ QSSDPDVSAV GDVATIYSNA LQDFTYIALA
            SNAVRSGIVA GHNIGGKSIE SVGVQGSNGI SIFGYNMTST GLSVKAAKKI
            GLEVSFSDFE DKQKAWFLHE NNDSVKIRIV YETKNRRIIG AQLASKSEII
            AGNINMFSLA IQEKKTIDEL ALLDLFFLPH FNSPYNYMTV AALNAK
            -446

SEQ ID NO: 22. Saccharomyces cerevisiae
            MSSTDEHIEK DISSRSNHDD DYANSVQSYA ASEGQVDNED LAATSQLSRH
            LSNILSNEEG IERLESMARV ISHKTKKEMD SFEINDLDFD LRSLLHYLRS
            RQLEQGIEPG DSGIAFKNLT AVGVDASAAY GPSVEEMFRN IASIPAHLIS
            KFTKKSDVPL RNIIQNCTGV VESGEMLFVV GRPGAGCSTF LKCLSGETSE
            LVDVQGEFSY DGLDQSEMMS KYKGYVIYCP ELDFHFPKIT VKETIDFALK
            CKTPRVRIDK MTRKQYVDNI RDMWCTVFGL RHTYATKVGN DFVRGVSGGE
            RKRVSLVEAQ AMNASIYSWD NATRGLDAST ALEFAQAIRT ATNMVNNSAI
            VAIYQAGENI YELFDKTTVL YNGRQIYFGP ADKAVGYFQR MGWVKPNRMT
            SAEFLTSVTV DFENRTLDIK PGYEDKVPKS SSEFEEYWLN SEDYQELLRT
            YDDYQSRHPV NETRDRLDVA KKQRLQQGQR ENSQYVVNYW TQVYYCMIRG
            FQRVKGDSTY TKVYLSSFLI KALIIGSMFH KIDDKSQSTT AGAYSRGGML
            FYVLLFASVT SLAEIGNSFS SRPVIVKHKS YSMYHLSAES LQEIIITEFPT
            KFVAIVILCL ITYWIPFMKY EAGAFFQYIL YLLTVQQCTS FIFKFVATMS
            KSGVDAHAVG GLWVLMLCVY AGFVLPIGEM HHWIRWLHPI NPLTYAFESL
            VSTEFHHREM LCSALVPSGP GYEGISIANQ VCDAAGAVKG NLYVSGDSYI
            LHQYHFAYKH AWRNWGVNIV WTFGYIVFNV ILSEYLKPVE GGGDLLLYKR
            GHMPELGTEN ADARTASREE MMEALNGPNV DLEKVIAEKD VFTWNHLDYT
            IPYDGATRKL LSDVFGYVKP GKMTALMGES GAGKTTLLNV LAQRINMGVI
            TGDMLVNAKP LPASFNRSCG YVAQADNHMA ELSVRESLRF AAELRQQSSV
            PLEEKYEYVE KIITLLGMQN YAEALVGKTG RGLNVEQRKK LSIGVELVAK
            PSLLLFLDEP TSGLDSQSAW SIVQFMRALA DSGQSILCTI HQPSATLFEQ
            FDRLLLLKKG KMVYFGDIG PNSETLLKYF ERQSGMKCGV SENPAEYILN
            CIGAGATASV NSDWHDLWLA SPECAAARAE VEELHRTLPG RAVNDDPELA
            TRFAASYMTQ IKCVLRRTAL QFWRSPVYIR AKFFECVACA LFVGLSYVGV
            NHSVGGAIEA FSSIFMLLLI ALAMINQLHV FAYDSRELYE VREAASNTFH
            WSVLLLCHAA VENFWSTLCQ FMCFICYYWP AQFSGRASHA GFFFFFYVLI
            FPLYFVTYGL WILYMSPDVP SASMINSNLF AAMLLFCGIL QPREKMPAFW
            RRLMYNVSPF TYVVQALVTP LVHNKKVVCN PHEYNIMDPP SGKTCGEFLS
            TYMDNNTGYL VNPTATENCQ YCPYTVQDQV VAKYNVKWDH RWRNFGFMWA
            YICFNIAAML ICYYVRVKV WSLKSVLNFK KWFNGPRKER HEKDTNIFQT
            VPGDENKITK K -1511

SEQ ID NO: 23. Saccharomyces cerevisiae
            MDTQIAITGV AVGKEINNDN SKTDQKVSLP KADVPCIDKA TQTIIEGCSK
            DDPRLSYPTK LETTEKGKTK RNSFACVCCH SLQKCEPSD VNDIYRKPCR
            RCLKHKKLCK FDLSKRTRKR KPRSRSPTPF ESPMVNVSTK SKGPTDSEES
```

SEQUENCE LISTING

```
SLKDGTSYLA SFPSDPNAKQ FPNSRTVLPG LQQSLSDLWS TLSQPPSYGA
REAETTSTGE ITTNNHTKSN GSVPTNPAVL ASNDEHTNIS DAPVIYSTYN
SPVPISSAPT SINSEALFKH RPKIVGDEET QNVKVKRQKK SYSRHMTRSF
RKQLQSLIIS QKGKIRDISM KLDTWSKQWN DLVEKSMFLP TIADPVSVGI
ISHEEATLRL HLYKTEISYL SKLPPIKVEE NVSVDELRKK KPILFSVIMS
CVSIVLTPKQ TTRGTIMKLD SFVLNLITNQ IFKANNKSIE IIESLSTLCL
WYNFFEWSSK TRYHIFNYIC CCLTRDLGPT YVNRSFGMFS DEDPKRFKSP
LELYSNGASL TLLVYISALN ISIFLRQSIQ ARWSHVTEKA CEDLVKETKK
SRHYDNDKLL LDSADDPILV QFAKMNHVLE NIHTHLHERD LNDDEFDDPI
FTKKYLNKLM EKYHKQLQEI FTKLDRNRPR VIAFYYSVEA YLYQYKLAVF
IGEMSHTINE KVELPREIMD DFVKCYHCCK SALEEFSKLE PILITSLPLF
HTSRIIYTVG MLLLKLRYSV VAIPSFHDLM PLTDDAIALV IGVNNLLEKT
SELYPFNNSL YKFRYVIALF CQTYANKVID VADRYNAERE KLKEKQVIDE
VSNGHDGTKP INAYVTESQK MPTEEDPIID NNTNQNITAV PDEMLPVYSR
VRDDTAAMNL NINSTSYMNE SPHEHRESMT GTTLLPPPFI SNDVTNSADS
TNIKPSPSSS VDNLNDYLTD INSLAWGVNS LNDEFWTDLF MNDI
-944

SEQ ID NO: 24. Kluyveromyces marxianus
MSNSSSSEGK TNEDGRNSVH SSDSFAQSVA SFHLDDNESQ NVTAQLSQQI
TNVLSNSNGA ERIESLARVI STKTKKQMES FEVNQLDFDL KALLNYLRSS
QLEQGIEPGD SGIAFHDLTA VGIDASAAFG PSVEEMVRSW IHFPVRLWKK
ICRQKSETPL RNIIQHCTGV VESGEMLFVV GRPGAGCSTL LKCLSGETGE
LVEVTGDISY DGLSQEEMMQ KFKGYVIYCP ELDFHFPKIT VKETIDFALK
CKTPRSRIDH LTRAQYVDNM RDLWCTVFGL THTYATNVGN DVVRGVSGGE
RKRVSLVEAL AMNASIYSWD NATRGLDAST ALEFAQAIRT ATNMMNNSAI
VAIYQAGENI YQLFDKTTVL YNGKQVYFGP ADEAVGYFER MGYIKPNRMT
SAEFLTSATV DFENRTLEVR EGYEEKIPKS STEMEAYWHN SPEYAKATEL
FNEYCQSHPE EETRQRLETA KKQRLQKGQR EKSQFVVTFW AQVWYCMIRG
FQRVKGDSTY TKVYLSSFLT KGLIVGSMPH KIDPKSQSTT EGAYSRGGLL
FYVLLFAALT SLAEISNSFQ NRAIIVKQKT YSMYHTSAES LQEIFTEIPT
KFVAILTLSL VSYWIPVLKY DAGSPFQYLL YLFTTQQCTS FIPKLVATLT
KDGGTAHAIG GLWVLMLTVY AGFVLPIGNM HHWIRWFHYL NPLTYAYESL
MSTEFHGRKM LCSRLLPSGP GYENVSIAHK ICDAAGAVAG QLYVSGDAYV
LKKYHFRYKH AWRDWGINIV WTFGYIVMNV VMSEYLKPLE GGGDLLLYKR
GHMPELGSES VDSKVASREE MMESLNGPGV DLEKVIASKD VFTWNHLNYT
IPYDGATRQL LSDVFGYVKP GKMTALMGES GAGKTTLLNV LAQRINVGVI
TGDMLVNAKP LPPSFNRSCG YVAQADNHMG ELSVRESLRF AAELRQPKSV
PLQEKYDYVE KIISLLGMEK YAEAIIGKTG RGLNVEQRKK LSIGVELVAK
PSLLLFLDEP TSGLDSQSAW SIVQFMRALA DSGQSILCTI HQPSATLFEQ
FDRLLLLKKG GKMVYFGDIG ENSSTLLNYF ERQSGVKCGK SENPAEYMLN
CIGAGATASA DADWHDLWLQ SPECAAAREE VEELHRTLAS RPVTDDKELA
GRYAASYLTQ MKCVFRRTNI QFWRSPVYIR AKFLECVLCA LFVGLSYVGV
DHSIAGASQS FSSIFMMLLI ALAMVNQLHV FALDSRELYE VREAASNTFH
WSVLLLNHTF VEIIWSTLCE FICWICYYWP AQYSGRASHA GYFFLIYVIM
FPAYFVSYGC WVFYMSPDVP SASMINSNLF AGMLLFCGIL QPKDKMPGFW
KRFMYNVSPF TYVVQSLVTP LVQGKKVRCT KNEFAVVNPP EGQTCSQYFA
RFIKDNTGYL KNPNDTESCH YCPYSYQQEV VEQYNVRWVY RWRNFGFLWA
YIGFNFFAML ACYWVLRVKN YSITSIFGVF KIGNWKKAIH HDSRHEKDHT
IFQEKPGDAA NVQKTKA -1517

SEQ ID NO: 25. Artificial Sequence
MSSLKPKIKA ISMMPKLVLV RHGQSEWNEK NLFTGWVDVK LSAVGEKEAA
RAGELLKEAN IKPDVLYTSK LSRAIQTANI ALEKADRLWI PVKRSWRLNE
RHYGALQGKD KAETLEQYGE EKFQTWRRSF DVPPPPIEDD SEFSQKGDER
YADVDPAVLP KTESLALVID RLLPYWQDVI AKDLLAGKTV LIAAHGNSLR
ALVKHLDNIS DADIAGLNIP TGIPLVYELD ENLKPTKPAY YLDPEAAAAG
AAAVAAQGKK K -261

SEQ ID NO: 26. Artificial Sequence
MAISKIHARS VYDSRGNPTV EVDLTTEKGL FRAIVPSGAS TGIHEALELR
DGDKSKWLGK GVLKAVANVN DVIAPALIKA NIDVKDQSKV DEFLIKLDGT
PNKSKLGANA ILGVSLAAAK AAAAEKGVPL YAHIADLAGT KTKPYVLPVP
FQNVLNGGSH AGGALAFQEF MIVPTGAPSF SEALRIGSEV YHNLKSLAKK
KYGQSAGNVG DEGGVAPDIQ TAEEALDLIV DAIEAAGYTG KVKIALDVAS
SEFYKDDAGK YDLDFKNPES DPSKWLTGEQ LADLYHSLAK KYPIVSIEDP
FAEDDWEAWS HFYKTAGSDI QIVGDDLTVT NPIRIKTAIE KKAANALLLK
VNQIGTLTES IQAAKDSYAA GWGVMVSHRS GETEDTFIAD LVVGLRTGQI
KTGAPARSER LAKLNQILRI EEELGDKAIY AGENFHTAVN L -441

SEQ ID NO: 27. Schizosaccharomyces pombe
MGELKEILKQ RYHELLDWNV KAPHVPLSQR LKHFTWSWFA CTMATGGVGL
IIGSFPFRFY GLNTIGKIVY ILQIFLFSLF GSCMLRFIK YPSTIKDSWN
HHLEKLFIAT CLLSISTFID MLAIYAYPDT GEWMVWVIRI LYYIYVAVSF
IYCVMAFFTI FNNHVYTIET ASPAWILPIF PPMICGVIAG AVNSTQPAHQ
LKNMVIFGIL FQGLGFWVYL LLFAVNVLRF FTVGLAKPQD RPGMFMFVGP
PAFSGLALIN IARGAMGSRP YIFVGANSSE YLGFVSTFMA IFIWGLAAWC
```

SEQUENCE LISTING

```
YCLAMVSFLA GFFTRAPLKF ACGWFAFIFP NVGFVNCTIE IGKMIDSKAF
QMFGHIIGVI LCIQWILLMY LMVRAFLVND LCYPGKDEDA HPPPKPNTGV
LNPTFPPEKA PASLEKVDTH VTSTGGESDP PSSEHESV -438

SEQ ID NO: 28. Saccharomyces cerevisiae
MAVSKVYARS VYDSRGNPTV EVELTTEKGV FRSIVPSGAS TGVHEALEMR
DGDKSKWMGK GVLHAVKNVN DVIAPAFVKA NIDVKDQKAV DDFLISLDGT
ANKSKLGANA ILGVSLAASR AAAAEKNVPL YKHLADLSKS KTSPYVLPVP
FLNVLNGGSH AGGALALQEF MIAPTGAKTF AEALRIGSEV YHNLKSLTKK
RYGASAGNVG DEGGVAPNIQ TAEEALDLIV DAIKAAGHDG KIKIGLDCAS
SEFFKDGKYD LDFKNPNSDK SKWLTGPQLA DLYHSLMKRY PIVSIEDPFA
EDDWEAWSHF FKTAGIQIVA DDLTVTNPKR IATAIEKKAA DALLLKVNQI
GTLSESIKAA QDSFAAGWGV MVSHRSGETE DTFIADLVVG LRTGQIKTGA
PARSERLAKL NQLLRIEEEL GDNAVFAGEN FHHGDKL -437

SEQ ID NO: 29. Saccharomyces cerevisiae
MAVSKVYARS VYDSRGNPTV EVELTTEKGV FRSIVPSGAS TGVHEALEMR
DEDKSKWMGK GVMNAVNNVN NVIAAAFVKA NLDVKDQKAV DDFLLSLDGT
ANKSKLGANA ILGVSMAAAR AAAAEKNVPL YQHLADLSKS KTSPYVLPVP
FLNVLNGGSH AGGALALQEF MIAPTGAKTF AEAMRIGSEV YHNLKSLTKK
RYGASAGNVG DEGGVAPNIQ TAEEALDLIV DAIKAAGHDG KVKIGLDCAS
SEFFKDGKYD LDFKNPESDK SKWLTGVELA DMYHSLMKRY PIVSIEDPFA
EDDWEAWSHF FKTAGIQIVA DDLTVTNPAR IATAIEKKAA DALLLKVNQI
GTLSESIKAA QDSFAANWGV MVSHRSGETE DTFIADLVVG LRTGQIKTGA
PARSERLAKL NQLLRIEEEL GDKAVYAGEN FHHGDKL -437

SEQ ID NO: 30. Escherichia coli
MSVPVQHPMY IDGQFVTWRG DAWIDVVNPA TEAVISRIPD GQAEDARKAI
DAAERAQPEW EALPAIERAS WLRKISAGIR ERASEISALI VEEGGKIQQL
AEVEVAFTAD YIDYMAEWAR RYEGEIIQSD RPGENILLFK RALGVTTGIL
PWNFPFFLIA RKMAPALLTG NTIVIKPSEF TPNNAIAFAK IVDEIGLPRG
VFNLVLGRGE TVGQELAGNP KVAMVSMTGS VSAGEKIMAT AAKNITKVCL
ELGGKAPAIV MDDADLELAV KAIVDSRVIN SGQVCNCAER VYVQKGIYDQ
FVNRLGEAMQ AVQFGNPAER NDIAMGPLIN AAALEREVQK VARAVEEGAR
VAFGGKAVEG KGYYYPPTLL LDVRQEMSIM HEETFGPVLP VVAFDTLEDA
ISMANDSDYG LTSSIYTQNL NVAMKAIKGL KFGETYINRE NFEAMQGFHA
GWRKSGIGGA DGKHGLHEYL QTQVVYLQS -479
```

What is claimed is:

1. A recombinant host cell, comprising: a glyceric acid biosynthetic pathway, comprising heterologous nucleic acids encoding a 3-phosphoglycerate phosphatase and a 2-phosphoglycerate phosphatase, wherein the expression of the heterologous nucleic acids produces glyceric acid, wherein: the 3-phosphoglycerate phosphatase has the amino acid sequence selected from SEQ ID NO: 9 and SEQ ID NO: 7, and the 2-phosphoglycerate phosphatase has the amino acid sequence of SEQ ID NO: 1; and the recombinant host cell is a yeast cell or a prokaryotic cell.

2. The recombinant host cell of claim 1, wherein the yeast cell belongs to the genus *Pichia, Issatchenkia,* or *Candida*.

3. The recombinant host cell of claim 2, wherein the yeast cell is *Pichia kudriavzevii*.

4. The recombinant host cell of claim 2, wherein the yeast cell of the *Saccharomyces* clade.

5. The recombinant host cell of claim 4, wherein the yeast cell is *Saccharomyces cerevisiae*.

6. The recombinant host cell of claim 1, wherein the prokaryotic cell belongs to the genus *Escherichia, Corynebacterium, Bacillus*, or *Lactococcus*.

7. The recombinant host cell of claim 6, wherein the prokaryotic cell is *Escherichia coli, Corynebacterium glutamicum, Bacillus subtilis*, or *Lactococcus lactis*.

8. The recombinant host cell of claim 1, further comprising:
 a heterologous nucleic acid encoding a mitochondrial external NADH dehydrogenase;
 a nucleic acid encoding a water-forming NADH oxidase;
 a heterologous nucleic acid encoding a glyceric acid transporter; or
 combinations of the foregoing.

9. The recombinant host cell of claim 8, wherein the mitochondrial external NADH dehydrogenase has the amino acid sequence of SEQ ID NO: 20.

10. The recombinant host cell of claim 8, wherein the water-forming NADH dehydrogenase has the amino acid sequence of SEQ ID NO: 21.

11. The recombinant host cell of claim 8, wherein the glyceric acid transporter has the amino acid sequence selected from SEQ ID NO: 22, SEQ ID NO: 23, SEQ ID NO: 24, and SEQ ID NO: 27.

12. The recombinant host cell of claim 1, further comprising:
 a genetic disruption of an endogenous gene encoding a protein selected from phosphoglycerate mutase, phosphoglycerate dehydrogenase, enolase, glycerate 3-kinase, glycerate 2-kinase, glycerol-3-phosphate dehydrogenase, and combinations thereof.

13. The recombinant host cell of claim 12, wherein the phosphoglycerate mutase has the amino acid sequence of SEQ ID NO: 14.

14. A method of producing glyceric acid, comprising:
 culturing the recombinant host cell of claim 1 under conditions suitable to produce glyceric acid.

* * * * *